United States Patent
Gerlach et al.

(10) Patent No.: US 8,309,542 B2
(45) Date of Patent: Nov. 13, 2012

(54) SUBSTITUTED PYRROLIDINE AMIDES, THE PRODUCTION THEREOF, AND THE USE THEREOF AS MEDICATIONS

(75) Inventors: Kai Gerlach, Mittelbiberach (DE); Henning Priepke, Warthausen (DE); Wolfgang Wienen, Biberach (DE); Annette Schuler-Metz, Ulm (DE); Georg Dahmann, Attenweiler (DE); Herbert Nar, Ochsenhausen (DE)

(73) Assignee: Boehringer Ingelheim International GmbH, Ingelheim am Rhein (DE)

( * ) Notice: Subject to any disclaimer, the term of this patent is extended or adjusted under 35 U.S.C. 154(b) by 379 days.

(21) Appl. No.: 12/531,343

(22) PCT Filed: Mar. 26, 2008

(86) PCT No.: PCT/EP2008/053568
§ 371 (c)(1),
(2), (4) Date: Dec. 4, 2009

(87) PCT Pub. No.: WO2008/116881
PCT Pub. Date: Oct. 2, 2008

(65) Prior Publication Data
US 2010/0099664 A1    Apr. 22, 2010

(30) Foreign Application Priority Data
Mar. 27, 2007  (EP) .................................... 07105053

(51) Int. Cl.
*A61K 31/55*     (2006.01)
*C07D 223/16*    (2006.01)

(52) U.S. Cl. ........................................ 514/215; 540/593
(58) Field of Classification Search .................... None
See application file for complete search history.

(56) References Cited

U.S. PATENT DOCUMENTS

| | | | |
|---|---|---|---|
| 2007/0032473 A1 | 2/2007 | Gerlach et al. | |
| 2008/0139605 A1 | 6/2008 | Gerlach et al. | |
| 2009/0048231 A1 | 2/2009 | Priepke et al. | |

FOREIGN PATENT DOCUMENTS

| | | |
|---|---|---|
| CA | 2 613 059 A1 | 1/2007 |
| CA | 2 615 447 A1 | 1/2007 |
| CA | 2 641 912 A1 | 8/2007 |
| CA | 2 653 753 A1 | 11/2007 |
| WO | 2004/017908 A2 | 3/2004 |
| WO | 2005/032472 A2 | 4/2005 |
| WO | 2006/114401 A2 | 11/2006 |
| WO | 2007/003536 A1 | 1/2007 |
| WO | 2007/009963 A1 | 1/2007 |
| WO | 2007/093595 A1 | 8/2007 |
| WO | 2007/131982 A2 | 11/2007 |

OTHER PUBLICATIONS

International Search Report for PCT/EP2008/053568 mailed Aug. 5, 2008.

*Primary Examiner* — Noble Jarrell
(74) *Attorney, Agent, or Firm* — Michael P. Morris; Edouard G. Lebel; Usha R. Patel

(57) ABSTRACT

The object of the present invention is novel substituted pyrrolidine amides of the general formula (I) in which D, L, E, G, J, M, $L^1$, $L^2$, $R^4$, and $R^5$ are defined as in the specification, the tautomers, enantiomers, diastereomers, mixtures, and salts thereof, particularly physiologically tolerated salts with inorganic or organic acids or bases having valuable properties.

10 Claims, No Drawings

SUBSTITUTED PYRROLIDINE AMIDES, THE PRODUCTION THEREOF, AND THE USE THEREOF AS MEDICATIONS

This application is the national phase entry under 35 U.S.C. §371 of International Application No. PCT/EP2008/053568, filed Mar. 26, 2008, which claims priority to European Patent Application No. 07105053.8, filed Mar. 27, 2007, which are hereby incorporated by reference in their entireties.

The present invention relates to new substituted pyrrolidinamides of general formula (I)

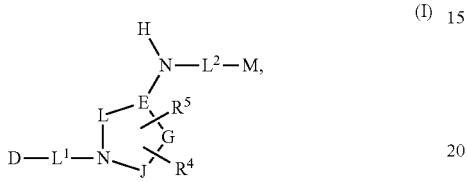

the tautomers, the enantiomers, the diastereomers, the mixtures and the salts thereof, particularly the physiologically acceptable salts thereof with inorganic or organic acids or bases, which have valuable properties.

The compounds of the above general formula (I) as well as the tautomers, the enantiomers, the diastereomers, the mixtures and the salts thereof, particularly the physiologically acceptable salts thereof with inorganic or organic acids or bases, and the stereoisomers thereof, have valuable pharmacological properties, particularly an antithrombotic activity and a factor Xa-inhibiting activity.

The present application relates to new compounds of the above general formula (I), the preparation thereof, the pharmaceutical compositions containing the pharmacologically effective compounds, the preparation and use thereof.

A 1st embodiment of the present invention encompasses those compounds of general formula (I), wherein
D denotes a substituted bicyclic ring system of formula (IIa), (IIb) or (IIc)

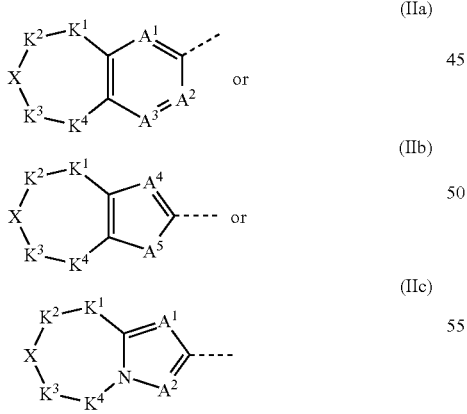

wherein
$K^1$ and $K^4$
each independently denote a bond, a —$CH_2$—, —$CHR^{7a}$—, —$CR^{7b}R^{7c}$— or a —C(O) group, and wherein $R^{7a}/R^{7b}/R^{7c}$
each independently denote a fluorine atom, a hydroxy, $C_{1-5}$-alkyloxy, amino, $C_{1-5}$-alkylamino, di-($C_{1-5}$-alkyl)-amino, $C_{3-5}$-cycloalkyleneimino, $C_{1-5}$-alkyl-carbonylamino group, a $C_{1-5}$-alkyl group which may be substituted by 1-3 fluorine atoms, a hydroxy-$C_{1-5}$-alkyl, $C_{1-5}$-alkyloxy-$C_{1-5}$-alkyl, amino-$C_{1-5}$-alkyl, $C_{1-5}$-alkylamino-$C_{1-5}$-alkyl, di-($C_{1-5}$-alkyl)-amino-$C_{1-5}$-alkyl, $C_{4-7}$-cycloalkyleneimino-$C_{1-5}$-alkyl, carboxy-$C_{0-5}$-alkyl, $C_{1-5}$-alkyloxycarbonyl-$C_{0-5}$-alkyl, aminocarbonyl-$C_{0-5}$-alkyl, $C_{1-5}$-alkylaminocarbonyl-$C_{0-5}$-alkyl, di-($C_{1-5}$-alkyl)-aminocarbonyl-$C_{0-5}$-alkyl or a $C_{4-7}$-cycloalkyleneiminocarbonyl-$C_{0-5}$-alkyl group,
wherein the two groups $R^{7b}/R^{7c}$ may not simultaneously be bound to the cyclic carbon atom via a heteroatom, except where —C($R^{7b}R^{7c}$)— corresponds to a —$CF_2$ group, or
$R^{7a}$ denotes a phenyl or monocyclic heteroaryl group substituted by fluorine, chlorine, bromine, methyl, methoxy, amino or nitro, or
two groups $R^{7b}/R^{7c}$ together with the cyclic carbon atom may form a 3-, 4-, 5-, 6- or 7-membered saturated carbocyclic group or a cyclopentene, cyclohexene, oxetan, azetidine, thietan, tetrahydrofuran, pyrrolidine, tetrahydrothiophene, tetrahydropyran, piperidine, pentamethylene sulphide, hexamethyleneimine, 1,3-dioxolan, 1,4-dioxane, hexahydropyridazine, piperazine, thiomorpholine, morpholine, 2-imidazolidinone, 2-oxazolidinone, tetrahydro-2(1H)-pyrimidinone or [1,3]oxazinan-2-one ring,
wherein the methylene groups thereof may be substituted by 1-2 $C_{1-3}$-alkyl or $CF_3$— groups, and/or
the methylene groups thereof, if they are not bound to a heteroatom, may be substituted by 1-2 fluorine atoms, and/or
wherein a —$CH_2$ group, besides being replaced by an N atom, may be replaced by a —CO group, and/or
the imino groups thereof may each be substituted by a $C_{1-3}$-alkyl or $C_{1-3}$-alkylcarbonyl group, and/or
wherein the sulphur atom may be oxidised to form a sulphoxide or sulphone group,
$K^2$ and $K^3$
each independently denote a —$CH_2$, —$CHR^{8a}$, —$CR^{8b}R^{8c}$ or a —C(O) group, wherein $R^{8a}/R^{8b}/R^{8c}$
each independently denote a $C_{1-5}$-alkyl group which may be substituted by 1-3 fluorine atoms, a hydroxy-$C_{1-5}$-alkyl, $C_{1-5}$-alkyloxy-$C_{1-5}$-alkyl, amino-$C_{1-5}$-alkyl, $C_{1-5}$-alkylamino-$C_{1-5}$-alkyl, di-($C_{1-5}$-alkyl)-amino-$C_{1-5}$-alkyl, $C_{4-7}$-cycloalkyleneimino-$C_{1-5}$-alkyl, carboxy-$C_{0-5}$-alkyl, $C_{1-5}$-alkyloxycarbonyl-$C_{0-5}$-alkyl, aminocarbonyl-$C_{0-5}$-alkyl, $C_{1-5}$-alkylaminocarbonyl-$C_{0-5}$-alkyl, di-($C_{1-5}$-alkyl)-aminocarbonyl-$C_{0-5}$-alkyl or a $C_{4-7}$-cycloalkyleneiminocarbonyl-$C_{0-5}$-alkyl group,
or two groups $R^{8b}/R^{8c}$ together with the cyclic carbon atom may form a 3-, 4-, 5-, 6- or 7-membered saturated carbocyclic group or a cyclopentene, cyclohexene, oxetan, azetidine, thietan, tetrahydrofuran, pyrrolidine, tetrahydrothiophene, tetrahydropyran, piperidine, pentamethylene sulphide, hexamethyleneimine, hexahydropyridazine, tetrahydro-2(1H)-pyrimidinone, [1,3]oxazinan-2-one ring,
wherein the methylene groups thereof may be substituted by 1-2 $C_{1-3}$-alkyl or $CF_3$— groups, and/or
the methylene groups thereof, if they are not bound to a heteroatom, may be substituted by 1-2 fluorine atoms, and/or
wherein a —$CH_2$ group, besides being replaced by a nitrogen atom, may be replaced by a —CO group, and/or the imino groups thereof may each be substituted by a $C_{1-3}$-alkyl or $C_{1-3}$-alkylcarbonyl group, and/or wherein the sulphur atom may be oxidised to form a sulphoxide or sulphone group, with the proviso that a heteroatom introduced by $R^{8b}$ or $R^{8c}$ must not be only one carbon atom away from X in formula (I), and in all, in formula (IIa) or (IIb) or (IIc) a maximum of four groups selected from among $R^{7a}$, $R^{7b}$, $R^{7c}$, $R^{8a}$, $R^{8b}$ and $R^{8c}$ may be present, and X denotes an oxygen or sulphur atom, a $CF_2$, sulphene, sulphone or a $NR^1$ group, wherein $R^1$ denotes a hydrogen atom or a hydroxy, $C_{1-3}$-alkyloxy, amino, $C_{1-3}$-alkylamino, di-($C_{1-3}$-alkyl)-amino, a $C_{1-5}$-alkyl, $C_{2-5}$-alkenyl-$CH_2$, $C_{2-5}$-alkynyl-$CH_2$, $C_{3-6}$-cycloalkyl, $C_{4-6}$-cycloalkenyl, oxetan-3-yl, tetrahydrofuran-3-yl, benzyl, $C_{1-5}$-alkyl-carbonyl, trifluoromethylcarbonyl, $C_{3-6}$-cycloalkyl-carbonyl, $C_{1-5}$-alkyl-sulphonyl, $C_{3-6}$-cycloalkyl-sulphonyl, aminocarbonyl, $C_{1-5}$-alkylaminocarbonyl, di-($C_{1-5}$-alkyl)-aminocarbonyl, $C_{1-5}$-alkyloxycarbonyl, $C_{4-7}$-cycloalkyleneiminocarbonyl group, wherein the methylene and methyl groups present in the groups mentioned previously may additionally be substituted by a $C_{1-3}$-alkyl, carboxy, $C_{1-5}$-alkoxycarbonyl group, or by a hydroxy, $C_{1-5}$-alkyloxy, amino, $C_{1-5}$-alkylamino, $C_{1-5}$-dialkylamino or $C_{4-7}$-cycloalkyleneimino group, provided that the methylene or methyl groups are not directly bound to a heteroatom selected from among O, N and S, and/or one to three hydrogen atoms may be replaced by fluorine atoms, provided that the methylene or methyl groups are not directly bound to a heteroatom selected from among O, N and S, and wherein $A^1$ denotes either N or $CR^{10}$,
$A^2$ denotes either N or $CR^{11}$,
$A^3$ denotes either N or $CR^{12}$,
$A^4$ denotes either N or $CR^{12}$,
$A^5$ denotes NH, sulphur or oxygen, while $R^{10}$, $R^{11}$ and $R^{12}$ each independently denote a hydrogen, fluorine, chlorine, bromine or iodine atom, or a $C_{1-5}$-alkyl, $CF_3$, $C_{2-5}$-alkenyl, $C_{2-5}$-alkynyl, a phenyl, a cyano, carboxy, $C_{1-5}$-alkyloxycarbonyl, hydroxy, $C_{1-3}$-alkyloxy, $CF_3O$, $CHF_2O$, $CH_2FO$, amino, $C_{1-5}$-alkylamino, di-($C_{1-5}$-alkyl)-amino or $C_{4-7}$-cycloalkyleneimino group, and -L-E-G-J- denotes a —C—C—C—C group which may be substituted by $R^4$ and $R^5$, and $L^1$ denotes a —C(O) group, and $R^4$ denotes a hydrogen atom or a straight-chain or branched $C_{1-6}$-alkyl, $C_{2-6}$-alkenyl or $C_{2-6}$-alkynyl group, wherein the hydrogen atoms of the methylene and/or methyl fragments of the straight-chain or branched $C_{1-6}$-alkyl, $C_{2-6}$-alkenyl or $C_{2-6}$-alkynyl group may optionally be wholly or partly replaced by fluorine atoms, and/or wherein the hydrogen atoms of the methylene and/or methyl fragments of the straight-chain or branched $C_{1-6}$-alkyl, $C_{2-6}$-alkenyl or $C_{2-6}$-alkynyl group may optionally each be substituted independently by one to two substituents selected from a $C_{3-5}$-cycloalkyl group, a nitrile, hydroxy or $C_{1-5}$-alkyloxy group, wherein the hydrogen atoms of the $C_{1-5}$-alkyloxy group may optionally be wholly or partly replaced by fluorine atoms, an allyloxy, propargyloxy, benzyloxy, $C_{1-5}$-alkylcarbonyloxy, $C_{1-5}$-alkylaminocarbonyloxy, di-($C_{1-5}$-alkyl)-aminocarbonyloxy, $C_{1-5}$-alkyloxycarbonyloxy, carboxy-$C_{1-5}$-alkyloxy, $C_{1-5}$-alkyloxycarbonyl-$C_{1-5}$-alkyloxy, mercapto, $C_{1-5}$-alkylsulphanyl, $C_{1-5}$-alkylsulphinyl, $C_{1-5}$-alkylsulphonyl, carboxy, $C_{1-5}$-alkyloxycarbonyl, aminocarbonyl, $C_{1-5}$-alkylaminocarbonyl, di-($C_{1-5}$-alkyl)-aminocarbonyl, $C_{4-7}$-cycloalkyleneiminocarbonyl, aminosulphonyl, $C_{1-5}$-alkylaminosulphonyl, di-($C_{1-5}$-alkyl)-aminosulphonyl, $C_{4-7}$-cycloalkyleneiminosulphonyl, amino, $C_{1-5}$-alkylamino, di-($C_{1-5}$-alkyl)-amino, $C_{1-5}$-alkylcarbonylamino, $C_{1-3}$-alkyloxy-$C_{1-2}$alkylcarbonylamino, $C_{1-3}$-alkyloxycarbonylamino, $C_{1-3}$-alkylaminocarbonylamino, $C_{1-5}$-alkylsulphonylamino, N-($C_{1-5}$-alkylsulphonyl)-$C_{1-5}$-alkylamino, $C_{3-6}$-cycloalkylcarbonyl-amino group, or einer morpholinyl, thiomorpholinyl, pyrrolidinyl, piperidinyl, piperazinyl, tetrahydrofuranyl, tetrahydropyranyl group, while the above-mentioned carbocyclic and heterocyclic groups in the ring may each be substituted by 1-4 $C_{1-3}$-alkyl or $C_{1-3}$-alkylcarbonyl groups or in each case by 1-2 oxo groups, and/or wherein the hydrogen atoms of the $sp^2$-hybridised carbon atoms of the straight-chain or branched $C_{2-6}$-alkenyl group may optionally be wholly or partly replaced by fluorine atoms, or a nitrile, carboxy, aminocarbonyl, $C_{1-5}$-alkylaminocarbonyl, $C_{3-6}$-cycloalkylaminocarbonyl, di-($C_{1-5}$-alkyl)-aminocarbonyl, $C_{1-5}$-alkyloxycarbonyl or a $C_{4-7}$-cycloalkyleneiminocarbonyl group wherein a methylene group may optionally be replaced by an oxygen, sulphur or $C_{0-3}$-alkyl-substituted nitrogen atom, or a phenyl, mono- or bicyclic heteroaryl, phenyl-$C_{1-5}$-alkyl or mono- or bicyclic heteroaryl-$C_{1-5}$-alkyl group, which may optionally be mono- to trisubstituted in the phenyl or heteroaryl moiety by identical or different substituents selected from among fluorine, chlorine, bromine and iodine atoms, and $C_{1-5}$-alkyl, trifluoromethyl, amino, $C_{1-5}$-alkyl-amino, di-($C_{1-5}$-alkyl)-amino, hydroxy, $C_{1-5}$-alkyloxy, mono-, di- or trifluoromethoxy, carboxy- and $C_{1-5}$-alkyloxycarbonyl group, or if $R^4$ is linked to G it may also denote a fluorine atom or a hydroxy, $C_{1-5}$-alkyl-oxy, $C_{2-5}$-alkenyl-oxy, $C_{2-5}$-alkynyl-oxy, $C_{3-6}$-cycloalkyl-oxy, $C_{1-5}$-alkylaminocarbonyloxy, di($C_{1-5}$-alkyl)aminocarbonyloxy or $C_{4-7}$-cycloalkyleneiminocarbonyloxy, phenyl-$C_{0-3}$-alkyloxy, heteroaryl-$C_{0-3}$-alkyl-oxy, amino, $C_{1-5}$-alkylamino, di-($C_{1-5}$-alkyl)-amino, $C_{4-7}$-cycloalkyleneimino, $C_{1-3}$-acylamino, ($C_{1-3}$-acyl)$C_{1-3}$-alkylamino, $C_{1-5}$-alkyloxycarbonylamino, $C_{1-5}$-alkylaminocarbonylamino, di($C_{1-5}$-alkyl)aminocarbonylamino or a $C_{4-7}$-cycloalkyleneiminocarbonylamino-group, wherein the methyl or methylene groups present in the above-mentioned alkyl or cycloalkyl groups may each independently be substituted by a substituent selected from among morpholinyl, thiomorpholinyl, pyrrolidinyl, piperidinyl, piperazinyl, tetrahydrofuranyl, tetrahydropyranyl, dimethylaminocarbonyl, $C_{1-5}$-alkyloxycarbonyl, carboxy, methyl, hydroxy, methoxy or amino, and the above-mentioned phenyl or heteroaryl groups may optionally be mono- to trisubstituted by identical or different substituents selected from among fluorine, chlorine, bromine and iodine atoms, and $C_{1-5}$-alkyl, trifluoromethyl, amino, $C_{1-5}$-alkyl-amino, di-($C_{1-5}$-alkyl)-amino, hydroxy, $C_{1-5}$-alkyloxy, mono-, di- or trifluoromethoxy, carboxy- and $C_{1-5}$-alkyloxycarbonyl group, with the proviso that two heteroatoms selected from among oxygen and nitrogen are separated from one another by precisely one optionally substituted —CH$_2$ group, and/or that two atoms form an —O—O or —S—O bond, is excluded, and $R^5$ denotes a hydrogen atom, a $C_{1-5}$ alkyl, $C_{2-5}$ alkenyl or $C_{2-5}$ alkynyl or a phenyl-$C_{0-5}$ alkyl group, wherein the alkyl group may be substituted by a hydroxy, methoxy, hydroxycarbonyl or $C_{1-5}$alkoxycarbonyl group, or if $R^5$ is linked to G it may also denote a hydroxy or methoxy group, or $R^4$ and $R^5$ provided that they are bound to the same carbon atom, may form, together with the carbon atom, a —C═O group or a —CF$_2$ group, or $R^4$ and $R^5$ provided that they are bound to the same carbon atom or to two adjacent carbon atoms, may form, together with the carbon atom or atoms a 3-7-membered carbocyclic group or a monounsaturated 5-7 membered carbocyclic group wherein one of the carbon chain members of this cyclic group may be replaced by an oxygen or sulphur atom or an —NH, —N($C_{1-5}$-alkyl), —N($C_{1-4}$-alkylcarbonyl) or a carbonyl, sulphinyl or sulphonyl group, and/or wherein two directly adjacent carbon chain members of these $C_{4-7}$-carbocyclic groups may together be replaced by a —C(O)NH, —C(O)N($C_{1-5}$-alkyl), —S(O)$_2$NH or —S(O)$_2$N($C_{1-5}$-alkyl) group, and/or wherein four directly adjacent carbon chain members of these $C_{5-7}$-carbocyclic groups may together be replaced by a —O—CH$_2$—CH$_2$—O group, and/or wherein 1 to 3 carbon atoms of these 3-7-membered cyclic groups may optionally each be substituted independently of one another by one or two fluorine atoms or one or two $C_{1-5}$-alkyl groups or a hydroxy, $C_{1-5}$-alkyloxy, $C_{1-5}$-alkylcarbonyloxy, amino, $C_{1-5}$-alkylamino, di-($C_{1-5}$-alkyl)-amino, $C_{4-7}$-cycloalkyleneimino, $C_{1-5}$-alkylcarbonylamino, $C_{3-6}$-cycloalkylcarbonylamino, nitrile, carboxy-$C_{1-5}$-alkyl, $C_{1-5}$-alkyloxycarbonyl-$C_{1-5}$-alkyl, carboxy, $C_{1-5}$-alkyloxycarbonyl, aminocarbonyl, $C_{1-5}$-alkylaminocarbonyl, di-($C_{1-5}$-alkyl)-aminocarbonyl or $C_{4-7}$-cycloalkyleneiminocarbonyl group, with the proviso that a cyclic group formed from $R^4$ and $R^5$ together, wherein two nitrogen atoms or one nitrogen and one oxygen atom in the cyclic group are separated from one another by precisely one optionally substituted —CH$_2$ group, and/or wherein two atoms in the ring form an —O—O or —S—O— bond, is excluded, and $L^2$ denotes a —C(O) group, and M denotes a phenyl, pyridyl, thienyl or furyl ring optionally substituted by $R^2$ and $R^3$, wherein $R^2$ denotes a fluorine, chlorine, bromine or iodine atom or a methyl, ethyl, vinyl, methoxy, ethynyl, cyano or —C(O)NH$_2$ group, and $R^3$ denotes a hydrogen, fluorine, chlorine, bromine or iodine atom or a hydroxy, methoxy, trifluoromethoxy group, or a $C_{1-3}$-alkyl group optionally substituted by fluorine atoms, or a cyano, amino or NH$_2$C(O) group, while, unless stated otherwise, by the term "heteroaryl group" mentioned in the definitions hereinbefore is meant a monocyclic 5- or 6-membered heteroaryl group, wherein the 6-membered heteroaryl group contains one, two or three nitrogen atoms, and the 5-membered heteroaryl group contains an imino group optionally substituted by a $C_{1-3}$-alkyl group or an oxygen or sulphur atom, or an imino group optionally substituted by a $C_{1-3}$-alkyl group or an oxygen or sulphur atom and additionally one or two nitrogen atoms, or an imino group optionally substituted by a $C_{1-3}$-alkyl group and three nitrogen atoms, and moreover a phenyl ring optionally substituted by a fluorine, chlorine or bromine atom or by a $C_{1-3}$-alkyl, hydroxy, $C_{1-3}$-alkyloxy group, amino, $C_{1-3}$-alkylamino, di-($C_{1-3}$-alkyl)-amino or $C_{3-6}$-cycloalkyleneimino group may be fused to the above-mentioned monocyclic heteroaryl groups via two adjacent carbon atoms, and the bond is effected via a nitrogen atom or a carbon atom of the heterocyclic moiety or a fused-on phenyl ring, and wherein, unless stated otherwise, by the term "halogen atom" mentioned in the definitions hereinbefore is meant an atom selected from among fluorine, chlorine, bromine and iodine, and wherein, unless stated otherwise, the alkyl, alkenyl, alkynyl and alkyloxy groups contained in the definitions mentioned previously which have more than two carbon atoms may be straight-chain or branched and the alkyl groups in the previously mentioned dialkylated groups, for example the dialkylamino groups, may be identical or different, and the hydrogen atoms of the methyl or ethyl groups contained in the foregoing definitions, unless otherwise stated, may be wholly or partly replaced by fluorine atoms, the tautomers, enantiomers, diastereomers, mixtures and salts thereof.

Examples of monocyclic heteroaryl groups are the pyridyl, N-oxy-pyridyl, pyrazolyl, pyridazinyl, pyrimidinyl, pyrazinyl, [1,2,3]triazinyl, [1,3,5]triazinyl, [1,2,4]triazinyl, pyrrolyl, imidazolyl, [1,2,4]triazolyl, [1,2,3]triazolyl, tetrazolyl, furanyl, isoxazolyl, oxazolyl, [1,2,3]oxadiazolyl, [1,2,4]oxadiazolyl, furazanyl, thienyl, thiazolyl, isothiazolyl, [1,2,3]thiadiazolyl, [1,2,4]thiadiazolyl or [1,2,5]thiadiazolylgroup.

Examples of bicyclic heteroaryl groups are the benzimidazolyl, benzofuranyl, benzo[c]furanyl, benzothiophenyl, benzo[c]thiophenyl, benzothiazolyl, benzo[c]-isothiazolyl, benzo[d]isothiazolyl, benzoxazolyl, benzo[c]isoxazolyl, benzo[d]-isoxazolyl, benzo[1,2,5]oxadiazolyl, benzo[1,2,5]thiadiazolyl, benzo[1,2,3]thia-diazolyl, benzo[d][1,2,3]triazinyl, benzo[1,2,4]triazinyl, benzotriazolyl, cinnolinyl, quinolinyl, N-oxy-quinolinyl, isoquinolinyl, quinazolinyl, N-oxy-quinazolinyl, quinoxalinyl, phthalazinyl, indolyl, isoindolyl or 1-oxa-2,3-diaza-indenyl group.

Examples of the $C_{1-6}$-alkyl groups mentioned hereinbefore in the definitions are the methyl, ethyl, 1-propyl, 2-propyl, n-butyl, sec-butyl, tert-butyl, 1-pentyl, 2-pentyl, 3-pentyl, neo-pentyl, 3-methyl-2-butyl, 1-hexyl, 2-hexyl, 3-hexyl, 3-methyl-2-pentyl, 4-methyl-2-pentyl, 3-methyl-3-pentyl, 2-methyl-3-pentyl, 2,2-dimethyl-3-butyl or 2,3-dimethyl-2-butyl group.

Examples of the $C_{1-5}$-alkyloxy groups mentioned hereinbefore in the definitions are the methyloxy, ethyloxy, 1-propyloxy, 2-propyloxy, n-butyloxy, sec-butyloxy, tert-butyloxy, 1-pentyloxy, 2-pentyloxy, 3-pentyloxy or neo-pentyloxy group.

Examples of the $C_{2-5}$-alkenyl groups mentioned hereinbefore in the definitions are the ethenyl, 1-propen-1-yl, 2-propen-1-yl, 1-buten-1-yl, 2-buten-1-yl, 3-buten-1-yl, 1-penten-1-yl, 2-penten-1-yl, 3-penten-1-yl, 4-penten-1-yl, 1-hexen-1-yl, 2-hexen-1-yl, 3-hexen-1-yl, 4-hexen-1-yl, 5-hexen-1-yl, but-1-en-2-yl, 2-en-2-yl, but-1-en-3-yl, 2-methyl-prop-2-en-1-yl, pent-1-en-2-yl, pent-2-en-2-yl, pent-3-en-2-yl, pent-4- en-2-yl, pent-1-en-3-yl, pent-2-en-3-yl, 2-methyl-but-1-en-1-yl, 2-methyl-but-2-en-1-yl, 2-methyl-but-3-en-1-yl or 2-ethyl-prop-2-en-1-yl group, Examples of the $C_{2-5}$-alkynyl groups mentioned hereinbefore in the definitions are the ethynyl, 1-propynyl, 2-propynyl, 1-butyn-1-yl, 1-butyn-3-yl, 2-butyn-1-yl, 3-butyn-1-yl, 1-pentyn-1-yl, 1-pentyn-3-yl, 1-pentyn-4-yl, 2-pentyn-1-yl, 2-pentyn-3-yl, 3-pentyn-1-yl, 4-pentyn-1-yl, 2-methyl-1-butyn-4-yl, 3-methyl-1-butyn-1-yl or 3-methyl-1-butyn-3-yl group.

A 2nd embodiment of the present invention encompasses those compounds of general formula (I) wherein D, E, G, J, L, $L^1$, $L^2$ and M are defined as described in embodiment 1, and wherein $R^4$ denotes a hydrogen atom or
  a straight-chain or branched $C_{1-6}$-alkyl group,
    wherein the hydrogen atoms of the methylene and/or methyl fragments of the straight-chain or branched $C_{1-6}$-alkyl group may optionally be wholly or partly replaced by fluorine atoms, and/or
    wherein the hydrogen atoms of the methylene and/or methyl fragments of the straight-chain or branched $C_{1-6}$-alkyl group may optionally each independently be substituted by a substituent selected from a hydroxy, $C_{1-5}$-alkyloxy, $C_{1-5}$-alkylaminocarbonyloxy, di-($C_{1-5}$-alkyl)-aminocarbonyloxy, carboxy, $C_{1-5}$-alkyloxycarbonyl, aminocarbonyl, $C_{1-5}$-alkylaminocarbonyl, di-($C_{1-5}$-alkyl)-aminocarbonyl, $C_{4-7}$-cycloalkyleneiminocarbonyl, amino, $C_{1-5}$-alkylamino, di-($C_{1-5}$-alkyl)-amino, $C_{1-5}$-alkylcarbonylamino, $C_{1-3}$-alkyloxy-$C_{1-2}$alkylcarbonylamino, $C_{1-3}$-alkyloxycarbonylamino, $C_{1-3}$-alkylaminocarbonylamino, $C_{1-5}$-alkylsulphonylamino, N-($C_{1-5}$-alkylsulphonyl)-$C_{1-5}$-alkylamino, $C_{3-6}$-cycloalkylcarbonyl-amino group, or
  a nitrile, carboxy, aminocarbonyl, $C_{1-5}$-alkylaminocarbonyl, $C_{3-6}$-cycloalkylaminocarbonyl, di-($C_{1-5}$-alkyl)-aminocarbonyl, $C_{1-5}$-alkyloxycarbonyl or a $C_{4-7}$-cycloalkyleneiminocarbonyl group wherein a methylene group may optionally be replaced by an oxygen, sulphur or $C_{0-3}$-alkyl-substituted nitrogen atom, and
  or if $R^4$ is linked to G it may also denote a fluorine atom or a hydroxy, $C_{1-5}$-alkyl-oxy, $C_{2-5}$-alkenyl-oxy, $C_{2-5}$-alkynyl-oxy, $C_{3-6}$-cycloalkyl-oxy, $C_{1-5}$-alkylaminocarbonyloxy, di($C_{1-5}$-alkyl)aminocarbonyloxy or $C_{4-7}$-cycloalkyleneiminocarbonyloxy, phenyl-$C_{0-2}$-alkyloxy group, amino, $C_{1-5}$-alkylamino, di-($C_{1-5}$-alkyl)-amino, $C_{4-7}$-cycloalkyleneimino, $C_{1-3}$-acylamino, ($C_{1-3}$-acyl) $C_{1-3}$-alkylamino, $C_{1-5}$-alkyloxycarbonylamino, $C_{1-5}$-alkylaminocarbonylamino, di($C_{1-5}$-alkyl)aminocarbonylamino or a $C_{4-7}$-cycloalkyleneiminocarbonylamino group,
    wherein the methyl or methylene groups present in the above-mentioned alkyl or cycloalkyl groups may each independently be substituted by a substituent selected from among dimethylaminocarbonyl, $C_{1-5}$-alkyloxycarbonyl, carboxy, methyl, hydroxy, methoxy or amino, with the proviso that two heteroatoms selected from among oxygen and nitrogen are separated from one another by precisely one optionally substituted —$CH_2$ group, and/or
    that two atoms form an —O—O or —S—O— bond, is excluded, and
$R^5$ denotes a hydrogen atom or a $C_{1-5}$ alkyl, allyl, propargyl or benzyl group, or if $R^5$ is linked to G, it may also denote a hydroxy or methoxy group, or
$R^4$ and $R^5$ if they are bound to the same carbon atom, may form, together with the carbon atom, a —C═O group or a —$CF_2$— group, or $R^4$ and $R^5$ if they are bound to the same carbon atom or to two adjacent carbon atoms, may form, together with the carbon atom or atoms, a 3-7-membered carbocyclic group,
  wherein one of the carbon chain members of this cyclic group may be replaced by an oxygen or sulphur atom or a —NH, —N($C_{1-5}$-alkyl), —N($C_{1-4}$-alkylcarbonyl) or a carbonyl, sulphinyl or sulphonyl group, and/or
  wherein two directly adjacent carbon chain members of these $C_{4-7}$-carbocyclic groups may together be replaced by a —C(O)NH, —C(O)N($C_{1-5}$-alkyl), —S(O)$_2$NH, or —S(O)$_2$N($C_{1-5}$-alkyl) group, and/or
  wherein four directly adjacent carbon chain members of these $C_{5-7}$-carbocyclic groups may together be replaced by a —O—$CH_2$—$CH_2$O group,
  with the proviso that a cyclic group formed from $R^4$ and $R^5$ together,
    wherein two nitrogen atoms or one nitrogen and one oxygen atom in the cyclic group are separated from one another by precisely one optionally substituted —$CH_2$ group, and/or
    wherein two atoms in the ring form an —O—O or —S—O bond,
  is excluded, the tautomers, enantiomers, diastereomers, mixtures and salts thereof.

A 3rd embodiment of the present invention encompasses those compounds of general formula (I) wherein E, G, J, L, $L^1$, $L^2$, M, $R^4$ and $R^5$ are defined as described in embodiments 1 or 2, and wherein
D denotes a substituted bicyclic ring system of formula (IIa) or (IIb)

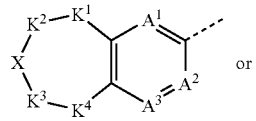

(IIa)

or

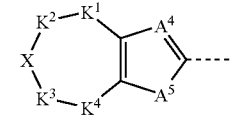

(IIb)

wherein
$K^1$ and $K^4$
  each independently denote a bond, a —$CH_2$, —$CHR^{7a}$, —$CR^{7b}R^{7c}$ or a —C(O) group, and wherein
  $R^{7a}/R^{7b}/R^{7c}$
    each independently denote a fluorine atom, a hydroxy, $C_{1-5}$-alkyloxy or a $C_{1-5}$-alkyl group,
    wherein the two groups $R^{7b}/R^{7c}$ may not simultaneously be bound to the cyclic carbon atom via a heteroatom, except where —C($R^{7b}R^{7c}$)— corresponds to a —$CF_2$ group, or
  two groups $R^{7b}/R^{7c}$ together with the cyclic carbon atom may form a 3-membered carbocyclic group,
  with the proviso that $K^1$ and $K^4$ simultaneously denote a bond, is excluded, and
$K^2$ and $K^3$
  each independently denote a —$CH_2$, —$CHR^{8a}$, —$CR^{8b}R^{8c}$ or a —C(O)— group, wherein
  $R^{8a}/R^{8b}/R^{8c}$
    each independently denote a $C_{1-5}$-alkyl group, and/or
  two groups $R^{8b}/R^{8c}$ together with the cyclic carbon atom may form a 3-membered saturated carbocyclic group
and
in all in formulae (IIa) or (IIb) not more than four groups selected from among $R^{7a}$, $R^{7b}$, $R^{7c}$, $R^{8a}$, $R^{8b}$ and $R^{8c}$ may be present, and X denotes an oxygen or sulphur atom, a —CF$_2$— or a NR$^1$ group, wherein
  R$^1$ denotes a hydrogen atom or a hydroxy, C$_{1-3}$-alkyloxy, amino, C$_{1-3}$-alkylamino, di-(C$_{1-3}$-alkyl)-amino, a C$_{1-5}$-alkyl, C$_{2-5}$-alkenyl-CH$_2$, C$_{2-5}$-alkynyl-CH$_2$ or a C$_{3-6}$-cycloalkyl group,
and wherein
A$^1$ denotes either N or CR$^{10}$,
A$^2$ denotes either N or CR$^{11}$,
A$^3$ denotes either N or CR$^{12}$,
A$^4$ denotes either N or CR$^{12}$,
A$^5$ denotes NH, sulphur or oxygen,
  wherein R$^{10}$, R$^{11}$ and R$^{12}$ each independently denote
    a hydrogen, fluorine, chlorine, bromine or iodine atom, or a C$_{1-5}$-alkyl, CF$_3$, a cyano, carboxy, C$_{1-5}$-alkyloxycarbonyl, hydroxy, C$_{1-3}$-alkyloxy, CF$_3$O, CHF$_2$O, CH$_2$FO, amino, C$_{1-5}$-alkylamino, di-(C$_{1-5}$-alkyl)-amino or C$_{4-7}$-cycloalkyleneimino group,
the tautomers, enantiomers, diastereomers, mixtures and salts thereof.

A 4th embodiment of the present invention encompasses those compounds of embodiments 1, 2 or 3, wherein
X denotes a NR$^1$ group, wherein
  R$^1$ denotes a hydrogen atom or a C$_{1-5}$-alkyl, allyl or cyclopropyl group, and
A$^1$ denotes CR$^{10}$,
A$^2$ denotes CR$^{11}$,
A$^3$ denotes CR$^{12}$,
A$^4$ denotes either N or CR$^{12}$,
A$^5$ denotes sulphur,
  while R$^{10}$, R$^{11}$ and R$^{12}$ each independently denote
    a hydrogen, fluorine or chlorine atom, or a methyl, CF$_3$, hydroxy, methoxy, CF$_3$O, CHF$_2$O, CH$_2$FO group,
the tautomers, enantiomers, diastereomers, mixtures and salts thereof.

A 5th embodiment of the present invention encompasses those compounds of embodiments 1, 2, 3 or 4, wherein
D denotes a substituted bicyclic ring system of formula

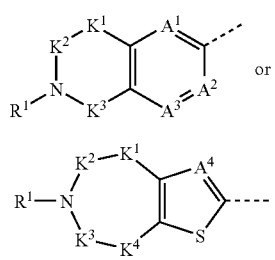

(IIe)

or (IIf)

wherein
K$^1$ denotes a —CH$_2$, —CHR$^{7a}$, or a —CR$^{7b}$R$^{7c}$— group, and
K$^2$ and K$^3$
  each independently denote a —CH$_2$, —CHR$^{8a}$, or a —CR$^{8b}$R$^{8c}$— group, wherein
  R$^{8a}$/R$^{8b}$/R$^{8c}$ each independently denote a C$_{1-5}$-alkyl group, and
K$^4$ denotes a bond, a —CH$_2$, —CHR$^{7a}$, —CR$^{7b}$R$^{7c}$ or a —C(O) group, wherein
  R$^{7a}$ denotes a C$_{1-5}$-alkyl group and
  R$^{7b}$/R$^{7c}$ each independently denote a hydroxy, C$_{1-5}$-alkyloxy or a C$_{1-5}$-alkyl group,
    wherein the two groups R$^{7b}$/R$^{7c}$ may not simultaneously be bound to the cyclic carbon atom via an oxygen atom, and in all, in formulae (IIe) or (IIf) not more than four groups selected from among R$^{7a}$, R$^{7b}$, R$^{7c}$, R$^{8a}$, R$^{8b}$ and R$^{8c}$ may be present, and
R$^1$ denotes a hydrogen atom or a C$_{1-3}$-alkyl, allyl or cyclopropyl group, and wherein
A$^1$ denotes CR$^{10}$,
A$^2$ denotes CR$^{11}$,
A$^3$ denotes CR$^{12}$,
A$^4$ denotes either N or CR$^{12}$,
  while R$^{10}$, R$^{11}$ and R$^{12}$ each independently denote
    a hydrogen, fluorine or chlorine atom, or a methyl, CF$_3$, hydroxy, methoxy, CF$_3$O, CHF$_2$O, CH$_2$FO group, and
-L-E-G-J- denotes a —C—C—C—C group which may be substituted by R$^4$ and R$^5$, and
R$^4$ denotes a hydrogen atom or
  a straight-chain or branched C$_{1-3}$-alkyl group,
    wherein the hydrogen atoms of the methylene and/or methyl fragments of the straight-chain or branched C$_{1-6}$-alkyl group may optionally be substituted independently of one another by a substituent selected from a hydroxy, C$_{1-5}$-alkyloxy, C$_{1-5}$-alkylaminocarbonyloxy, di-(C$_{1-5}$-alkyl)-aminocarbonyloxy, carboxy, C$_{1-5}$-alkyloxycarbonyl, C$_{1-3}$-alkyloxy-C$_{1-2}$alkylcarbonylamino, C$_{1-3}$-alkyloxycarbonylamino, C$_{1-3}$-alkylaminocarbonylamino, C$_{1-5}$-alkylcarbonylamino, C$_{1-5}$-alkyl-sulphonylamino group, or
  if R$^4$ is linked to G, it may also denote a fluorine atom or a hydroxy, methoxy, C$_{3-5}$-alkenyl-oxy, C$_{2-5}$-alkyl-oxy, C$_{3-6}$-cycloalkyl-oxy, benzyloxy, C$_{1-5}$-alkylaminocarbonyloxy, di(C$_{1-5}$-alkyl)aminocarbonyloxy or a C$_{4-7}$-cycloalkyleneiminocarbonyloxy group,
  with the proviso that
    two heteroatoms selected from among oxygen and nitrogen are separated from one another by precisely one optionally substituted —CH$_2$ group,
  is excluded, and
R$^5$ denotes a hydrogen atom or a C$_{1-5}$ alkyl, allyl, benzyl or phenyl group, or if R$^5$ is linked to G, it may also denote a hydroxy or methoxy group, or
R$^4$ and R$^5$ if they are bound to the same carbon atom, may form together with the carbon atom a —C=O group, or a —CF$_2$— group, or
R$^4$ and R$^5$ if they are bound to the same carbon atom or to two adjacent carbon atoms, may form together with the carbon atom or atoms a 3-6-membered carbocyclic group,
  wherein four directly adjacent carbon chain members of these C$_{5-6}$-carbocyclic groups may together be replaced by a —O—CH$_2$—CH$_2$O group,
the tautomers, enantiomers, diastereomers, mixtures and salts thereof.

A 6th embodiment of the present invention encompasses those compounds of embodiments 1, 2, 3, 4 or 5, wherein
D denotes a substituted bicyclic ring system of formula (IIf)

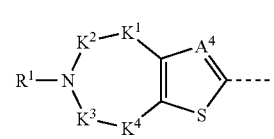

wherein
K$^1$ denotes a —CH$_2$, —CHR$^{7a}$, or a —CR$^{7b}$R$^{7c}$— group, and
K$^2$ and K$^3$
  each independently denote a —CH$_2$, —CHR$^{8a}$, or a —CR$^{8b}$R$^{8c}$— group, wherein
  R$^{8a}$/R$^{8b}$/R$^{8c}$ each independently denote a C$_{1-5}$-alkyl group, and $K^4$ denotes a bond, a —$CH_2$—, —$CHR^{7a}$—, or a —$CR^{7b}R^{7c}$— group, wherein
  $R^{7a}$ denotes a $C_{1-5}$-alkyl group, and
  $R^{7b}/R^{7c}$ each independently denote a hydroxy, $C_{1-5}$-alkyloxy or a $C_{1-5}$-alkyl group,
    wherein the two groups $R^{7b}/R^{7c}$ may not simultaneously be bound to the cyclic carbon atom via an oxygen atom,
and
in all, in formula (IIf) not more than four groups selected from among $R^{7a}$, $R^{7b}$, $R^{7c}$, $R^{8a}$, $R^{8b}$ and $R^{8c}$ may be present, and
$R^1$ denotes a hydrogen atom or a $C_{1-3}$-alkyl or cyclopropyl group, and wherein
$A^1$ denotes $CR^{10}$,
$A^2$ denotes $CR^{11}$,
$A^3$ denotes $CR^{12}$,
$A^4$ denotes either N or $CR^{12}$,
  wherein $R^{10}$, $R^{11}$ and $R^{12}$ 11 each independently denote a hydrogen, fluorine or chlorine atom, or a methyl, $CF_3$, hydroxy, methoxy, $CF_3O$, $CHF_2O$, $CH_2FO$ group,
the tautomers, enantiomers, diastereomers, mixtures and salts thereof.

A 7th embodiment of the present invention encompasses those compounds of embodiments 1, 2, 3, 4, 5 or 6, wherein M denotes a thiophen-2-yl ring of formula

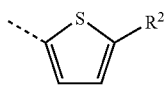

wherein
$R^2$ denotes a chlorine or bromine atom or an ethynyl group, the tautomers, enantiomers, diastereomers, mixtures and salts thereof.

An 8th embodiment of the present invention encompasses the following compounds:
(3R,5S)-5-chloro-thiophene-2-carboxylic acid-[4-hydroxymethyl-1-(6-methyl-4,5,6,7-tetrahydro-thieno[2,3-c]pyridine-2-carbonyl)-pyrrolidin-3-yl]-amide
(3R,5S)-5-chloro-thiophene-2-carboxylic acid-[5-methoxymethyl-1-(6-methyl-5,6,7,8-tetrahydro-4H-thieno[2,3-d]azepine-2-carbonyl)-pyrrolidin-3-yl]-amide
methyl (2S,4R)-4-[(5-chloro-thiophene-2-carbonyl)-amino]-1-(6-methyl-5,6,7,8-tetrahydro-4H-thieno[2,3-d]azepine-2-carbonyl)-pyrrolidine-2-carboxylate
methyl (2S,4R)-4-[(5-chloro-thiophene-2-carbonyl)-amino]-1-(4,6-dimethyl-5,6,7,8-tetrahydro-4H-thieno[2,3-d]azepine-2-carbonyl)-pyrrolidine-2-carboxylate
(2S,4R)-5-chloro-thiophene-2-carboxylic acid-[5-hydroxymethyl-1-(6-methyl-5,6,7,8-tetrahydro-4H-thieno[2,3-d]azepine-2-carbonyl)-pyrrolidin-3-yl]-amide
(3R,5S)-5-chloro-thiophene-2-carboxylic acid-{1-[(4SR)-4-methoxy-6-methyl-5,6,7,8-tetrahydro-4H-thieno[2,3-d]azepine-2-carbonyl]-4-methoxy-pyrrolidin-3-yl}-amide
(2S,4R)-4-[(5-chloro-thiophene-2-carbonyl)-amino]-1-(6-methyl-5,6,7,8-tetraydro-4H-thieno[2,3-d]azepine-2-carbonyl)-pyrrolidine-2-carboxylic acid-methylamide
4-[(5-chloro-thiophene-2-carbonyl)-amino]-1-(6-methyl-5,6,7,8-tetrahydro-4H-thieno[2,3-d]azepine-2-carbonyl)-pyrrolidin-2-yl-methyl (2S,4R)-ethyl-carbamate
(3R,5S)- 5-chloro-thiophene-2-carboxylic acid-[5-(methanesulphonylamino-methyl)-1-(6-methyl-5,6,7,8-tetrahydro-4H-thieno[2,3-d]azepine-2-carbonyl)-pyrrolidin-3-yl]-amide
(3R,5S)-5-chloro-thiophene-2-carboxylic acid-[5-[(3-ethyl-ureido)-methyl]-1-(6-methyl-5,6,7,8-tetrahydro-4H-thieno[2,3-d]azepine-2-carbonyl)-pyrrolidin-3-yl]-amide
methyl (2S,4R)-4-[(5-chloro-thiophene-2-carbonyl)-amino]-1-(6-methyl-5,6,7,8-tetrahydro-4H-thieno[2,3-d]azepine-2-carbonyl)-pyrrolidin-2-ylmethyl]-carbamate
(3R,5S)-5-chloro-thiophene-2-carboxylic acid-[5-[(2-methoxy-acetylamino)-methyl]-1-(6-methyl-5,6,7,8-tetrahydro-4H-thieno{[2,3-d]azepine-2-carbonyl}-pyrrolidin-3-yl)-amide
(2S,4R)-4-[(5-chloro-thiophene-2-carbonyl)-amino]-1-((S)-4-methoxy-6-methyl-5,6,7,8-tetrahydro-4H-thieno[2,3-d]azepine-2-carbonyl)-pyrrolidine-2-carboxylic acid methylamide
(3R,5S)-5-chloro-thiophene-2-carboxylic acid-[5-methoxymethyl-1-[(4S)-6-methyl-5,6,7,8-tetrahydro-4H-4-methoxy-thieno[2,3-d]azepine-2-carbonyl]-pyrrolidin-3-yl]-amide
(3R,5S)-5-chloro-thiophene-2-carboxylic acid-[5-(acetylamino-methyl)-1-(6-methyl-5,6,7,8-tetrahydro-4 H-thieno[2,3-d]azepine-2-carbonyl)-pyrrolidin-3-yl]-amide According to the invention the compounds of general formula (I) are obtained by methods known per se, for example by the following methods:

(a) The preparation of a compound of general formula (III)

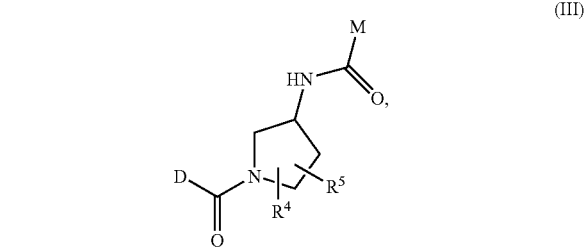

(III)

wherein D, M and $R^1$ to $R^5$ are defined as in embodiment 1,
  and which may optionally be protected at any amino, hydroxy, carboxy or thiol groups present by common protective groups such as for example those described in T. W. Greene, P.G.M. Wuts in "Protective Groups in Organic Synthesis", Wiley, 1991 and 1999, and the protective groups of which may be cleaved by the method known from the literature,
is described in the embodiments provided by way of example or may for example be carried out according to one of the following formula schemes 1 and 2 or analogously to the methods of synthesis described in WO2002/14308 or WO2006/114402.

Scheme 1

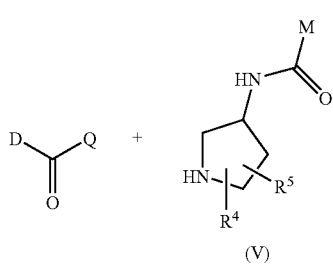

i) acylation

-continued

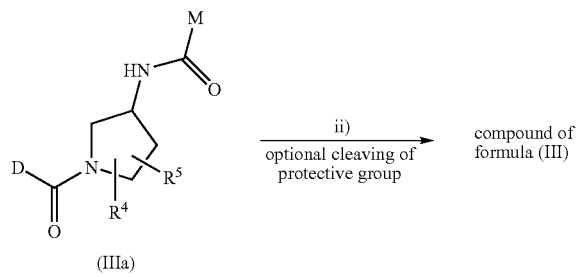

(IIIa)

Scheme 2

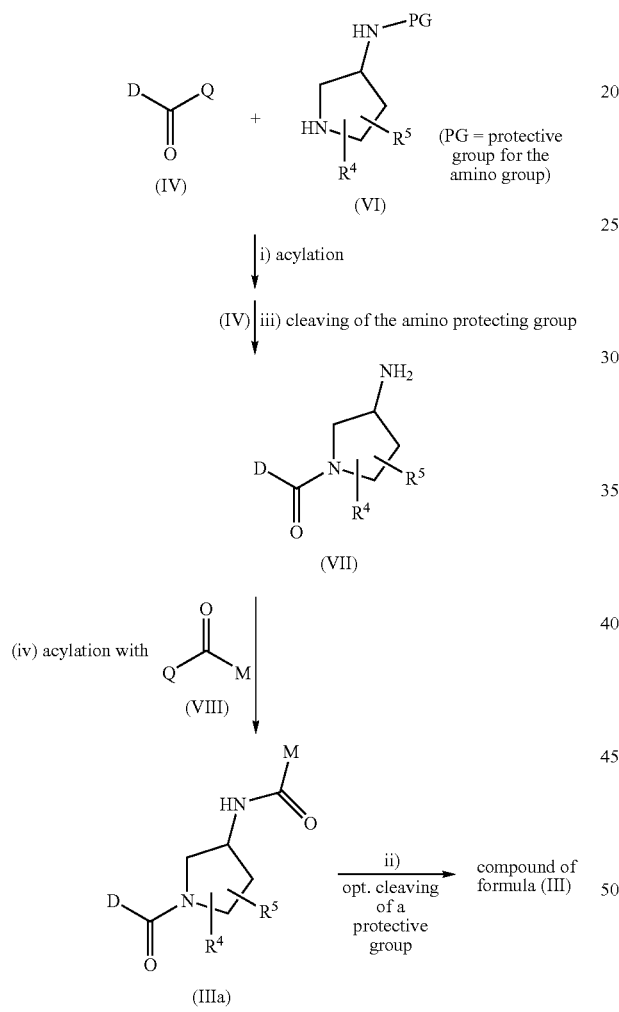

(IIIa)

wherein

Q denotes a leaving group or a group that can be converted in-situ into a leaving group, such as for example a halogen atom, a hydroxy, $C_{1-4}$-alkyloxy, alkyloxycarbonyloxy, pentafluorphenyloxy, 4-nitrophenyloxy, a trichloromethyl or acyloxy group, and PG denotes a protective group for the amino function known from the literature, such as for example a tert.-butoxycarbonyl, benzyloxycarbonyl or a trifluoroacetyl group.

The reaction steps i)-iv) shown in Schemes 1 and 2 may be carried out in the manner described in the Examples or according to the conditions known from the literature, for example as follows:

i) acylation of an amine (V) with an optionally activated carboxylic acid (IV) or (VIII):

The acylation is conveniently carried out with a corresponding halide or anhydride in a solvent such as methylene chloride, chloroform, carbon tetrachloride, ether, tetrahydrofuran, dioxane, benzene, toluene, acetonitrile, dimethylformamide, dimethylsulphoxide, sodium hydroxide solution or sulpholane, optionally in the presence of an inorganic or organic base at temperatures between −20 and 200° C., but preferably at temperatures between −10 and 100° C.

The acylation may however also be carried out with the free acid optionally in the presence of an acid-activating agent or a dehydrating agent, for example in the presence of ethyl-1-ethoxy-1,2-dihydroquinoline-1-carboxylate, isobutyl chloroformate, thionyl chloride, trimethylchlorosilane, hydrogen chloride, sulphuric acid, methanesulphonic acid, p-toluenesulphonic acid, phosphorus trichloride, phosphorus pentoxide, propanphosphonic acid cycloanhydride, N,N'-dicyclohexylcarbodiimide, N,N'-dicyclohexylcarbodiimide/camphorsulphonic acid, N,N'-dicyclohexylcarbodiimide/N-hydroxysuccinimide or 1-hydroxybenzotriazole, N,N'-carbonyldiimidazole, O-(benzotriazol-1-yl)-N,N,N',N'-tetramethyl-uronium tetrafluoroborate/N-methylmorpholine, O-(benzotriazol-1-yl)-N,N,N',N'-tetramethyl-uronium tetrafluoroborate/N-ethyldiisopropylamine, O-(7-azabenzotriazol-1-yl)-N,N,N', N'-tetramethyluronium-hexafluorophosphate/N-methylmorpholine, O-pentafluorophenyl-N,N,N',N'-tetramethyluronium-hexafluorophosphate/triethylamine, N,N'-thionyldiimidazole or triphenylphosphine/carbon tetrachloride, optionally with the addition of an auxiliary base such as sodium hydroxide solution, caesium, potassium or sodium carbonate or hydrogen carbonate or an amine base such as pyridine, triethylamine, N-methylmorpholine or diisopropylethylamine at temperatures between −20 and 200° C., but preferably at temperatures between −10 and 160° C.

Other methods of amide coupling are described for example in P. D. Bailey, I. D. Collier, K. M. Morgan in "Comprehensive Functional Group Interconversions", Vol. 5, page 257ff., Pergamon 1995, or in the Houben-Weyl Supplementary Volume 22, published by Thieme, 2003, and the literature cited therein.

ii) and iii) Cleaving a protective group

Any protecting group used may optionally subsequently be cleaved for example by hydrolysis in an aqueous solvent, e.g. in water, isopropanol/water, tetrahydrofuran/water or dioxane/water, in the presence of an acid such as trifluoroacetic acid, hydrochloric acid or sulphuric acid or in the presence of an alkali metal base such as lithium hydroxide, sodium hydroxide or potassium hydroxide or by ether splitting, e.g. in the presence of iodotrimethylsilane, at temperatures between 0 and 100° C., preferably at temperatures between 10 and 50° C.

However, a benzyl, methoxybenzyl or benzyloxycarbonyl group is cleaved hydrogenolytically, for example, e.g. with hydrogen in the presence of a catalyst such as palladium/charcoal in a solvent such as tetrahydrofuran, methanol, ethanol, ethyl acetate, dimethylformamide, dimethylformamide/acetone or glacial acetic acid, optionally with the addition of an acid such as hydrochloric acid at temperatures between 0 and 50° C., but preferably at ambient temperature, and at a hydrogen pressure of 1 to 7 bar, preferably, however, 1 to 5 bar.

However, a protective group may also be cleaved by the methods described by T. W. Greene, P.G.M. Wuts in "Protective Groups in Organic Synthesis", Wiley, 1991 and 1999.

(b) The components of general formula

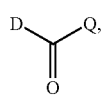

(IV)

wherein Q denotes a hydroxy or alkyloxy group, and wherein D are defined as in embodiment 1, and which may optionally be protected at any amino, hydroxy, carboxy or thiol groups present by common protective groups, such as for example those described in T. W. Greene, P.G.M. Wuts in "Protective Groups in Organic Synthesis", Wiley, 1991 and 1999, and the protective groups of which can be cleaved by methods known from the literature in the course of the synthesis sequence to produce compounds of formula (I), are known from the literature, or their synthesis is described in the embodiments by way of example, or they may be prepared for example using methods of synthesis known from the literature or analogously to methods of synthesis known from the literature, as described for example in DE3105858, JP04046139 or in N. Haginoya et al. J. Med. Chem. 2004, 47(21), 5167, S. Komoriya et al. Bioorg. Med. Chem. 2006, 14, 1309, Ortar et al. Tetrahedron Lett. 1986, 3931 or in J. M. Herbert et al., Tetrahedron. Lett 1998, 2421.

For example, a compound of general formula (IV), wherein D are defined as in embodiment 1, may be prepared as follows by palladium-mediated carboxylation in alcohols or water from compounds of general formulae (X) or (Xa)

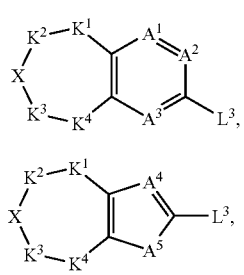

(X)

(Xa)

wherein $L^3$ denotes a leaving group or a group that can be converted in-situ into a leaving group, such as for example a halogen atom or a trifluoromethanesulphonate, and wherein $A^1$, $A^2$, $A^3$, $A^4$, $A^5$, $K^1$, $K^2$, $K^3$, $K^4$ and X are defined as in embodiment 1.

The introduction of an ester group from compounds of general formulae (X) or (Xa) is for example conveniently carried out with an alcohol by catalytic carbonylation with carbon monoxide, for example under a pressure of between 0.5 and 100 bar, but preferably between 1 and 50 bar, conveniently in the presence of a catalyst such as for example palladium(II)acetate,tetrakis(triphenylphosphine)palladium(0) or dichlorobis(triphenylphosphine)palladium(II), conveniently in a solvent or mixture of solvents such as water, methanol, ethanol, isopropanol, butanol, pentan, hexane, cyclohexane, heptane, benzene, toluene, xylene, ethyl acetate, methylpropionate, glycol, glycoldimethylether, diethylenegly-coldimethylether, dioxane, tetrahydrofuran, for example at temperatures between −30 and 250° C., but preferably between 0 and 150° C.

(c) The components of general formula

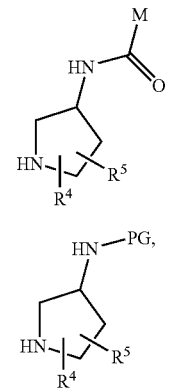

(V)

(VI)

wherein M, $R^4$ and $R^5$ are defined as in embodiment 1, are known in the literature, or their synthesis is described in the embodiments provided by way of example, or they may be prepared, for example, using methods of synthesis known in the literature or analogously to methods of synthesis known in the literature, as described for example in WO2006/114402.

In the reactions described above any reactive groups present such as hydroxy, carboxy, amino, alkylamino or imino groups may be protected during the reaction by conventional protecting groups which are cleaved again after the reaction.

For example, a suitable protecting group for a hydroxy group may be the methoxy, benzyloxy, trimethylsilyl, acetyl, benzoyl, tert.butyl, trityl, benzyl or tetrahydropyranyl group.

Suitable protecting groups for a carboxyl group might be the trimethylsilyl, methyl, ethyl, tert.butyl, benzyl or tetrahydropyranyl group.

Suitable protecting groups for an amino, alkylamino or imino group might be the acetyl, trifluoroacetyl, benzoyl, ethoxycarbonyl, tert.butoxycarbonyl, benzyloxycarbonyl, benzyl, methoxybenzyl or 2,4-dimethoxybenzyl group and additionally, for the amino group, the phthalyl group.

For example, a suitable protective group for an ethynyl group may be a trimethylsilyl, diphenylmethylsilyl, tert.butyldimethylsilyl or a 1-hydroxy-1-methyl-ethyl group.

Other protective groups which may be used and their cleaving are described in T. W. Greene, P.G.M. Wuts, "Protective Groups in Organic Synthesis", Wiley, 1991 and 1999.

Any protective group used may optionally subsequently be cleaved for example by hydrolysis in an aqueous solvent, e.g. in water, isopropanol/water, tetrahydrofuran/water or dioxane/water, in the presence of an acid such as trifluoroacetic acid, hydrochloric acid or sulphuric acid or in the presence of an alkali metal base such as lithium hydroxide, sodium hydroxide or potassium hydroxide or by ether splitting, e.g. in the presence of iodotrimethylsilane, at temperatures between 0 and 100° C., preferably at temperatures between 10 and 50° C.

However, a benzyl, methoxybenzyl or benzyloxycarbonyl group is cleaved hydrogenolytically, for example, e.g. with hydrogen in the presence of a catalyst such as palladium/charcoal in a solvent such as methanol, ethanol, ethyl acetate, dimethylformamide, dimethylformamide/acetone or glacial acetic acid, optionally with the addition of an acid such as hydrochloric acid at temperatures between 0 and 50° C., but preferably at ambient temperature, and at a hydrogen pressure of 1 to 7 bar, preferably, however, 1 to 5 bar.

A methoxybenzyl group may also be cleaved in the presence of an oxidising agent such as cerium(IV)ammonium nitrate in a solvent such as methylene chloride, acetonitrile or acetonitrile/water at temperatures of between 0 and 50° C., but preferably at ambient temperature.

A methoxy group is expediently cleaved in the presence of boron tribromide in a solvent such as methylene chloride at temperatures between −35 and −25° C.

A 2,4-dimethoxybenzyl group is preferably cleaved in trifluoroacetic acid in the presence of anisol.

A tert.butyl or tert.butyloxycarbonyl group is preferably cleaved by treating with an acid such as trifluoroacetic acid or hydrochloric acid, optionally using a solvent such as methylene chloride, dioxane or ether.

A phthalyl group is preferably cleaved in the presence of hydrazine or a primary amine such as methylamine, ethylamine or n-butylamine in a solvent such as methanol, ethanol, isopropanol, toluene/water or dioxane at temperatures between 20 and 50° C.

An allyloxycarbonyl group is cleaved by treating with a catalytic amount of tetrakis-(triphenylphosphine)-palladium (0), preferably in a solvent such as tetrahydrofuran and preferably in the presence of an excess of a base such as morpholine or 1,3-dimedone at temperatures between 0 and 100° C., preferably at ambient temperature and under an inert gas, or by treating with a catalytic amount of tris-(triphenylphosphine)-rhodium(I)chloride in a solvent such as aqueous ethanol and optionally in the presence of a base such as 1,4-diazabicyclo[2.2.2]octane at temperatures between 20 and 70° C.

Moreover the compounds of general formula (I) obtained may be resolved into their enantiomers and/or diastereomers.

Thus, for example, the compounds of general formula I obtained which occur as racemates may be separated by methods known per se (cf. Allinger N. L. And Eliel E. L. in "Topics in Stereochemistry", Vol. 6, Wiley Interscience, 1971) into their optical antipodes and compounds of general formula I with at least 2 asymmetric carbon atoms may be resolved into their diastereomers on the basis of their physical-chemical differences using methods known per se, e.g. by chromatography and/or fractional crystallisation, and, if these compounds are obtained in racemic form, they may subsequently be resolved into the enantiomers as mentioned above.

The enantiomers are preferably separated by column separation on chiral phases or by recrystallisation from an optically active solvent or by reacting with an optically active substance which forms salts or derivatives such as e.g. Esters or amides with the racemic compound, particularly acids and the activated derivatives or alcohols thereof, and separating the diastereomeric mixture of salts or derivatives thus obtained, e.g. on the basis of their differences in solubility, whilst the free antipodes may be released from the pure diastereomeric salts or derivatives by the action of suitable agents. Optically active acids in common use are e.g. the D- and L-forms of tartaric acid or dibenzoyltartaric acid, di-o-tolyltartaric acid, malic acid, mandelic acid, camphorsulphonic acid, glutamic acid, aspartic acid or quinic acid. An optically active alcohol may be for example (+) or (−)-menthol and an optically active acyl group in amides may be a (+)- or (−)-menthyloxycarbonyl, for example.

Furthermore, the compounds of formula I may be converted into the salts thereof, particularly for pharmaceutical use into the physiologically acceptable salts thereof with inorganic or organic acids. Acids which may be used for this purpose include for example hydrochloric acid, hydrobromic acid, sulphuric acid, methanesulphonic acid, phosphoric acid, fumaric acid, succinic acid, lactic acid, citric acid, tartaric acid or maleic acid.

Moreover, if the new compounds of formula I contain a carboxy group, they may subsequently, if desired, be converted into the salts thereof with inorganic or organic bases, particularly for pharmaceutical use into the physiologically acceptable salts thereof. Suitable bases for this purpose include for example sodium hydroxide, potassium hydroxide, cyclohexylamine, ethanolamine, diethanolamine and triethanolamine.

As already mentioned, the compounds of general formula I as well as the tautomers, the enantiomers, the diastereomers and the physiologically acceptable salts thereof have valuable pharmacological properties, particularly an antithrombotic activity, which is preferably based on an effect on thrombin or factor Xa, for example on a thrombin-inhibiting or factor Xa-inhibiting activity, on a prolonging effect on the aPTT time and on an inhibiting effect on related serine proteases such as e.g. urokinase, factor VIIa, factor IX, factor XI and factor XII.

The compounds listed in the experimental section may be investigated for their effect on the inhibition of factor Xa as follows:

Method:

Enzyme-kinetic measurement with chromogenic substrate. The quantity of p-nitroaniline (pNA) released from the colourless chromogenic substrate by human factor Xa is determined photometrically at 405 nm. It is proportional to the activity of the enzyme used. The inhibition of the enzyme activity by the test substance (in relation to the solvent control) is determined at various concentrations of test substance and from this the $IC_{50}$ is calculated, as the concentration which inhibits the factor Xa used by 50%.

Material:

Tris(hydroxymethyl)-aminomethane buffer (100 mMol) and sodium chloride (150 mMol), pH 8.0 plus 1 mg/ml Human Albumin Fraction V, protease-free.

Factor Xa (Calbiochem), spec. Activity: 217 IU/mg, final concentration: 7 IU/ml for each reaction mixture Substrate S 2765 (Chromogenix), final concentration: 0.3 mM/l (1 KM) for each reaction mixture Test substance: final concentration 100, 30, 10, 3, 1, 0.3, 0.1, 0.03, 0.01, 0.003, 0.001 µMol/l Procedure:

10 µl of a 23.5-times concentrated starting solution of the test substance or solvent (control), 175 µl of TRIS/HSA buffer and 25 µl of a 65.8 U/L Factor Xa working solution are incubated for 10 minutes at 37° C. After the addition of 25 µl of S 2765 working solution (2.82 mMol/l) the sample is measured in a photometer (SpectraMax 250) at 405 nm for 600 seconds at 37° C.

Evaluation:
1. Determining the maximum increase (deltaOD/minutes) over 21 measuring points.
2. Determining the % inhibition based on the solvent control.
3. Plotting a dosage/activity curve (% inhibition vs substance concentration).
4. Determining the $IC_{50}$ by interpolating the X-value (substance concentration) of the dosage/activity curve at Y=50% inhibition.

All the compounds tested had an $IC_{50}$ value of less than 100 µmol/L.

The compounds prepared according to the invention are generally well tolerated.

In view of their pharmacological properties the new compounds and the physiologically acceptable salts thereof are suitable for the prevention and treatment of venous and arterial thrombotic diseases, such as for example the prevention and treatment of deep leg vein thrombosis, thrombophlebitis, for preventing reocclusions after bypass operations or angioplasty (PT(C)A), and occlusion in peripheral arterial diseases, and for preventing and treating pulmonary embolism, disseminated intravascular coagulation and severe sepsis, for preventing and treating DVT in patients with exacerbation of COPD, for treating ulcerative colitis, for treating and preventing coronary thrombosis, for preventing stroke and the occlusion of shunts.

In addition, the compounds according to the invention are suitable for antithrombotic support in thrombolytic treatment, such as for example with alteplase, reteplase, tenecteplase, staphylokinase or streptokinase, for preventing long-term restenosis after PT(C)A, for the prevention and treatment of ischaemic events in patients with all forms of coronary heart disease, for preventing metastasis and the growth of tumours and inflammatory processes, e.g. in the treatment of pulmonary fibrosis, for preventing and treating rheumatoid arthritis, for preventing and treating fibrin-dependent tissue adhesions and/or the formation of scar tissue and for promoting wound healing processes.

The compounds specified may also be used as anticoagulants in connection with the preparation, storage, fractionation or use of whole blood or in invasive therapies, e.g. for coating prostheses, artificial heart valves and catheters for reducing the risk of thrombosis.

In view of their pharmacological properties the new compounds and the physiologically acceptable salts thereof are also suitable for treating Alzheimer's and Parkinson's disease. One rationale for this can be seen for example in the following findings, from which it can be concluded that thrombin inhibitors or factor Xa inhibitors, by inhibiting thrombin formation or activity, could be valuable drugs for treating Alzheimer's and Parkinson's disease. Clinical and experimental studies indicate that neurotoxic mechanisms, for example the inflammation that accompanies the activation of proteases of the clotting cascade, are involved in the dying off of neurones following brain damage. Various studies indicate an involvement of thrombin in neurodegenerative processes, e.g. following a stroke, repeated bypass operations or traumatic brain injury. An increased thrombin activity was able to be detected for example some days after peripoheral nerve damage. It was also shown that thrombin causes neurite retraction and glia proliferation, and apoptosis in primary cultures of neurones and neuroblastoma cells (for an overview see: *Neurobiol. Aging*, 2004, 25(6), 783-793). In addition, various in vitro studies on the brains of patients with Alzheimer's disease indicate that thrombin plays a part in the pathogenesis of this disease (*Neurosci. Lett.*, 1992, 146, 152-54). An accumulation of immunoreactive thrombin has been detected in neurite plaques in the brains of Alzheimer's patients. It was demonstrated in vitro that thrombin also plays a part in the regulation and stimulation of the production of Amyloid Precursor Protein (APP) as well as in the cleaving of APP into fragments which can be detected in the amyloid plaques in the brains of Alzheimer's patients. It has also been shown that thrombin-induced microglial activation in vivo leads to the degeneration of nigral dopaminergic neurones. These findings lead one to conclude that microglial activation, triggered by endogenous substance(s) such as thrombin, for example, are involved in the neuropathological process of the cell death of dopaminergic neurones, such as occurs in patients with Parkinson's disease (*J. Neurosci.*, 2003, 23, 5877-86).

The new compounds and the physiologically acceptable salts thereof can also be used for the prevention and treatment of arterial vascular diseases in combination therapy with lipid-lowering active substances such as HMG-CoA reductase inhibitors and vasodilators, particularly ACE inhibitors, angiotensin II antagonists, renin inhibitors, β-receptor antagonists, α-receptor antagonists, diuretics, Ca-channel blockers, or stimulators of soluble guanylate cyclase.

By increasing the antithrombotic activity the new compounds and the physiologically acceptable salts thereof can also be used in combination therapy with other anticoagulants such as, for example, unfractionated heparin, low-molecular heparin, fondaparinux or direct thrombin inhibitors, for example recombinant hirudine or "active-site" thrombin inhibitors.

The new compounds and the physiologically acceptable salts thereof may be used therapeutically in conjunction with acetylsalicylic acid, with inhibitors of platelet aggregation such as fibrinogen receptor antagonists (e.g. abciximab, eptifibatide, tirofiban, roxifiban), with physiological activators and inhibitors of the clotting system and the recombinant analogues thereof (e.g. Protein C, TFPI, antithrombin), with inhibitors of ADP-induced aggregation (e.g. clopidogrel, prasugrel, ticlopidine), with $P_2T$ receptor antagonists (e.g. cangrelor) or with combined thromboxane receptor antagonists/synthetase inhibitors (e.g. terbogrel).

The dosage required to achieve such an effect is appropriately 0.01 to 3 mg/kg, preferably 0.03 to 1.0 mg/kg by intravenous route, and 0.03 to 30 mg/kg, preferably 0.1 to 10 mg/kg by oral route, in each case administered 1 to 4 times a day.

For this purpose, the compounds of formula I prepared according to the invention may be formulated, optionally together with other active substances, with one or more inert conventional carriers and/or diluents, e.g. with corn starch, lactose, glucose, microcrystalline cellulose, magnesium stearate, polyvinylpyrrolidone, citric acid, tartaric acid, water, water/ethanol, water/glycerol, water/sorbitol, water/polyethylene glycol, propylene glycol, cetylstearyl alcohol, carboxymethylcellulose or fatty substances such as hard fat or suitable mixtures thereof, to produce conventional galenic preparations such as plain or coated tablets, capsules, powders, suspensions or suppositories.

The new compounds and the physiologically acceptable salts thereof may be used therapeutically in conjunction with acetylsalicylic acid, with inhibitors of platelet aggregation such as fibrinogen receptor antagonists (e.g. abciximab, eptifibatide, tirofiban, roxifiban), with physiological activators and inhibitors of the clotting system and the recombinant analogues thereof (e.g. Protein C, TFPI, antithrombin), with inhibitors of ADP-induced aggregation (e.g. clopidogrel, ticlopidine), with $P_2T$ receptor antagonists (e.g. cangrelor) or with combined thromboxane receptor antagonists/synthetase inhibitors (e.g. terbogrel).

EXPERIMENTAL SECTION

The following Examples are intended to illustrate the invention, without restricting its scope.

As a rule, melting points and/or IR, UV, $^1$H-NMR and/or mass spectra have been obtained for the compounds prepared. Unless otherwise stated, $R_f$ values were obtained using ready-made silica gel 60 $F_{254}$ TLC plates (E. Merck, Darmstadt, Item no. 1.05714) without chamber saturation. The $R_f$ values obtained under the name Alox were determined using ready-made aluminium oxide 60 $F_{254}$ TLC plates (E. Merck, Darmstadt, Item no. 1.05713) without chamber saturation. The $R_f$ values obtained under the name Reversed-phase-8 were determined using ready-made RP-8 $_{F254s}$ TLC plates (E. Merck, Darmstadt, Item no. 1.15684) without chamber saturation. The ratios given for the eluants refer to units by volume of the solvents in question. Chromatographic purification was done using silica gel supplied by Messrs Millipore (MATREX™, 35-70 µm). If the configuration is not specified in detail, it is unclear whether the compound in question is a pure stereoisomer or a mixture of enantiomer and diastereomer.

The HPLC-MS data were obtained under the following conditions:

Method A:
Waters Alliance 2695, Waters Micromass ZQ mass spectrometer with diode array detector 2996.
The mobile phase used was:
A: water with 0.13% TFA
B: acetonitrile

| time in min | % A | % B | flow rate in ml/min |
| --- | --- | --- | --- |
| 0.00 | 95 | 5 | 6.00 |
| 0.01 | 95 | 5 | 6.00 |
| 0.89 | 2 | 98 | 6.00 |
| 0.90 | 2 | 98 | 6.00 |
| 0.95 | 95 | 5 | 6.00 |
| 1.05 | 95 | 5 | 6.00 |
| 1.10 | 95 | 5 | 0.10 |

The stationary phase used was a Varian MS 100 C18 column, 3 µm, 4.6 mm×30 mm.

Method B:
Waters Alliance 2695, Waters Micromass ZQ mass spectrometer with diode array detector 2996.
The mobile phase used was:
A: water with 0.13% TFA
B: acetonitrile

| time in min | % A | % B | flow rate in ml/min |
| --- | --- | --- | --- |
| 0.00 | 95 | 5 | 3.50 |
| 0.18 | 95 | 5 | 3.50 |
| 2.00 | 2 | 98 | 3.50 |
| 2.20 | 2 | 98 | 3.50 |
| 2.30 | 95 | 5 | 3.50 |
| 2.50 | 95 | 5 | 3.50 |
| 2.60 | 95 | 5 | 0.10 |

The stationary phase used was a Varian MS 100 C18 column, 3 µm, 4.6 mm×30 mm.

The diode array detection was carried out in the wavelength range 210-380 nm.

Method C:
Waters Alliance 2695, Waters Micromass ZQ mass spectrometer with diode array detector 2996.
The mobile phase used was:
A: water with 0.1% ammonia
B: acetonitrile

| time in min | % A | % B | flow rate in ml/min |
| --- | --- | --- | --- |
| 0.00 | 95 | 5 | 4.00 |
| 0.01 | 95 | 5 | 4.00 |
| 0.89 | 2 | 98 | 4.00 |
| 0.90 | 2 | 98 | 4.00 |
| 0.95 | 95 | 5 | 4.00 |
| 1.05 | 95 | 5 | 4.00 |
| 1.10 | 95 | 5 | 0.10 |

The stationary phase used was a Waters Xbridge C18 column, 3.5 µm, 4.6 mm×20 mm.

The diode array detection was carried out in the wavelength range 210-380 nm.

Method D:
Waters Alliance 2695, Waters Micromass ZQ mass spectrometer with diode array detector 2996.
The mobile phase used was:
A: water with 0.13% trifluoroacetic acid
B: acetonitrile

| time in min | % A | % B | flow rate in ml/min |
| --- | --- | --- | --- |
| 0.00 | 100 | 0 | 5.00 |
| 0.08 | 100 | 0 | 5.00 |
| 1.70 | 0 | 100 | 5.00 |
| 1.75 | 0 | 100 | 5.00 |
| 1.80 | 100 | 0 | 5.00 |
| 1.85 | 100 | 0 | 5.00 |
| 1.90 | 100 | 0 | 0.10 |

The stationary phase used was a Varian Polaris C18 column, 3 µm, 4.6 mm×30 mm.

The diode array detection was carried out in the wavelength range 210-380 nm.

Method E:
Waters Alliance 2695, Waters Micromass ZQ mass spectrometer with diode array detector 2996.
The mobile phase used was:
A: water with 0.1% ammonia
B: acetonitrile

| time in min | % A | % B | flow rate in ml/min |
| --- | --- | --- | --- |
| 0.00 | 95 | 5 | 4.00 |
| 0.01 | 95 | 5 | 4.00 |
| 0.89 | 2 | 98 | 4.00 |
| 0.90 | 2 | 98 | 4.00 |
| 0.95 | 95 | 5 | 4.00 |
| 1.05 | 95 | 5 | 4.00 |
| 1.10 | 95 | 5 | 0.50 |

The stationary phase used was a Waters Xbridge C18 column, 3.5 µm, 4.6 mm×20 mm.

The diode array detection was carried out in the wavelength range 210-380 nm.

Method F:
Waters Alliance 2695, Waters Micromass ZQ mass spectrometer with diode array detector 2996.
The mobile phase used was:
A: water with 0.13% TFA
B: acetonitrile

| time in min | % A | % B | flow rate in ml/min |
|---|---|---|---|
| 0.00 | 95 | 5 | 3.50 |
| 0.18 | 95 | 5 | 3.50 |
| 2.00 | 2 | 98 | 3.50 |
| 2.20 | 2 | 98 | 3.50 |
| 2.30 | 95 | 5 | 3.50 |
| 2.50 | 95 | 5 | 3.50 |
| 2.60 | 95 | 5 | 0.50 |

The stationary phase used was a Varian MS 100 C18 column, 3 µm, 4.6 mm×30 mm.
The diode array detection was carried out in the wavelength range 210-380 nm.
Method G:
Waters Alliance 2695, Waters Micromass ZQ mass spectrometer with diode array detector 2996.
The mobile phase used was:
A: water with 0.1% ammonia
B: acetonitrile

| time in min | % A | % B | flow rate in ml/min |
|---|---|---|---|
| 0.00 | 95 | 5 | 4.00 |
| 0.01 | 95 | 5 | 4.00 |
| 0.89 | 2 | 98 | 4.00 |
| 0.90 | 2 | 98 | 4.00 |
| 0.95 | 95 | 5 | 4.00 |
| 1.05 | 95 | 5 | 4.00 |
| 1.10 | 95 | 5 | 0.50 |

The stationary phase used was a Waters Xbridge C18 column, 3.5 µm, 4.6 mm×20 mm.
The diode array detection was carried out in the wavelength range 210-380 nm.
Method H:
Waters Alliance 2695, Waters Micromass ZQ mass spectrometer with diode array detector 2996.
The mobile phase used was:
A: water with 0.13% ammonia
B: acetonitrile

| time in min | % A | % B | flow rate in ml/min |
|---|---|---|---|
| 0.00 | 95 | 5 | 5.00 |
| 0.01 | 95 | 5 | 5.00 |
| 1.80 | 2 | 98 | 5.00 |
| 1.90 | 2 | 98 | 5.00 |
| 2.00 | 95 | 5 | 5.00 |
| 2.10 | 95 | 5 | 5.00 |
| 2.15 | 95 | 5 | 0.50 |

The stationary phase used was a Varian Pursuit XRS 5 C18 column, 3 µm, 4.6 mm×30 mm.
The diode array detection was carried out in the wavelength range 210-380 nm.
The following abbreviations are used in the descriptions of the tests:
DCM dichloromethane
DIPEA N-ethyl-diisopropylamine
DMF N,N-dimethylformamide
EtOH ethanol
sat. saturated
h hour(s)
HATU O-(7-azabenzotriazol-1-yl)-N,N,N',N'-tetramethyluronium hexafluorophosphate
i. vac. in vacuo
conc. concentrated
min minute(s)
NMM N-methyl-morpholine
$R_f$ retention factor
$R_t$ retention time
TBTU O-(benzotriazol-1-yl)-N,N,N',N'-tetramethyluronium tetrafluoroborate
TEA triethylamine
TFA trifluoroacetic acid
THF tetrahydrofuran

EXAMPLE 1

5-Chloro-thiophene-2-carboxylic acid-[1-(3-methyl-2,3,4,5-tetrahydro-1H-benzo[d]azepine-7-carbonyl)-pyrrolidin-3-yl]-amide (as the trifluoroacetate salt)

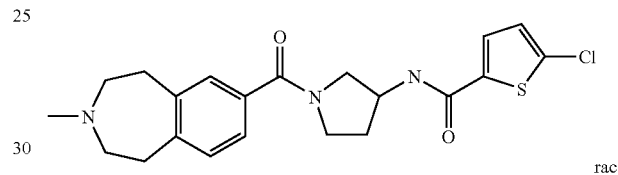

rac (a) tert. Butyl 3-[(5-chloro-thiophene-2-carbonyl)-amino]-pyrrolidine-1-carboxylate 0.5 g (2.7 mmol) tert. Butyl 3-amino-pyrrolidine-1-carboxylate are dissolved in 7 ml DCM, combined with 1.4 ml (10.1 mmol) TEA and 0.5 g (2.7 mmol) 5-chloro-thiophene-2-carboxylic acid chloride and stirred for one hour at RT. The reaction mixture is diluted with DCM and washed successively with dil. aqueous $KHSO_4$ solution, sat. aqueous NaHCO3 solution and water. The combined organic phases are dried on sodium sulphate and evaporated to dryness i. vac.
$R_t$ value: 0.65 min (Method A)
$C_{14}H_{19}ClN_2O_3S$ (330.83)
Mass spectrum: $(M+H)^+$ 32 329/331 (chlorine isotopes)
(b) 5-Chloro-thiophene-2-carboxylic acid-[1-(3-methyl-2,3,4,5-tetrahydro-1H-benzo[d]azepine-7-carbonyl)-pyrrolidin-3-yl]-amide (as the trifluoroacetate salt)

150 mg (453 mmol) tert. Butyl 3-[(5-chloro-thiophene-2-carbonyl)-amino]-pyrrolidine-1-carboxylate are stirred in a mixture of DCM/TFA (v/v 1:1) at RT for 30 min. Then 1 ml (76 mmol) TEA is added dropwise, so that the mixture has an alkaline reaction.

In another reaction vessel 110 mg (455 mmol) 3-methyl-2,3,4,5-tetrahydro-1H-benzo[d]azepine-7-carboxylic acid-hydrochloride are placed in 5 ml DCM and combined successively with 0.3 ml (2.3 mmol) TEA and 0.2 g (0.5 mmol) TBTU.

This reaction mixture is stirred for 20 min at RT, then added to the amine solution prepared earlier and stirred for 72 hours.

The reaction mixture is evaporated down i. vac., and the residue is acidified with TFA and purified by RP-HPLC.
$R_t$ value: 1.16 min (Method B)
$C_{21}H_{24}ClN_2O_3S \times CF_3CO_2H$ (417.96)
Mass spectrum: $(M+H)^+$=418/420 (chlorine isotopes)

The following compounds may be prepared analogously:

| N°. | Structural formula / Name | Mass peaks(s) | $R_f$ value or $R_t$ |
|---|---|---|---|
| 2 | 5-chloro-thiophene-2-carboxylic acid-[1-(2-methyl-1,2,3,4-tetrahydro-isoquinoline-6-carbonyl)-pyrrolidin-3-yl]-amide (as the trifluoroacetate salt) | $(M + H)^+ = 404/406$ (chlorine isotopes) | $R_t$ value = 0.44 min (Method A) |
| 3 | 5-chloro-thiophene-2-carboxylic acid-[1-(2-methyl-1,2,3,4-tetrahydro-isoquinolin-7-carbonyl)-pyrrolidin-3-yl]-amide (as the trifluoroacetate salt) | $(M + H)^+ = 404/406$ (chlorine isotopes) | $R_t$ value = 0.44 min (Method A) |
| 4 | ethyl (3RS,4RS)-4-[(5-chloro-thiophene-2-carbonyl)-amino]-1-(2-methyl-1,2,3,4-tetrahydro-isoquinoline-6-carbonyl)-pyrrolidine-3-carboxylate (as the trifluoroacetate salt) | $(M + H)^+ = 476/478$ (chlorine isotopes) | $R_t$ value = 1.25 min (Method B) |
| 5 | ethyl (3RS,4RS)-4[(5-chloro-thiophene-2-carbonyl)-amino]-1-(3-methyl-2,3,4,5-tetrahydro-1H-benzo[d]azepine-7-carbonyl)-pyrrolidine-3-carboxylate (as the trifluoroacetate salt) | $(M + H)^+ = 490/492$ (chlorine isotopes) | $R_t$ value = 1.29 min (Method B) |
| 8 | (R)-5-chloro-thiophene-2-carboxylic acid-[1-(2-methyl-1,2,3,4-tetrahydro-isoquinoline-6-carbonyl)-pyrrolidin-3-yl]-amide (as the trifluoroacetate salt) | $(M + H)^+ = 404/406$ (chlorine isotopes) | $R_t$ value = 1.14 min (Method B) |
| 9 | (S)-5-chloro-thiophene-2-carboxylic acid-[1-(3-methyl-2,3,4,5-tetrahydro-1H-benzo[d]azepine-7-carbonyl)-pyrrolidin-3-yl]-amide (as the trifluoroacetate salt) | $(M + H)^+ = 418/420$ (chlorine isotopes) | $R_t$ value = 1.14 min (Method B) |
| 10 | (R)-5-chloro-thiophene-2-carboxylic acid-[1-(3-methyl-2,3,4,5-tetrahydro-1H-benzo[d]azepine-7-carbonyl)-pyrrolidin-3-yl]-amide (as the trifluoroacetate salt) | $(M + H)^+ = 418/420$ (chlorine isotopes) | $R_t$ value = 1.17 min (Method B) |

-continued

| N°. | Structural formula / Name | Mass peaks(s) | $R_f$ value or $R_t$ |
|---|---|---|---|
| 11 | 5-bromo-thiophene-2-carboxylic acid-[1-(3-methyl-2,3,4,5-tetrahydro-1H-benzo[d]azepine-7-carbonyl)-pyrrolidin-3-yl]-amide (as the trifluoroacetate salt) | $(M + H)^+$ = 462/464 (bromine isotopes) | $R_t$ value = 1.15 min (Method B) |
| 12 | 5-bromo-thiophene-2-carboxylic acid-[1-(2-methyl-1,2,3,4-tetrahydro-isoquinoline-6-carbonyl)-pyrrolidin-3-yl]-amide (as the trifluoroacetate salt) | $(M + H)^+$ = 448/450 (bromine isotopes) | $R_t$ value = 1.13 min (Method B) |
| 13 | (S)-5-chloro-thiophene-2-carboxylic acid-[1-(2-methyl-1,2,3,4-tetrahydro-isoquinoline-6-carbonyl)-pyrrolidin-3-yl]-amide (as the trifluoroacetate salt) | $(M + H)^+$ = 404/406 (chlorine isotopes) | $R_t$ value = 1.14 min (Method B) |
| 23 | (3SR,4SR)-5-chloro-thiophene-2-carboxylic acid-[4-hydroxy-1-(2-metyl-1,2,3,4-tetrahydro-isoquinoline-6-carbonyl)-pyrrolidin-3-yl]-amide (as the trifluoroacetate salt) | $(M + H)^+$ = 420/422 (chlorine isotopes) | $R_t$ value = 0.99 min (Method B) |
| 25 | (3SR,4SR)-5-chloro-thiophene-2-carboxylic acid-[4-hydroxy-1-(3-metyl-2,3,4,5-tetrahydro-1H-benzo[d]azepine-7-carbonyl)-pyrrolidin-3-yl]-amide (as the trifluoroacetate salt) | $(M + H)^+$ = 434/436 (chlorine isotopes) | $R_t$ value = 1.02 min (Method B) |
| 28 | (3RS,4SR)-5-chloro-thiophene-2-carboxylic acid-[1-(2-methyl-1,2,3,4-tetrahydro-isoquinoline-6-carbonyl)-4-phenyl-pyrrolidin-3-yl]-amide (as the trifluoroacetate salt) | $(M + H)^+$ = 480/482 (chlorine isotopes) | $R_t$ value = 1.32 min (Method B) |

| N°. | Structural formula Name | Mass peaks(s) | $R_f$ value or $R_t$ |
|---|---|---|---|
| 29 | ![structure] rac<br>(3RS,4SR)-5-chloro-thiophene-2-carboxylic acid-[1-(3-methyl-2,3,4,5-tetrahydro-1H-benzo[d]azepine-7-carbonyl)-4-phenyl-pyrrolidin-3-yl]-amide (as the trifluoroacetate salt) | $(M + H)^+ = 494/496$ (chlorine isotopes) | $R_t$ value = 1.36 min (Method B) |

EXAMPLE 6

(3RS,4RS)-4-[(Chloro-thiophene-2-carbonyl)-amino]-1-(2-methyl-1,2,3,4-tetrahydro-isoquinoline-6-carbonyl)-pyrrolidine-2-carboxylic acid (as the trifluoroacetate salt)

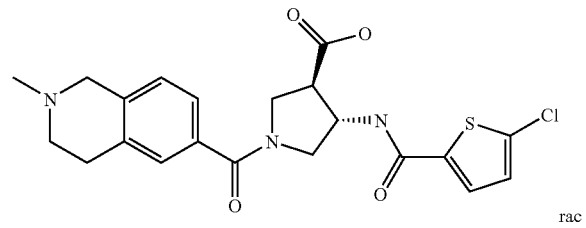

rac (a) (3SR,4RS)-4-[(chloro-thiophene-2-carbonyl)-amino]-1-(2-methyl-1,2,3,4-tetrahydro-isoquinoline-6-carbonyl)-pyrrolidine-2-carboxylic acid (as the trifluoroacetate salt)

14 mg (24 μmol) ethyl (3SR,4RS)-4-[(5-chloro-thiophene-2-carbonyl)-amino]-1-(2-methyl-1,2,3,4-tetrahydro-isoquinoline-6-carbonyl)-pyrrolidine-3-carboxylate (as the trifluoroacetate salt) are dissolved in 500 μL methanol, combined with 120 μL lithium hydroxide solution (8% in water) and stirred for 16 hours at RT. The mixture is concentrated i. vac. and the residue is purified by RP-HPLC.

$R_t$ value: 1.07 min (Method B)

$C_{21}H_{22}ClN_3O_4S \times CF_3CO_2H$ (447.94)

Mass spectrum: $(M+H)^+=448/450$ (chlorine isotopes)

The following compounds may be prepared analogously:

| N°. | Structural formula Name | Mass peak(s) | $R_f$ value or $R_t$ |
|---|---|---|---|
| 7 | ![structure] rac<br>(3SR,4RS)-4-[(5-chloro-thiophene-2-carbonyl)-amino]-1-(3-methyl-2,3,4,5-tetrahydro-1H-benzo[d]azepine-7-carbonyl)-pyrrolidine-3-carboxylic acid (as the trifluoroacetate salt) | $(M + H)^+ = 462/464$ (chlorine isotopes) | $R_t$ value = 1.10 min (Method B) |
| 21 | ![structure]<br>(2S,4R)-4-[(5-chloro-thiophene-2-carbonyl)-amino]-1-(3-methyl-2,3,4,5-tetrahydro-1H-benzo[d]azepine-7-carbonyl)-pyrrolidine-2-carboxylic acid (as the trifluoroacetate salt) | $(M + H)^+ = 462/464$ (chlorine isotopes) | $R_t$ value = 1.11 min (Method B) |

| N°. | Structural formula Name | Mass peak(s) | $R_f$ value or $R_t$ |
|---|---|---|---|
| 62 | (2S,4R)-4-[(5-chloro-thiophene-2-carbonyl)-amino]-1-(6-methyl-5,6,7,8-tetrahydro-4H-thieno[2,3-d]azepine-2-carbonyl)-pyrrolidine-2-carboxylic acid (as the trifluoroacetate salt) | (M + H)⁺ = 468/470 (chlorine isotopes) | $R_t$ value = 1.11 min (Method B) |
| 88 | (2S,4R)-4-[(5-chloro-thiophene-2-carbonyl)-amino]-1-(6-methyl-4,5,6,7-tetrahydro-thieno[2,3-c]pyridine-2-carbonyl)-pyrrolidine-2-carboxylic acid | (M + H)⁺ = 454/456 (chlorine isotopes) | $R_t$ value = 0.47 min (Method G) |

EXAMPLE 14

Methyl (2S,4R)-4-[(chloro-thiophene-2-carbonyl)-amino]-1-(3-methyl-2,3,4,5-tetrahydro-1H-benzo[d]azepine-7-carbonyl)-pyrrolidine-2-carboxylate (as the trifluoroacetate salt)

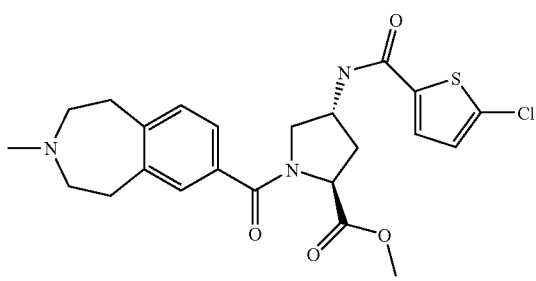

(a) 1-tert.-butyl-2-methyl (2S,4S)-methanesulphonyloxy-pyrrolidine-1,2-dicarboxylate 6.5 g (26.3 mmol) 1-tert.-butyl-2-methyl (2S,4S)-4-hydroxy-pyrrolidine-1,2-dicarboxylate are dissolved in 40 ml DCM and at 0° C. combined with 4.4 ml (31.7 mmol) TEA and 2.5 ml (32.2 mmol) methanesulphonic acid chloride. The mixture is stirred for 30 minutes at 0° C. and for two hours at RT. Then the mixture is poured onto water and the aqueous phase is extracted three times with DCM. The combined organic phases are dried on sodium sulphate and concentrated i. vac.

R value: 1.27 min (Method B)
$C_{12}H_{21}NO_7S$ (323.36)
Mass spectrum: (M+H)⁺=324

(b) 1-tert.-butyl-2-methyl (2S,4R)-azido-pyrrolidine-1,2-dicarboxylate 8.5 g (26.3 mmol) 1-tert.-butyl-2-methyl (2S,4S)-methanesulphonyloxy-pyrrolidine-1,2-dicarboxylate are dissolved in 25 ml DMF and combined at RT with 6.0 g (92.3 mmol) sodium azide. The mixture is stirred for 20 hours at 50° C. Then the reaction mixture is concentrated i. vac. and the residue is combined with ethyl acetate and water. The aqueous phase is extracted three times with ethyl acetate. The combined organic phases are dried on sodium sulphate and concentrated i. vac.

$R_t$ value: 1.38 min (Method B)
$C_{11}H_{18}N_4O_4$ (270.29)
Mass spectrum: (M+H)⁺=271

(c) 1-tert.-butyl-2-methyl (2S,4R)-amino-pyrrolidine-1,2-dicarboxylate 7.5 g (27.8 mmol) 1-tert.-butyl-2-methyl (2S,4R)-azido-pyrrolidine-1,2-dicarboxylate are dissolved in 15 ml of methanol, combined with 500 mg palladium/charcoal (10%) and hydrogenated for two days with 3 bar hydrogen. Then the mixture is filtered and evaporated down i. vac.

$R_t$ value: 0.91 min (Method B)
$C_{11}H_{20}N_2O_4$ (244.29)
Mass spectrum: (M+H)⁺=245

(d) 1-tert.-butyl-2-methyl (2S,4R)-4-[(5-chloro-thiophene-2-carbonyl)-amino]-pyrrolidine-1,2-dicarboxylate Prepared analogously to Example 1a from 1-tert.-butyl-2-methyl (2S,4R)-amino-pyrrolidine-1,2-dicarboxylate and 5-chloro-thiophene-2-carbonyl chloride.

$R_t$ value: 1.56 min (Method B)
$C_{11}H_{21}ClN_2O_5S$ (388.87)
Mass spectrum: (M−H)⁻=387/389 (chlorine isotopes)

(e) Methyl (2S,4R)-4-[(chloro-thiophene-2-carbonyl)-amino]-1-(3-methyl-2,3,4,5-tetrahydro-1H-benzo[d]azepine-7-carbonyl)-pyrrolidine-2-carboxylate (as the trifluoroacetate salt)

Prepared analogously to Example 1b from 1-tert.-butyl-2-methyl (2S,4R)-4-[(5-chloro-thiophene-2-carbonyl)-amino]-pyrrolidine-1,2-dicarboxylate and 3-methyl-2,3,4,5-tetrahydro-1H-benzo[d]azepine-7-carboxylic acid-hydrochloride.

$R_t$ value: 1.29 min (Method B)
$C_{23}H_{26}ClN_3O_4S \times CF_3CO_2H$ (476.00)
Mass spectrum: (M+H)⁺=476/478 (chlorine isotopes)

The following compounds may be prepared analogously:

| N°. | Structural formula / Name | Mass peak(s) | $R_f$ value or $R_t$ |
|---|---|---|---|
| 15 | methyl (2S,4R)-4-[(5-chloro-thiophene-2-carbonyl)-amino]-1-(2-methyl-1,2,3,4-tetrahydro-isoquinoline-6-carbonyl)-pyrrolidine-2-carboxylate (as the trifluoroacetate salt) | $(M+H)^+ = 462/464$ (chlorine isotopes) | $R_t$ value: 1.01 min (Method B) |
| 59 | methyl (2S,4R)-4-[(5-chloro-thiophene-2-carbonyl)-amino]-1-(6-methyl-5,6,7,8-tetrahydro-4H-thieno[2,3-d]azepine-2-carbonyl)-pyrrolidine-2-carboxylate | $(M+H)^+ = 482/484$ (chlorine isotopes) | $R_t$ value: 1.14 min (Method F) |
| 87 | methyl (2S,4R)-4-[(5-chloro-thiophene-2-carbonyl)-amino]-1-(6-methyl-4,5,6,7-tetrahydro-thieno[2,3-c]pyridine-2-carbonyl)-pyrrolidine-2-carboxylate | $(M+H)^+ = 468/470$ (chlorine isotopes) | $R_t$ value: 0.68 min (Method G) |

EXAMPLE 16

(2S,4R)-4-[(Chloro-thiophene-2-carbonyl)-amino]-1-(3-methyl-2,3,4,5-tetrahydro-1H-benzo[d]azepine-7-carbonyl)-pyrrolidine-2-carboxylic acid-dimethylamide (as the trifluoroacetate salt)

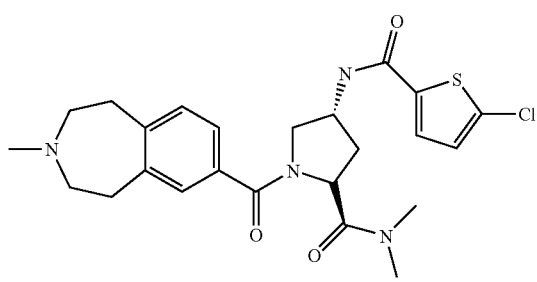

(a) tert. Butyl (2S,4R)-4-[(5-chloro-thiophene-2-carbonyl)-amino]-2-dimethylcarbamoyl-pyrrolidine-1-carboxylate 210 mg (2.6 mmol) dimethylamin-hydrochloride are dissolved in 5 ml DCM and combined with 3 ml trimethylaluminium solution (2M in toluene, 6 mmol). This mixture is stirred for 30 minutes, then a solution of 1.0 g (2.6 mmol) 1-tert.-butyl-2-methyl (2S,4R)-4-[(5-chloro-thiophene-2-carbonyl)-amino]-pyrrolidine-1,2-dicarboxylate in 5 ml DCM is added and the mixture is stirred for 16 hours at RT. Then a further 3 mmol dimethylaluminium-dimethylamide solution in DCM/toluene (prepared analogously) are added and the mixture is stirred for a further three days at RT. The mixture is diluted with 20 ml DCM and combined with a little water. This mixture is evaporated down i. vac. The residue is mixed with DCM and washed successively with water and 0.5 N sodium hydroxide solution. The organic phase is washed once with 0.5 N hydrochloric acid, dried on sodium sulphate and evaporated down i. vac.

$R_t$ value: 1.32 min (Method B)

$C_{17}H_{24}ClN_3O_4S$ (401.91)

Mass spectrum: $(M+H)^+ = 402/404$ (chlorine isotopes)

(b) Methyl (2S,4R)-4-[(chloro-thiophene-2-carbonyl)-amino]-1-(3-methyl-2,3,4,5-tetrahydro-1H-benzo[d]azepine-7-carbonyl)-pyrrolidine-2-carboxylate (as the trifluoroacetate salt)

Prepared analogously to Example 1b from tert. Butyl (2S,4R)-4-[(5-chloro-thiophene-2-carbonyl)-amino]-2-dimethylcarbamoyl-pyrrolidine-1-carboxylate and 3-methyl-2,3,4,5-tetrahydro-1H-benzo[d]azepine-7-carboxylic acid-hydrochloride.

$R_t$ value: 1.07 min (Method B)

$C_{24}H_{29}ClN_4O_3S \times CF_3CO_2H$ (489.04)

Mass spectrum: $(M+H)^+ = 489/491$ (chlorine isotopes)

The following compounds may be prepared analogously:

| N°. | Structural formula / Name | Mass peak(s) | $R_f$ value or $R_t$ |
|---|---|---|---|
| 17 | (2S,4R)-4-[(5-chloro-thiophene-2-carbonyl)-amino]-1-(2-methyl-1,2,3,4-tetrahydro-isoquinoline-6-carbonyl)-pyrrolidine-2-carboxylic acid-dimethylamide (as the trifluoroacetate salt) | $(M + H)^+ = 475/477$ (chlorine isotopes) | $R_t$ value: 1.05 min (Method B) |
| 33 | (2S,4R)-5-chloro-thiophene-2-carboxylic acid-[1-(3-methyl-2,3,4,5-tetrahydro-1H-benzo[d]azepine-7-carbonyl)-5-(morpholine-4-carbonyl)-pyrrolidin-3-yl]-amide (as the trifluoroacetate salt) | $(M + H)^+ = 531/533$ (chlorine isotopes) | $R_t$ value: 1.09 min (Method B) |
| 34 | (2S,4R)-5-chloro-thiophene-2-carboxylic acid-[2-methyl-1,2,3,4-tetrahydro-isoquinoline-6-carbonyl)-5-(morpholine-4-carbonyl)-pyrrolidin-3-yl]-amide (as the trifluoroacetate salt) | $(M + H)^+ = 517/519$ (chlorine isotopes) | $R_t$ value: 1.05 min (Method B) |
| 75 | (2S,4R)-4-[(5-chloro-thiophene-2-carbonyl)-amino]-1-(6-methyl-5,6,7,8-tetrahydro-4H-thieno[2,3-d]azepine-2-carbonyl)-pyrrolidine-2-carboxylic acid-methylamid (as the trifluoroacetate salt) | $(M + H)^+ = 481/483$ (chlorine isotopes) | $R_t$ value: 1.02 min (Method B) |
| 57 | (2S,4R)-4-[(5-chloro-thiophene-2-carbonyl)-amino]-1-[6-methyl-4,5,6,7,-tetrahydro-thieno[2,3-c]pyridine-2-carbonyl]-pyrrolidine-2-carboxylic acid-dimethylamide | $(M - H)^- = 479/481$ (chlorine isotopes) | $R_t$ value: 1.05 min (Method F) |

-continued

| N°. | Structural formula / Name | Mass peak(s) | $R_f$ value or $R_t$ |
|---|---|---|---|
| 58 | 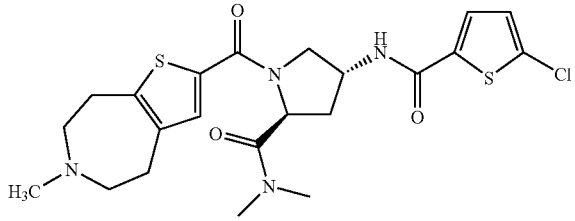<br>(2S,4R)-4-[(5-chloro-thiophene-2-carbonyl)-amino]-1-(6-methyl-5,6,7,8-tetraydro-4H-thieno[2,3-d]azepine-2-carbonyl)-pyrrolidine-2-carboxylic acid-dimethylamide | $(M + H)^+ = 495/497$ (chlorine isotopes) | |
| 78 | 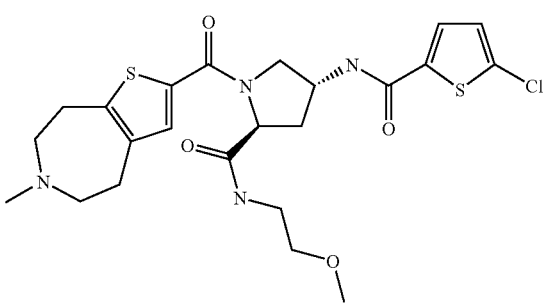<br>(2S,4R)-4-[(5-chloro-thiophene-2-carbonyl)-amino]-1-(6-methyl-5,6,7,8-tetraydro-4H-thieno[2,3-d]azepine-2-carbonyl)-pyrrolidine-2-carboxylic acid-(2-methoxy-ethyl)-amide | $(M + H)^+ = 525/527$ (chlorine isotopes) | $R_t$ value: 0.61 min (Method G) |
| 79 | 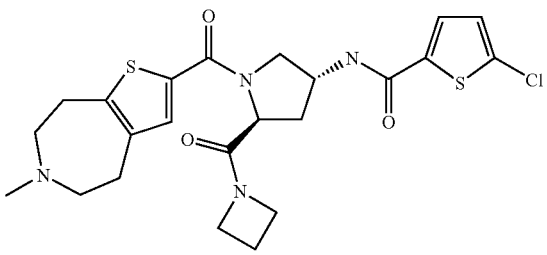<br>(3S,5R)-5-chloro-thiophene-2-carboxylic acid-[5-(azetidine-1-carbonyl)-1-(6-methyl-5,6,7,8-tetrahydro-4H-thieno[2,3-d]azepine-2-carbonyl)-pyrrolidin-3-yl]-amide | $(M + H)^+ = 507/509$ (chlorine isotopes) | $R_t$ value: 0.63 min (Method G) |
| 80 | 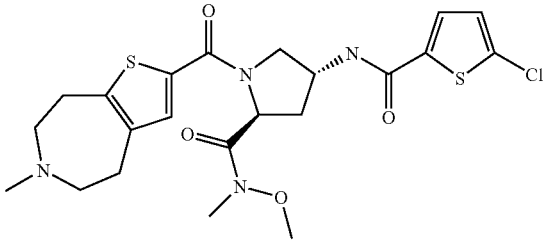<br>(2S,4R)-4-[(5-chloro-thiophene-2-carbonyl)-amino]-1-(6-methyl-5,6,7,8-tetraydro-4H-thieno[2,3-d]azepine-2-carbonyl)-pyrrolidine-2-carboxylic acid-methoxy-methyl-amide (as hydrochloride salt) | $(M + H)^+ = 511/513$ (chlorine isotopes) | $R_t$ value: 1.16 min (Method F) |

| N°. | Structural formula Name | Mass peak(s) | $R_f$ value or $R_t$ |
|---|---|---|---|
| 83 | (3S,5R)-5-chloro-thiophene-2-carboxylic acid-[1-(6-methyl-5,6,7,8-tetrahydro-4H-thieno[2,3-d]azepine-2-carbonyl)-5-pyrrolidine-1-carbonyl)-pyrrolidin-3-yl]-amide | $(M + H)^+ = 521/523$ (chlorine isotopes) | $R_t$ value: 1.15 min (Method F) |

EXAMPLE 19

(3RS,4SR)-5-Chloro-thiophene-2-carboxylic acid-[4-hydroxymethyl-1-(2-methyl-1,2,3,4-tetrahydro-isoquinoline-6-carbonyl)-pyrrolidin-3-yl]-amide (as the trifluoroacetate salt)

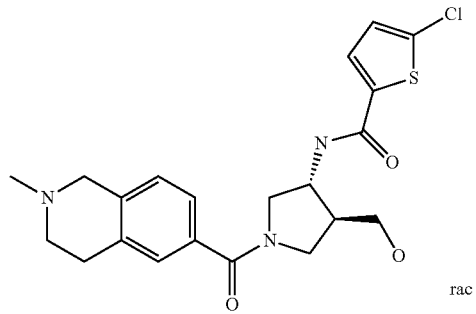

rac (a) tert. Butyl (3RS,4SR)-3-[(5-chloro-thiophene-2-carbonyl)-amino]-4-hydroxymethyl-pyrrolidine-1-carboxylate 168 mg (417 μmol) 1-tert.-butyl-3-ethyl (3RS,4RS)-4-[(5-chloro-thiophene-2-carbonyl)-amino]-pyrrolidine-1,3-dicarboxylate are dissolved in 4 ml THF, a total of 20 mg (872 μmol) lithium borohydride is added batchwise and the mixture is stirred for one hour at RT. Then the reaction mixture is poured into sat. sodium chloride solution and stirred. The aqueous phase is extracted three times with ethyl acetate, the combined organic phases are dried on sodium sulphate and evaporated to dryness i. vac.

$R_t$ value: 1.36 min (Method B)
$C_{15}H_{21}ClN_2O_4S$ (360.86)
Mass spectrum: $(M+H)^+=361/363$ (chlorine isotopes)

(b) (3RS,4SR)-5-chloro-thiophene-2-carboxylic acid-[4-hydroxymethyl-1-(2-methyl-1,2,3,4-tetrahydro-isoquinoline-6-carbonyl)-pyrrolidin-3-yl]-amide Prepared analogously to Example 1b from tert. Butyl (3RS,4RS)-3-[(5-chloro-thiophene-2-carbonyl)-amino]-4-hydroxymethyl-pyrrolidine-1-carboxylate and 2-methyl-1,2,3,4-tetrahydro-isoquinoline-6-carboxylic acid-hydrochloride.

$R_t$ value: 1.00 min (Method B)
$C_{21}H_{24}ClN_3O_3S$ (433.95)
Mass spectrum: $(M+H)^+=434/436$ (chlorine isotopes)

The following compounds may be prepared analogously:

| N°. | Structural formula Name | Mass peak(s) | $R_f$ value or $R_t$ |
|---|---|---|---|
| 18 | (2S,4R)-5-chloro-thiophene-2-carboxylic acid-[5-hydroxymethyl-1-(3-methyl-2,3,4,5-tetrahydro-1H-benzo[d]azepine-7-carbonyl)-pyrrolidin-3-yl]-amide | $(M + H)^+ = 448/450$ (chlorine isotopes) | $R_t$ value: 1.03 min (Method B) |
| 20 | (2S,4R)-5-chloro-thiophene-2-carboxylic acid-[5-hydroxymethyl-1-(2-methyl-1,2,3,4-tetrahydro-isoquinoline-6-carbonyl)-pyrrolidin-3-yl]-amide (as the trifluoroacetate salt) | $(M + H)^+ = 434/436$ (chlorine isotopes) | $R_t$ value: 1.00 min (Method B) |

| N°. | Structural formula Name | Mass peak(s) | $R_f$ value or $R_t$ |
|---|---|---|---|
| 63 | (2S,4R)-5-chloro-thiophene-2-carboxylic acid-[5-hydroxymethyl-1-(6-methyl-5,6,7,8-tetrahydro-4H-thiazolo[4,5-d]azepine-2-carbonyl)-pyrrolidin-3-yl]-amide (as the trifluoroacetate salt) | $(M + H)^+$ = 455/457 (chlorine isotopes) | $R_t$ value: 1.01 min (Method F) |
| 64 | (2S,4R)-5-chloro-thiophene-2-carboxylic acid-[5-hydroxymethyl-1-(5-methyl-4,5,6,7-tetrahydro-thiazolo[4,5-c]pyridine-2-carbonyl)-pyrrolidin-3-yl]-amide (as the trifluoroacetate salt) | $(M + H)^+$ = 441/443 (chlorine isotopes) | $R_t$ value: 1.01 min (Method F) |
| 66 | (2S,4R)-5-chloro-thiophene-2-carboxylic acid-[5-hydroxymethyl-1-(6-methyl-5,6,7,8-tetrahydro-4H-thieno[2,3-d]azepine-2-carbonyl)-pyrrolidin-3-yl]-amide (as the trifluoroacetate salt) | $(M - H)^-$ = 452/454 (chlorine isotopes) | $R_t$ value: 0.60 min (Method G) |

EXAMPLE 22

(3RS,4RS)-5-Chloro-thiophene-2-carboxylic acid-[4-methoxy-1-(2-methyl-1,2,3,4-tetrahydro-isoquinoline-6-carbonyl)-pyrrolidin-3-yl]-amide (as the trifluoroacetate salt)

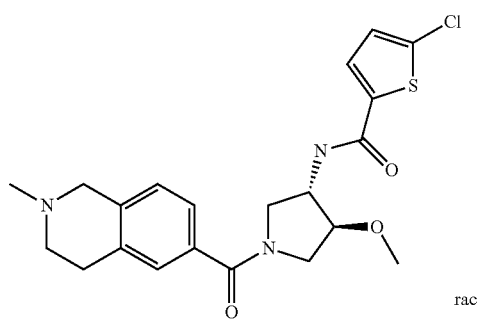

(a) tert. Butyl (3SR,4SR)-3-[(5-chloro-thiophene-2-carbonyl)-amino]-4-methoxy-pyrrolidine-1-carboxylate Prepared analogously to Example 1a from tert. Butyl (3SR,4SR)-3-amino-4-methoxy-pyrrolidine-1-carboxylate (prepared analogously to Y. Tsuzuki et al. *Tetrahedron Asymm.* 2001, 12, 2989) and 5-chlorothiophene-2-carbonyl chloride.

$R_t$ value: 1.36 min (Method B)

$C_{15}H_{21}ClN_2O_4S$ (360.86)

Mass spectrum: $(M+H)^+$=361/363 (chlorine isotopes)

(b) (3SR,4SR)-5-chloro-thiophene-2-carboxylic acid-[4-methoxy-1-(2-methyl-1,2,3,4-tetrahydro-isoquinoline-6-carbonyl)-pyrrolidin-3-yl]-amide (as the trifluoroacetate salt)

Prepared analogously to Example 1 b from tert. Butyl (3SR,4SR)-3-[(5-chloro-thiophene-2-carbonyl)-amino]-4-methoxy-pyrrolidine-1-carboxylate and 2-methyl-1,2,3,4-tetrahydro-isoquinoline-6-carboxylic acid-hydrochloride.

$R_t$ value: 1.11 min (Method B)

$C_{21}H_{24}ClN_3O_3S$ (433.96)

Mass spectrum: $(M+H)^+$=434/436 (chlorine isotopes)

The following compounds may be prepared analogously:

| N°. | Structural formula / Name | Mass peak(s) | $R_f$ value or $R_t$ |
|---|---|---|---|
| 24 | (3SR,4SR)-5-chloro-thiophene-2-carboxylic acid-[4-methoxy-1-(3-methyl-2,3,4,5-tetrahydro-1H-benzo[d]azepine-7-carbonyl)-pyrrolidin-3-yl]-amide (as the trifluoroacetate salt) | $(M + H)^+ = 448/450$ (chlorine isotopes) | $R_t$ value: 1.12 min (Method B) |

EXAMPLE 26

(2S,4R)-4-[(5-Chloro-thiophene-2-carbonyl)-amino]-1-[(3R)-2,3-dimethyl-1,2,3,4-tetrahydroiso-quinoline-6-carbonyl]-pyrrolidine-2-carboxylic acid-dimethylamide (as the trifluoroacetate salt)

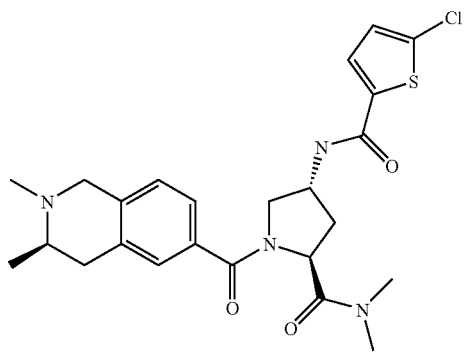

(a) ($S_s$,R)-2-methyl-propane-2-sulphinic acid-[2-(5-bromo-2-cyano-phenyl)-1-methyl-ethyl]-amide 6.0 ml (42.8 mmol) diisopropylamine are dissolved in 80 ml THF, slowly mixed with 26.7 ml (42.8 mmol) butyllithium solution (1.6 M in n-hexane) at 0° C. and stirred for 30 min. Then this solution is cooled to −78° C. and a solution of 4.0 g (20.4 mmol) 4-bromo-2-methyl-benzonitrile in 15 ml THF is slowly added dropwise. This mixture is stirred for 70 minutes at −78° C. and then a solution of 1.5 g (10.2 mmol) ($S_s$)-ethylidene-N-tert.-butyl-sulphinamide (prepared analogously to J. Ellman et al. J. Org. Chem. 2001, 66, 8772 from acetaldehyde and ($S_s$)-tert.-butylsulphinamide) in 15 ml THF is added dropwise. The mixture is stirred for 2.5 hours at −70 to −65° C. The reaction mixture is combined with 5 ml of sat. ammonium chloride solution and after thawing water and ethyl acetate are added. The aqueous phase is extracted three times with ethyl acetate, the combined organic phases are dried through sodium sulphate and evaporated to dryness i. vac. The residue is purified by column chromatography on silica gel (eluant DCM/MeOH 100:3)

$R_t$ value: 1.45 min (Method B)
$C_{14}H_{19}BrN_2OS$ (343.28)
Mass spectrum: $(M+H)^+ = 343/345$ (bromine isotopes)

(b) (R)-2-(2-Amino-propyl)-4-bromo-benzonitrile (as hydrochloride salt)

830 mg (2.4 mmol) ($S_s$,R)-2-methyl-propane-2-sulphinic acid-[2-(5-bromo-2-cyano-phenyl)-1-methyl-ethyl]-amide are dissolved in 10 ml of ethanolic hydrochloric acid (40%) and stirred for 3 hours at 60° C. and then for 16 hours at RT. Then the reaction mixture is evaporated to dryness.

$R_t$ value: 0.97 min (Method B)
$C_{10}H_{11}BrN_2 \times HCl$ (239.12)
Mass spectrum: $(M+H)^+ = 239/241$ (bromine isotopes)

(c) (R)-6-Bromo-3-methyl-3,4-dihydro-2H-isoquinolin-1-one 480 mg (1.7 mmol) (R)-2-(2-amino-propyl)-4-bromo-benzonitrile (as hydrochloride salt) are dissolved in 5 ml 10 N sodium hydroxide solution and stirred for 16 hours at 80° C. Then the reaction mixture is acidified with hydrochloric acid and extracted three times with ethyl acetate. The combined organic phases are dried on sodium sulphate, filtered and evaporated down i. vac. The residue is purified by RP-HPLC.

$R_t$ value: 1.31 min (Method B)
$C_{10}H_{10}BrNO$ (240.10)
Mass spectrum: $(M+H)^+ = 240/242$ (bromine isotopes)

(d) (R)-6-Bromo-2,3-dimethyl-3,4-dihydro-2H-isoquinolin-1-one 426 mg (1.7 mmol) (R)-6-bromo-3-methyl-3,4-dihydro-2H-isoquinolin-1-one are dissolved in 3 ml DMF and at 0° C. combined with 80 mg (2 mmol) sodium hydride (60% in mineral oildispersion). After 10 minutes 122 µl (1.9 mmol) methyl iodide are added dropwise, and the mixture is stirred for 16 hours at RT. Then the reaction mixture is mixed with water and extracted three times with ethyl acetate. The combined organic phases are dried on sodium sulphate, filtered and evaporated down i. vac. The residue is purified by flash chromatography on silica gel (eluant DCM/MeOH 20:1).

$R_t$ value: 1.40 min (Method B)
$C_{11}H_{12}BrNO$ (254.12)
Mass spectrum: $(M+H)^+ = 254/256$ (bromine isotopes)

(e) Methyl (R)-2,3-dimethyl-1-oxo-1,2,3,4-tetrahydroiso-quinoline-6-carboxylate

In an inertised autoclave 100 mg (394 µmol) (R)-6-bromo-2,3-dimethyl-3,4-dihydro-2H-isoquinolin-1-one are dissolved in a mixture of 20 ml MeOH and 5 ml DMF and combined with 20 mg (89 µmol) palladium(II)-acetate, 70 mg (86 µmol) 1,1'-bis-(diphenylphospino)-ferrocene-dichloro-palladium(II) complex with DCM and 110 µl (08.0 Mmol) TEA. Then 2 bar carbon monoxide are compressed in and the mixture is shaken for 16 hours. Then the same amount of palladium(II)-acetate and 1,1'-bis-(diphenylphospino)-ferrocene-dichloropalladium(II) complex with DCM is added twice more and each time the mixture is shaken for a further 24 hours at the same temperature. The mixture is left to cool and filtered to remove the catalyst mixture. The filtrate is evaporated down i. vac. The residue thus obtained is purified by flash chromatography on silica gel (eluant PE/EE 1:1). The fractions that contain the product are combined and concentrated i. vac. The crude product is purified by RP-HPLC.

$R_t$ value: 1.22 min (Method B)

$C_{13}H_{15}NO_3$ (233.26)

Mass spectrum: $(M+H)^+=234$ (f) Methyl (R)-2,3-dimethyl-1,2,3,4-tetrahydroisoquinoline-6-carboxylate 60 mg (257 µmol) methyl (R)-2,3-dimethyl-1-oxo-1,2,3,4-tetrahydroisoquinoline-6-carboxylate are dissolved in 2 ml THF under an argon atmosphere and at RT combined with 100 µl (542 µmol) diphenylsilane. Then 20 mg (21 µmol) carbonylhydridotris(triphenylphosphine)rhodium(I) are added and the mixture is stirred for two hours. A further 50 µl diphenylsilane and 10 mg carbonylhydridotris(triphenylphosphine)rhodium(I) are added and the mixture is stirred for a further 2.5 hours. Then the reaction mixture is evaporated down i. vac. and purified by flash chromatography on silica gel (eluant DCM/MeOH 95:5).

$R_t$ value: 0.93 min (Method B)

$C_{13}H_{17}NO_2$ (219.28)

Mass spectrum: $(M+H)^+=220$ (g) (R)-2,3-Dimethyl-1,2,3,4-tetrahydroisoquinoline-6-carboxylic acid (as hydrochloride salt)

44 mg (201 µmol) methyl (R)-2,3-dimethyl-1,2,3,4-tetrahydroisoguinoline-6-carboxylate are dissolved in 2 ml 6 N hydrochloric acid and stirred at 60° C. for one day. Then the reaction mixture is concentrated i. vac. and lyophilised.

$R_t$ value: 0.62 min (Method B)

$C_{12}H_{15}NO_2 \times HCl$ (205.26)

Mass spectrum: $(M+H)^+=206$ (h) (2S,4R)-4-[(5-Chloro-thiophene-2-carbonyl)-amino]-1-[(3R)-2,3-dimethyl-1,2,3,4-tetrahydroisoguinoline-6-carbonyl]-pyrrolidine-2-carboxylic acid-dimethylamide (as the trifluoroacetate salt)

Prepared analogously to Example 1b from tert. Butyl (2S,4R)-4-[(5-chloro-thiophene-2-carbonyl)-amino]-2-dimethylcarbamoyl-pyrrolidine-1-carboxylate and (R)-2,3-dimethyl-1,2,3,4-tetrahydroisoguinoline-6-carboxylic acid (as hydrochloride salt) with HATU as coupling reagent.

$R_t$ value: 1.10 min (Method B)

$C_{24}H_{29}ClN_4O_3S \times CF_3CO_2H$ (489.04)

Mass spectrum: $(M+H)^+=489/491$ (chlorine isotopes)

The following compounds may be prepared analogously:

EXAMPLE 32

(3SR,4SR)-5-Chloro-thiophene-2-carboxylic acid-[4-benzyloxy-1-(2-methyl-1,2,3,4-tetrahydro-isoquinoline-6-carbonyl)-pyrrolidin-3-yl]-amide (as the trifluoroacetate salt)

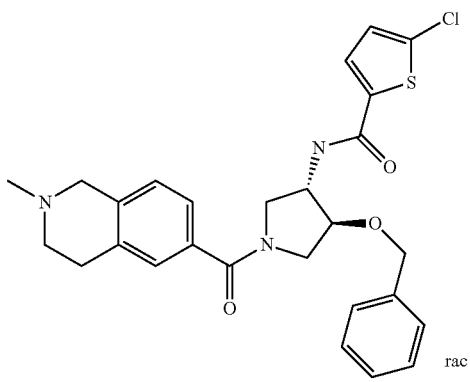

(a) tert. Butyl (3SR,4SR)-3-azido-4-hydroxy-pyrrolidine-1-carboxylate 1.7 g (9.2 mmol) tert. Butyl rac-6-oxa-3-aza-bicyclo[3.1.0]hexan-3-carboxylate (prepared analogously to Y. Tsuzuki et al. *Tetrahedron Asymm.* 2001, 12, 2989) are dissolved in a mixture of 16 ml 1,4-dioxane and 3 ml of water, combined with 1.8 g (27.5 mmol) sodium azide and stirred for 20 hours at 100° C. Then the reaction mixture is cooled, mixed with water and extracted three times with ethyl acetate. The combined organic phases are washed with sat. sodium chloride solution and mixed with activated charcoal, then dried on sodium sulphate and evaporated down i. vac.

$R_f$ value: 0.80 (silica gel, eluant DCM/MeOH 10:1))

$C_9H_{16}N_4O_3$ (228.25)

Mass spectrum: $(M+H)^+=229$ (b) tert. Butyl (3SR,4SR)-3-amino-4-hydroxy-pyrrolidine-1-carboxylate Prepared analogously to Example 14c from tert. Butyl (3SR,4SR)-3-azido-4-hydroxy-pyrrolidine-1-carboxylate.

$R_t$ value: 0.42 min (Method C)

$C_9H_{18}N_2O_3$ (202.25)

Mass spectrum: $(M+H)^+=203$ (c) tert. Butyl (3SR,4SR)-3-[(5-chloro-thiophene-2-carbonyl)-amino]-4-hydroxy-pyrrolidine-1-carboxylate 201 mg (1.2 mmol) 5-chlorothiophene-2-carboxylic acid and 436 mg (1.4 mmol) TBTU are suspended in 5 ml DCM

| N°. | Structural formula / Name | Mass peak(s) | $R_f$-value or $R_t$ |
|---|---|---|---|
| 30 | (2S,4R)-4-[(5-chloro-thiophene-2-carbonyl)-amino]-1-[(3S)-2,3-dimethyl-1,2,3,4-tetrahydroisoquinoline-6-carbonyl]-pyrrolidine-2-carboxylic acid-dimethylamide (as the trifluoroacetate salt) | $(M+H)^+=489/491$ (chlorine isotopes) | $R_t$ value: 1.16 min (Method B) | and combined with 260 μl (1.9 mmol) TEA. The mixture is stirred for 30 minutes and then a solution of 250 mg (1.2 mmol) tert. Butyl (3SR,4SR)-3-amino-4-hydroxy-pyrrolidine-1-carboxylate in 5 ml DCM is added and the mixture is stirred for 16 hours at RT. Then the reaction mixture is poured into water and extracted with DCM. The organic phase is washed with sat. sodium chloride solution and, after being mixed with activated charcoal, dried on sodium sulphate. The mixture is filtered and the filtrate is evaporated to dryness. The residue thus obtained is purified by column chromatography (silica gel, eluant DCM/MeOH 10:1).

$R_t$ value: 0.70 min (Method C)
$C_{14}H_{19}ClN_2O_4S$ (346.83)
Mass spectrum: $(M+H)^+=347/349$ (chlorine isotopes)

(d) tert. Butyl (3SR,4SR)-3-benzyloxy-4-[(5-chloro-thiophene-2-carbonyl)-amino]-pyrrolidine-1-carboxylate 67 mg (193 μmol) tert. Butyl (3SR,4SR)-3-[(5-chloro-thiophene-2-carbonyl)-amino]-4-hydroxy-pyrrolidine-1-carboxylate are dissolved in 500 μl DMF and washed successively with 15 mg (367 μmol) sodium hydride (60% dispersion in mineral oil) and 25 μl (212 μmol) benzylbromide. After two hours a further 15 mg sodium hydride dispersion are added and the reaction mixture is stirred for 16 hours at RT. Then the mixture is poured onto water and extracted with DCM. The organic phase is dried on sodium sulphate, filtered and evaporated down i. vac. The residue thus obtained is purified by column chromatography on silica gel (eluant petroleum ether/ethyl acetate 3:1)

$R_t$ value: 1.80 min (Method B)
$C_{21}H_{25}ClN_2O_4S$ (436.95
Mass spectrum: $(M+H)^+=437/439$ (chlorine isotopes)

(e) (3SR,4SR)-5-Chloro-thiophene-2-carboxylic acid-[4-benzyloxy-1-(2-methyl-1,2,3,4-tetrahydro-isoquinoline-6-carbonyl)-pyrrolidin-3-yl]-amide (as the trifluoroacetate salt)

Prepared analogously to Example 1b from tert. Butyl (3SR, 4SR)-3-[(5-chloro-thiophene-2-carbonyl)-amino]-4-hydroxy-pyrrolidine-1-carboxylate.

$R_t$ value: 1.42 min (Method B)
$C_{27}H_{28}ClN_3O_3S$ (510.06)
Mass spectrum: $(M+H)^+=510/512$ (chlorine isotopes)

The following compounds may be prepared analogously:

| N°. | Structural formula / Name | Mass peak(s) | $R_f$ value or $R_t$ |
|---|---|---|---|
| 27 | (3SR,4SR)-5-chloro-thiophene-2-carboxylic acid-[4-ethoxy-1-(3-methyl-1,2,3,4-tetrahydro-isoquinoline-6-carbonyl)-pyrrolidin-3-yl]-amide (as the trifluoroacetate salt) | $(M + H)^+ = 448/450$ (chlorine isotopes) | $R_t$ value: 1.21 min (Method B) |
| 31 | (2S,4R)-5-chloro-thiophene-2-carboxylic acid-[5-methoxymethyl-1-(3-methyl-2,3,4,5-tetrahydro-1H-benzo[d]azepine-7-carbonyl)-pyrrolidin-3-yl]-amide (as the trifluoroacetate salt) | $(M + H)^+ = 462/464$ (chlorine isotopes) | $R_t$ value: 1.16 min (Method B) |
| 74 | (3R,5S)-5-chloro-thiophene-2-carboxylic acid-{5-methoxymethyl-1-[6-methyl-4,5,6,7-tetrahydro-thieno[2,3-c]pyridine-2-carbonyl]-pyrrolidin-3-yl}-amide (as the trifluoroacetate salt) | $(M + H)^+ = 455/456$ (chlorine isotopes) | $R_t$ value: 1.14 min (Method F) |

EXAMPLE 39

(R)-5-Ethynyl-thiophene-2-carboxylic acid-[1-(2-methyl-1,2,3,4-tetrahydroisoquinoline-6-carbonyl)-pyrrolidin-3-yl]-amide (as the trifluoroacetate salt)

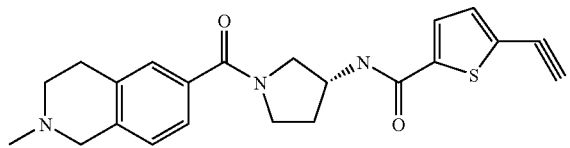

(a) tert. Butyl (R)-[1-(2-methyl-1,2,3,4-tetrahydroisoquinoline-6-carbonyl)-pyrrolidin-3-yl]-carbamate 1.1 g (4.8 mmol) 2-methyl-1,2,3,4-tetrahydroisoquinoline-6-carboxylic acid (as hydrochloride) are dissolved in 12 ml DMF, mixed with 2.1 ml (19.3 mmol) NMM and 1.8 g (4.8 mmol) HATU and stirred for five minutes at RT. Then 0.9 g (4.8 mmol) tert. Butyl (R)-pyrrolidin-3-yl-carbamate are added and the mixture is stirred for 16 hours. Then the mixture is poured onto water and extracted with DCM. The organic phase is separated using a phase separation cartridge and evaporated to dryness i. vac. The residue is purified by flash chromatography on silica gel (eluant DCM/MeOH 9:1 to 8:2).

$R_f$ value: 1.00 min (Method B)
$C_{20}H_{29}N_3O_3$ (330.83)
Mass spectrum: $(M+H)^+ = 360$ (b) (R)-(3-Amino-pyrrolidin-1-yl)-(2-methyl-1,2,3,4-tetrahydroisoquinolin-6-yl)-methanone 1.4 g (3.8 mmol) tert. Butyl (R)-[1-(2-methyl-1,2,3,4-tetrahydroisoquinoline-6-carbonyl)-pyrrolidin-3-yl]-carbamate are dissolved in 5 ml THF and slowly combined with 9.5 ml hydrochloric acid (4 M in 1,4-dioxane). The mixture is stirred for two hours, then concentrated down to ⅔ of its volume and the crude product is filtered off as a precipitate, which is then purified by RP-HPLC (eluant: gradient ammonia/acetonitrile).

$R_f$ value: 0.42 min (Method C)
$C_{15}H_{21}N_3O$ (259.35)
Mass spectrum: $(M+H)^+ = 260$ (c) (R)-5-Ethynyl-thiophene-2-carboxylic acid-[1-(2-methyl-1,2,3,4-tetrahydroisoquinoline-6-carbonyl)-pyrrolidin-3-yl]-amide (as the trifluoroacetate salt)

Prepared analogously to Example 39a from (R)-(3-amino-pyrrolidin-1-yl)-(2-methyl-1,2,3,4-tetrahydroisoquinolin-6-yl)-methanone and 5-ethynyl-thiophene-2-carboxylic acid.

$R_f$ value: 1.06 min (Method B)
$C_{22}H_{23}N_3O_2S \times CF_3CO_2H$ (393.51)
Mass spectrum: $(M+H)^+ = 394$ The following compounds may be prepared analogously:

| N°. | Structural formula / Name | Mass peak(s) | $R_f$ value or $R_t$ |
|---|---|---|---|
| 36 | (R)-thiophene-2-carboxylic acid-[1-(2-methyl-1,2,3,4-tetrahydro-isoquinoline-6-carbonyl)-pyrrolidin-3-yl]-amide (as the trifluoroacetate salt) | $(M+H)^+ = 370$ | $R_t$ value = 0.91 min (Method B) |
| 37 | (R)-3-methoxy-N-[1-(2-methyl-1,2,3,4-tetrahydroisoquinoline-6-carbonyl)-pyrrolidin-3-yl]-benzamide (as the trifluoroacetate salt) | $(M+H)^+ = 394$ | $R_t$ value = 0.97 min (Method B) |
| 38 | (R)-4-methoxy-N-[1-(2-methyl-1,2,3,4-tetrahydroisoquinoline-6-carbonyl)-pyrrolidin-3-yl]-benzamide (as the trifluoroacetate salt) | $(M+H)^+ = 394$ | $R_t$ value = 0.96 min (Method B) |

-continued

| N°. | Structural formula<br>Name | Mass peak(s) | $R_f$ value or $R_t$ |
|---|---|---|---|
| 40 | (R)-4-bromo-thiophene-2-carboxylic acid-[1-(2-methyl-1,2,3,4-tetrahydro-isoquinoline-6-carbonyl)-pyrrolidin-3-yl]-amide (as the trifluoroacetate salt) | $(M + H)^+$ = 448/450 (bromine isotopes) | $R_t$ value = 1.08 min (Method B) |
| 41 | (R)-5-bromo-furan-2-carboxylic acid-[1-(2-methyl-1,2,3,4-tetrahydro-isoquinoline-6-carbonyl)-pyrrolidin-3-yl]-amide (as the trifluoroacetate salt) | $(M + H)^+$ = 432/434 (bromine isotopes) | $R_t$ value = 0.96 min (Method B) |
| 42 | (R)-5-chloro-pyridine-2-carboxylic acid-[1-(2-methyl-1,2,3,4-tetrahydroisoquinoline-6-carbonyl)-pyrrolidin-3-yl]-amide (as bis-trifluoroacetate salt) | $(M + H)^+$ = 399/401 (chlorine isotopes) | $R_t$ value = 1.01 min (Method B) |
| 43 | (R)-4-chloro-N-[1-(2-methyl-1,2,3,4-tetrahydroisoquinoline-6-carbonyl)-pyrrolidin-3-yl]-benzamide (as the trifluoroacetate salt) | $(M + H)^+$ = 398/400 (chlorine isotopes) | $R_t$ value = 1.01 min (Method B) |
| 44 | (R)-3-chloro-N-[1-(2-methyl-1,2,3,4-tetrahydroisoquinoline-6-carbonyl)-pyrrolidin-3-yl]-benzamide (as the trifluoroacetate salt) | $(M + H)^+$ = 398/400 (chlorine isotopes) | $R_t$ value = 1.01 min (Method B) |

EXAMPLE 45

(3SR,4SR)-5-Chloro-thiophene-2-carboxylic acid-[4-methyl-1-(2-methyl-1,2,3,4-tetrahydroisoquinoline-6-carbonyl)-pyrrolidin-3-yl]-amide (as the trifluoroacetate salt)

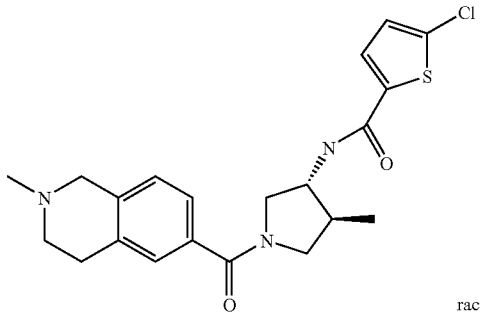

(a) Methyl (3RS,4RS)-1-benzyl-4-methyl-pyrrolidine-3-carboxylate (as the trifluoroacetate salt)

830 µl (7.8 mmol) methyl crotonate are dissolved in 25 ml DCM and combined with 61 µl (0.79 mmol) TFA. Then a solution of 2.0 ml (7.8 mmol) N-methoxymethyl-N-trimethylsilylmethyl-benzylamine in 5 ml DCM is added dropwise within 20 minutes. The reaction mixture is stirred for 16 hours and then evaporated down i. vac. The residue is purified by RP-HPLC.

$R_t$ value: 0.94 min (Method B)
$C_{14}H_{19}NO_2$ (233.31)
Mass spectrum: $(M+H)^+$=234

(b) (3RS,4RS)-1-Benzyl-4-methyl-pyrrolidine-3-carboxylic acid (as hydrochloride salt)

2.0 g (5.7 mmol) methyl (3RS,4RS)-1-benzyl-4-methyl-pyrrolidine-3-carboxylate (as the trifluoroacetate salt) are dissolved in 4 ml of methanol and combined with 5 ml lithium hydroxide solution (8% in water). The mixture is stirred for five hours at RT, then mixed with 3.2 ml 4N hydrochloric acid and evaporated to dryness.

$R_t$ value: 0.83 min (Method B)
$C_{13}H_{17}NO_2$ (219.29)
Mass spectrum: $(M+H)^+$=220

(c) Methyl (3RS,4RS)-1-benzyl-4-methyl-pyrrolidine-3-carboxylate 1.3 g (4.9 mmol) (3RS,4RS)-1-benzyl-4-methyl-pyrrolidine-3-carboxylic acid (as hydrochloride salt) are dissolved in 10 ml of methanol and combined with 0.6 ml (8.5 mmol) thionyl chloride while cooling with an ice bath. The ice bath is removed and the mixture is refluxed for three hours. Then the mixture is evaporated down i. vac. and combined with 1N sodium hydroxide solution. The aqueous phase is extracted three times with ethyl acetate. The combined organic phases are dried on sodium sulphate, filtered and evaporated down i. vac.

$R_t$ value: 1.00 min (Method B)
$C_{14}H_{19}NO_2$ (233.31)
Mass spectrum: $(M+H)^+$=234

(d) Methyl (3RS,4RS)-4-methyl-pyrrolidine-3-carboxylate (as hydrochloride salt)

927 mg (4 mmol) methyl (3RS,4RS)-1-benzyl-4-methyl-pyrrolidine-3-carboxylate are dissolved in 15 ml of methanol, combined with 100 mg palladium/charcoal (10%) and 2 ml of 2N hydrochloric acid and hydrogenated for 14 hours with 3 bar hydrogen. Then the mixture is filtered and evaporated down i. vac.

$R_t$ value: 0.39 min (Method B)
$C_7H_{13}NO_2 \times HCl$ (143.19)
Mass spectrum: $(M+H)^+$=144

(e) (3RS,4RS)-4-Methyl-1-(2-methyl-1,2,3,4-tetrahydroisoquinoline-6-carbonyl)-pyrrolidine-3-carboxylic acid (as the trifluoroacetate salt)

880 mg (3.9 mmol) 2-methyl-1,2,3,4-tetrahydroisoquinoline-6-carboxylic acid (as hydrochloride salt) are dissolved in 2 ml DMF and combined with 1.5 g (3.9 mmol) HATU and 1.7 ml (15.6 mmol) NMM. The mixture is stirred for five minutes at RT and then a solution of 700 mg (3.9 mmol) methyl (3RS,4RS)-4-methyl-pyrrolidine-3-carboxylate (as hydrochloride salt) in 2 ml DMF is added. The reaction mixture is stirred for 16 hours at RT, then mixed with 2N sodium hydroxide solution and extracted three times with ethyl acetate. The aqueous phase is acidified with TFA and purified by RP-HPLC. The carboxylic acid is obtained as the product.

$R_t$ value: 0.74 min (Method B)
$C_{17}H_{22}N_2O_3 \times CF_3CO_2H$ (302.38)
Mass spectrum: $(M+H)^+$=303

(f) (3RS,4SR)-(3-Amino-4-methyl-pyrrolidin-1-yl)-(2-methyl-1,2,3,4-tetrahydroisoquinolin-6-yl)-methanone 72 mg (173 µmol) (3RS,4RS)-4-methyl-1-(2-methyl-1,2,3,4-tetrahydroisoquinoline-6-carbonyl)-pyrrolidine-3-carboxylic acid (as the trifluoroacetate salt) are dissolved in 4 ml tert.-butanol and combined with 95 µl (682 µmol) TEA. Then 150 µl (675 µmol) diphenylphosphoric acid azide are added and the mixture is stirred for two hours at reflux temperature. The reaction mixture is then combined with 2N sodium hydroxide solution and extracted three times with ethyl acetate. The aqueous phase is concentrated down to 6 ml volume i. vac. and purified by RP-HPLC (eluant: ammonia/acetonitrile). The amine is obtained as the product.

R value: 0.46 min (Method C)
$C_{16}H_{23}N_3O$ (273.37)
Mass spectrum: $(M+H)^+$=274

(g) (3SR,4SR)-5-Chloro-thiophene-2-carboxylic acid-[4-methyl-1-(2-methyl-1,2,3,4-tetrahydroisoquinoline-6-carbonyl)-pyrrolidin-3-yl]-amide (as the trifluoroacetate salt)

Prepared analogously to Example 1a from (3RS,4RS)-(3-amino-4-methyl-pyrrolidin-1-yl)-(2-methyl-1,2,3,4-tetrahydroisoquinolin-6-yl)-methanone.

$R_t$ value: 1.18 min (Method B)
$C_{21}H_{24}ClN_3O_2S \times CF_3CO_2H$ (417.96)
Mass spectrum: $(M+H)^+$=418/420 (chlorine isotopes)

EXAMPLE 46

Methyl (2S,4R)-4-[(5-chloro-thiophene-2-carbonyl)-amino]-1-(2-methyl-2,3-dihydro-1H-isoindole-5-carbonyl)-pyrrolidine-2-carboxylate (as the trifluoroacetate salt)

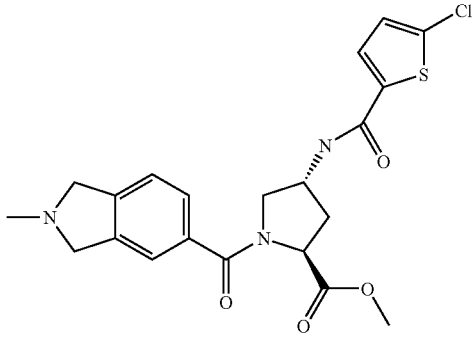

(a) Methyl 2,3-dihydro-1H-isoindole-5-carboxylate

Prepared analogously to Example 45c from 2,3-dihydro-1H-isoindole-5-carboxylic acid (as hydrochloride salt; prepared analogously to EP 0 528 369).

$R_t$ value: 0.49 min (Method D)
$C_{10}H_{11}NO_2$ (177.20)
Mass spectrum: $(M+H)^+$=178

(b) Methyl 2-methyl-2,3-dihydro-1H-isoindole-5-carboxylate 1.2 g (6.6 mmol) methyl 2,3-dihydro-1H-isoindole-5-carboxylate are dissolved in 5 ml formic acid, combined with 2 ml formalin solution (37% solution in water), heated to 70° C. for 3.5 hours and stirred for 16 hours at RT. The reaction mixture is evaporated down i. vac. and combined with 0.1 N sodium hydroxide solution and extracted three times with ethyl acetate. The combined organic phases are dried on sodium sulphate, filtered and evaporated down i. vac.

$R_t$ value: 0.60 min (Method E)
$C_{11}H_{13}NO_2$ (191.23)
Mass spectrum: $(M+H)^+=192$ (c) 2-Methyl-2,3-dihydro-1H-isoindole-5-carboxylic acid (as hydrochloride salt)

Prepared analogously to Example 26 g from methyl 2-methyl-2,3-dihydro-1H-isoindole-5-carboxylate.

$R_t$ value: 0.25 min (Method B)
$C_{10}H_{11}NO_2 \times HCl$ (177.20)
Mass spectrum: $(M+H)^+=178$ (d) Methyl (2S,4R)-4-[(5-chloro-thiophene-2-carbonyl)-amino]-1-(2-methyl-2,3-dihydro-1H-isoindole-5-carbonyl)-pyrrolidine-2-carboxylate (as the trifluoroacetate salt)

Prepared analogously to Example 1b from 1-tert.-butyl-2-methyl (2S,4R)-4-[(5-chloro-thiophene-2-carbonyl)-amino]-pyrrolidine-1,2-dicarboxylate and 2-methyl-2,3-dihydro-1H-isoindole-5-carboxylic acid (as hydrochloride salt).

$R_t$ value: 1.14 min (Method B)
$C_{21}H_{22}ClN_3O_4S \times CF_3CO_2H$ (447.94)
Mass spectrum: $(M+H)^+=448/450$ (chlorine isotopes)

EXAMPLE 35

(R)-5-Chloro-thiophene-2-carboxylic acid-[1-(6-methyl-5,6,7,8-tetrahydro-4H-thieno[2,3-d]azepine-2-carbonyl)-pyrrolidin-3-yl]-amide (as the trifluoroacetate salt)

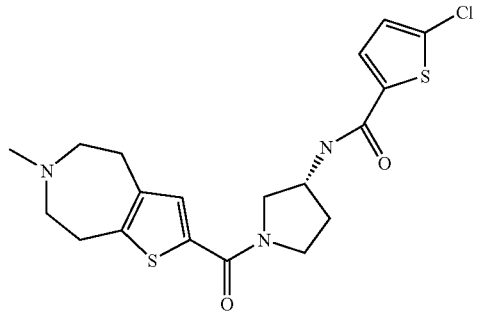

(a) Methyl 5,6,7,8-tetrahydro-4H-thieno[2,3-d]azepine-2-carboxylate (as hydrochloride)

Prepared analogously to DE 3105858 from methyl 6-(3-chloro-benzyl)-5,6,7,8-tetrahydro-4H-thieno[2,3-d]azepine-2-carboxylate.

$R_t$ value: 0.85 min (Method B)
$C_{10}H_{13}NO_2S \times HCl$ (211.28)
Mass spectrum: $(M+H)^+=212$ (b) Methyl 6-methyl-5,6,7,8-tetrahydro-4H-thieno[2,3-d]azepine-2-carboxylate Prepared analogously to Example 46b from methyl 5,6,7,8-tetrahydro-4H-thieno[2,3-d]azepine-2-carboxylate (as hydrochloride).

$R_t$ value: 0.64 min (Method E)
$C_{11}H_{15}NO_2S$ (225.31)
Mass spectrum: $(M+H)^+=226$ (c) 6-Methyl-5,6,7,8-tetrahydro-4H-thieno[2,3-d]azepine-2-carboxylic acid (as hydrochloride)

Prepared analogously to Example 45b from methyl 5,6,7,8-tetrahydro-4H-thieno[2,3-d]azepine-2-carboxylate (as hydrochloride).

Yield: quantitativ
$C_{10}H_{13}NO_2S \times HCl$ (211.28)
Mass spectrum: $(M+H)^+=212$ (d) (R)-5-Chloro-thiophene-2-carboxylic acid-[1-(6-methyl-5,6,7,8-tetrahydro-4H-thieno[2,3-d]azepine-2-carbonyl)-pyrrolidin-3-yl]-amide (as the trifluoroacetate salt)

Prepared analogously to Example 1b from tert. Butyl (R)-3-[(5-chloro-thiophene-2-carbonyl)-amino]-pyrrolidine-1-carboxylate and 6-methyl-5,6,7,8-tetrahydro-4H-thieno[2,3-d]azepine-2-carboxylic acid (as hydrochloride).

$R_t$ value: 1.15 min (Method B)
$C_{19}H_{22}ClN_3O_2S_2 \times CF_3CO_2H$ (423.99)
Mass spectrum: $(M+H)^+=424/426$ (chlorine isotopes)

EXAMPLE 47

(3SR,4SR)-5-Chloro-thiophene-2-carboxylic acid-[4-methoxy-1-(5-methyl-4,5,6,7-tetrahydro-thieno[3,2-c]pyridine-2-carbonyl)-pyrrolidin-3-yl]-amide (as the trifluoroacetate salt)

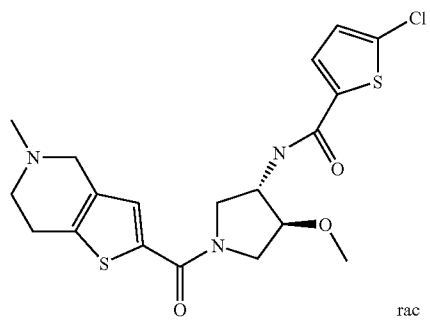

(a) 5-tert.-butyl-2-ethyl 6,7-dihydro-4H-thieno[3,2-c]pyridine-2,5-dicarboxylate 1.5 ml (20.1 mmol) DMF are slowly combined at 0° C. with 1.5 ml (16.1 mmol) phosphorus oxychloride. Then the mixture is taken up in 10 ml DCM and stirred for 45 minutes at RT. Then 2.2 g (9.8 mmol) tert. Butyl 4-oxo-piperidine-1-carboxylate, dissolved in 10 ml DCM, are added dropwise to the mixture at 0-5° C. A further 10 ml DCM are added and the mixture is stirred for one hour at RT. The reaction mixture is then poured onto a mixture of ice and 20 ml saturated sodium acetate solution and stirred for one hour. The organic phase is separated off, washed several times with water and then dried on sodium sulphate and evaporated down i. vac.

The crude product thus obtained is dissolved in 15 ml DCM and combined with a mixture of 1.8 ml (16.0 mmol) ethyl mercaptoacetate and 2.8 ml (19.9 mmol) TEA in 5 ml DCM. Then the reaction mixture is refluxed for 2.5 hours and then stirred for one hour at RT. Water is added, the organic phase is separated off and washed with plenty of water. The organic phase is dried on sodium sulphate, filtered and evaporated down i. vac. The residue is purified by flash chromatography on silica gel (eluant mixture of cyclohexane/ethyl acetate 9:1 to 8:2).

$R_t$ value: 1.71 min (Method B)
$C_{15}H_{21}NO_4S$ (311.40)
Mass spectrum: $(M+H)^+=312$ (b) Ethyl 5-methyl-4,5,6,7-tetrahydro-thieno[3,2-c]pyridine-2-carboxylate (as the trifluoroacetate salt)

615 mg (987 µmol, 50% purity) 5-tert.-butyl-2-ethyl 6,7-dihydro-4H-thieno[3,2-c]pyridine-2,5-dicarboxylate are dissolved in 4 ml of a mixture of TFA and DCM (v/v 1:1) and stirred for 30 minutes at RT. The reaction mixture is neutralised by the addition of TEA and evaporated down i. vac.

The crude product thus obtained is dissolved in 4 ml formic acid and combined with 0.5 ml (6.7 mmol) formalin solution (37% in water). The reaction mixture is stirred for 16 hours at 70° C. After cooling to RT the mixture is made basic with 50% aqueous sodium hydroxide solution and saturated sodium hydrogen carbonate solution and extracted with ethyl acetate. The organic phase is washed three times with water, dried on sodium sulphate, filtered and evaporated down i. vac. The residue is purified by RP-HPLC.

$R_t$ value: 0.90 min (Method B)
$C_{11}H_{15}NO_2S \times CF_3CO_2H$ (225.31)
Mass spectrum: $(M+H)^+ = 226$ (c) 5-Methyl-4,5,6,7-tetrahydro-thieno[3,2-c]pyridine-2-carboxylic acid (as hydrochloride salt)

Prepared analogously to Example 45b from ethyl 5-methyl-4,5,6,7-tetrahydro-thieno[3,2-c]pyridine-2-carboxylate (as the trifluoroacetate salt).

$R_t$ value: 0.29 min (Method B)
$C_9H_{11}NO_2S \times HCl$ (197.26)
Mass spectrum: $(M+H)^+ = 198$ (d) (3SR,4SR)-5-chloro-thiophene-2-carboxylic acid-[4-methoxy-1-(5-methyl-4,5,6,7-tetrahydro-thieno[3,2-c]pyridine-2-carbonyl)-pyrrolidin-3-yl]-amide (as the trifluoroacetate salt)

Prepared analogously to Example 1b from tert. Butyl (3SR,4SR)-3-[(5-chloro-thiophene-2-carbonyl)-amino]-4-methoxy-pyrrolidine-1-carboxylate and 5-methyl-4,5,6,7-tetrahydro-thieno[3,2-c]pyridine-2-carboxylic acid (as hydrochloride salt).

$R_t$ value: 1.17 min (Method B)
$C_{19}H_{22}ClN_3O_3S_2 \times CF_3CO_2H$ (439.99)
Mass spectrum: $(M+H)^+ = 440/442$ (chlorine isotopes)

EXAMPLE 48

(3SR,4SR)-5-Chloro-thiophene-2-carboxylic acid-[4-methoxy-1-(6-methyl-4,5,6,7-tetrahydro-thieno[2,3-c]pyridine-2-carbonyl)-pyrrolidin-3-yl]-amide (as the trifluoroacetate salt)

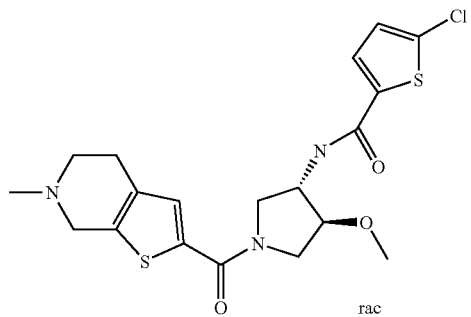

(a) Methyl 6-methyl-4,5,6,7-tetrahydro-thieno[2,3-c]pyridine-2-carboxylate (as the trifluoroacetate salt)

496 mg (2.1 mmol) 2-bromo-6-methyl-4,5,6,7-tetrahydro-thieno[2,3-c]pyridine (prepared analogously to EP 0314154 from 6-methyl-4,5,6,7-tetrahydro-thieno[2,3-c]pyridine) are dissolved in 10 ml THF and cooled to −78° C. Then 2 ml (3.2 mmol) n-butyllithium solution (1.6 M in n-hexane) are slowly added dropwise. The reaction mixture is stirred for 30 minutes at −78° C. and then combined with 1.0 ml (12.9 mmol) methyl chloroformate. The mixture is stirred for five minutes at −78° C., heated to RT and the mixture is evaporated down i. vac. The residue is purified by RP-HPLC.

$R_t$ value: 0.79 min (Method B)
$C_{10}H_{13}NO_2S \times CF_3CO_2H$ (211.28)
Mass spectrum: $(M+H)^+ = 212$ (b) 6-Methyl-4,5,6,7-tetrahydro-thieno[2,3-c]pyridine-2-carboxylic acid (as hydrochloride salt)

Prepared analogously to Example 45b from methyl 6-methyl-4,5,6,7-tetrahydro-thieno[2,3-c]pyridine-2-carboxylate (as the trifluoroacetate salt).

$R_t$ value: 0.22 min (Method B)
$C_9H_{11}NO_2S \times HCl$ (197.26)
Mass spectrum: $(M+H)^+ = 198$ (c) (3SR,4SR)-5-Chloro-thiophene-2-carboxylic acid-[4-methoxy-1-(6-methyl-4,5,6,7-tetrahydro-thieno[2,3-c]pyridine-2-carbonyl)-pyrrolidin-3-yl]-amide (as the trifluoroacetate salt)

Prepared analogously to Example 1b from tert. Butyl (3SR,4SR)-3-[(5-chloro-thiophene-2-carbonyl)-amino]-4-methoxy-pyrrolidine-1-carboxylate and 6-methyl-4,5,6,7-tetrahydro-thieno[2,3-c]pyridine-2-carboxylic acid (as hydrochloride salt).

$R_t$ value: 1.16 min (Method B)
$C_{19}H_{22}ClN_3O_3S_2 \times CF_3CO_2H$ (439.99)
Mass spectrum: $(M+H)^+ = 440/442$ (chlorine isotopes)

EXAMPLE 49

(3SR,4SR)-5-Chloro-thiophene-2-carboxylic acid-[4-methoxy-1-(5-methyl-4,5,6,7-tetrahydro-thiazolo[5.4-c]pyridine-2-carbonyl)-pyrrolidin-3-yl]-amide (as the trifluoroacetate salt)

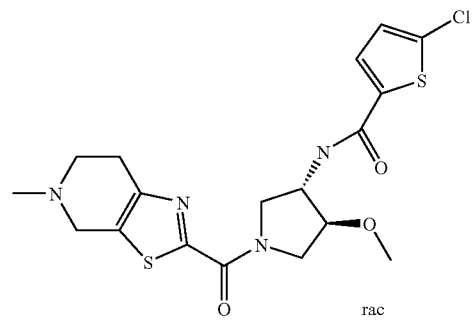

Prepared analogously to Example 26h from (3SR,4SR)-3-[(5-chloro-thiophene-2-carbonyl)-amino]-4-methoxy-pyrrolidine and 5-methyl-4,5,6,7-tetrahydro-thiazolo[5.4-c]pyridine-2-carboxylic acid (Heterocycles, 63, 2004, 1555-1562).

$R_t$ value: 1.17 min (Method B)
$C_{18}H_{21}ClN_4O_3S_2 \times CF_3CO_2H$ (440.97)
Mass spectrum: $(M+H)^+ = 441/443$ (chlorine isotopes)

The following compounds may be prepared analogously:

| N°. | Structural formula / Name | Mass peak(s) | $R_f$ value or $R_t$ |
|---|---|---|---|
| 69 | 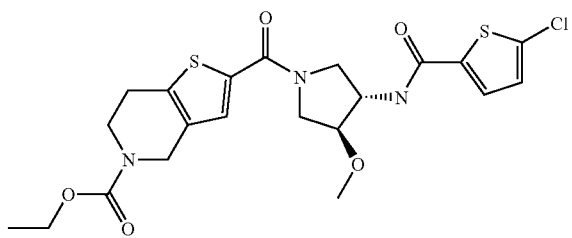 (3R,5S)-5-chloro-thiophene-2-carboxylic acid-[5-methoxymethyl-1-(5-methyl-4,5,6,7-tetrahydro-thiazolo[5,4-c]pyridine-2-carbonyl)-5-hydroxymethyl-pyrrolidin-3-yl]-amide (as the trifluoroacetate salt) | $(M+H)^+ = 455/457$ (chlorine isotopes) | $R_t$ value = 1.13 min (Method F) |

EXAMPLE 50

Ethyl 2-{(3S,4S)-3-[(5-chloro-thiophene-2-carbonyl)-amino]-4-methoxy-pyrrolidine-1-carbonyl}-6,7-dihydro-4H-thieno[3,2-c]pyridine-5-carboxylate (a) 5-Ethyl 6,7-dihydro-4H-thieno[3,2-c]pyridine-2,5-dicarboxylate 1.00 g (4.18 mmol) ethyl 2-formyl-6,7-dihydro-4H-thieno[3,2-c]pyridine-5-carboxylate are combined with 23 ml tert-butanol and 1.44 g (25 mmol) of isobutylene weighed out in the freezer and then 17 ml of an aqueous solution of 3.77 g (31 mmol) sodium hydrogen phosphate and 3.78 g (41 mmol) sodium chlorite are added and the mixture is stirred for 2 h. The reaction mixture is made basic with NaOH and extracted with ethyl acetate. Then the aqueous phase is acidified with HCl and extracted with ethyl acetate. The combined ethyl acetate fractions are dried on sodium sulphate, concentrated and the residue is purified by flash chromatography on silica gel (eluant mixture of dichloromethane:methanol 95:5 to 8:2).

$R_t$ value: 1.23 min (Method B)
$C_{11}H_{13}NO_4S$ (255.29)
Mass spectrum: $(M+H)^+=256$ (b) Ethyl 2-{(3S,4S)-3-[(5-chloro-thiophene-2-carbonyl)-amino]-4-methoxy-pyrrolidine-1-carbonyl}-6,7-dihydro-4H-thieno[3,2-c]pyridine-5-carboxylate Prepared analogously to Example 26h from (3SR,4SR)-3-[(5-chloro-thiophene-2-carbonyl)-amino]-4-methoxy-pyrrolidine and 5-ethyl 6,7-dihydro-4H-thieno[3,2-c]pyridine-2,5-dicarboxylate.

$R_t$ value: 1.4 min (Method B)
$C_{21}H_{24}ClN_3O_5S_2$ (498.02)
Mass spectrum: $(M+H)^+=498/500$ (chlorine isotopes)

EXAMPLE 51

(3SR,4SR)-5-Chloro-thiophene-2-carboxylic acid-[4-methoxy-1-(6-methyl-5,6,7,8-tetrahydro-4H-thieno[2,3-d]azepine-2-carbonyl)-pyrrolidin-3-yl]-amide (as the trifluoroacetate salt)

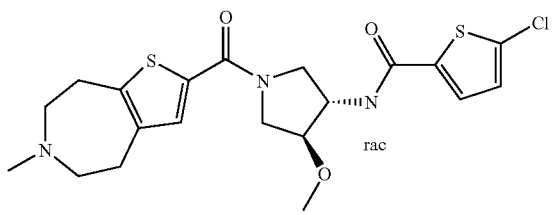

Prepared analogously to Example 1b from (3SR,4SR)-3-[(5-chloro-thiophene-2-carbonyl)-amino]-4-methoxy-pyrrolidine and 6-methyl-5,6,7,8-tetrahydro-4H-thieno[2,3-d]azepine-2-carboxylic acid (WO2004058715) with HATU as coupling reagent.

$R_t$ value: 1.09 min (Method B)
$C_{20}H_{24}ClN_3O_3S_2 \times CF_3CO_2H$ (454.01)
Mass spectrum: $(M+H)^+=454/456$ (chlorine isotopes)

EXAMPLE 52

(3SR,4SR)-5-Chloro-thiophene-2-carboxylic acid-[4-methoxy-1-(6-methyl-5,6,7,8-tetrahydro-4H-thiazolo[4,5-d]azepine-2-carbonyl)-pyrrolidin-3-yl]-amide

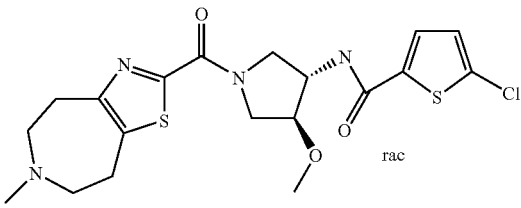

Prepared analogously to Example 1b from (3SR,4SR)-3-[(5-chloro-thiophene-2-carbonyl)-amino]-4-methoxy-pyrrolidine and 6-methyl-5,6,7,8-tetrahydro-4H-thiazolo[4,5-d]azepine-2-carboxylic acid (WO2004058715) with HATU as coupling reagent.

$R_t$ value: 1.09 min (Method F)
$C_{19}H_{23}ClN_4O_3S_2$ (455.00)
Mass spectrum: $(M+H)^+=455/457$ (chlorine isotopes)

The following compounds may be prepared analogously:

| N°. | Structural formula / Name | Mass peak(s) | $R_f$ value or $R_t$ |
|---|---|---|---|
| 68 | (3R,5S)-5-chloro-thiophene-2-carboxylic acid-[5-methoxymethyl-1-(6-methyl-5,6,7,8-tetrahydro-4H-thiazolo[4,5-d]azepine-2-carbonyl)-pyrrolidin-3-yl]-amide (as the trifluoroacetate salt) | $(M + H)^+ = 469/471$ (chlorine isotopes) | $R_t$ value = 1.14 min (Method F) |

EXAMPLE 53

(3SR,4SR)-5-Chloro-thiophene-2-carboxylic acid-[4-methoxy-1-{(4RS)-4,5-dimethyl-4,5,6,7-tetrahydro-thiazolo[5.4-c]pyridine-2-carbonyl}-pyrrolidin-3-yl]-amide

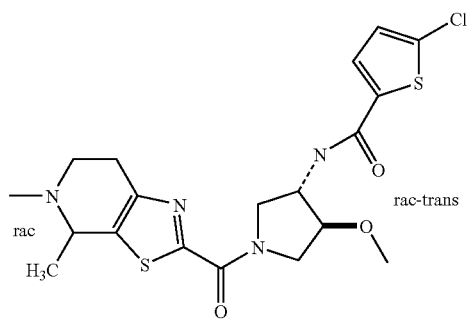

Prepared analogously to Example 1b from (3SR,4SR)-3-[(5-chloro-thiophene-2-carbonyl)-amino]-4-methoxy-pyrrolidine and (RS)-4,5-dimethyl-4,5,6,7-tetrahydro-thiazolo[5.4-c]pyridine-2-carboxylic acid (prepared analogously to WO2004058728) with HATU as coupling reagent.
$R_t$ value: 1.15 min (Method F)
$C_{19}H_{23}ClN_4O_3S_2$ (455.00)
Mass spectrum: $(M+H)^+=455/457$ (chlorine isotopes)

EXAMPLE 54

(3R,5S)-5-Chloro-thiophene-2-carboxylic acid-[4-hydroxymethyl-1-(6-methyl-4,5,6,7-tetrahydro-thieno[2,3-c]pyridine-2-carbonyl)-pyrrolidin-3-yl]-amide (as the trifluoroacetate salt)

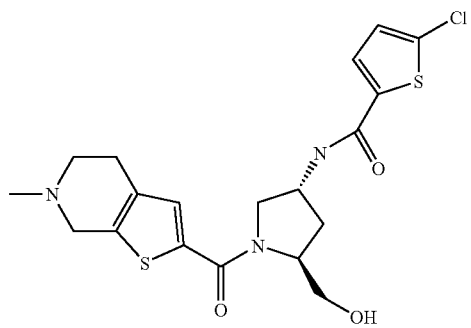

Prepared analogously to Example 1b from (3R,5S)-5-chloro-thiophene-2-carboxylic acid-(5-hydroxymethyl-pyrrolidin-3-yl)-amide and 6-methyl-4,5,6,7-tetrahydro-thieno[2,3-c]pyridine-2-carboxylic acid with HATU as coupling reagent.

$R_t$ value: 1.02 min (Method B)
$C_{19}H_{22}ClN_3O_3S_2 \times CF_3CO_2H$ (439.99)
Mass spectrum: $(M+H)^+=440/442$ (chlorine isotopes)

EXAMPLE 55

(3R,5S)-5-Chloro-thiophene-2-carboxylic acid-[5-methoxymethyl-1-(6-methyl-5,6,7,8-tetrahydro-4H-thieno[2,3-d]azepine-2-carbonyl)-pyrrolidin-3-yl]-amide (as the trifluoroacetate salt)

Prepared analogously to Example 1b from (3R,5S)-5-chloro-thiophene-2-carboxylic acid-(5-methoxymethyl-pyrrolidin-3-yl)-amide and 6-methyl-5,6,7,8-tetrahydro-4H-thieno[2,3-d]azepine-2-carboxylic acid (WO2004058715) with HATU as coupling reagent.
$R_t$ value: 1.13 min (Method B)
$C_{21}H_{26}ClN_3O_3S_2 \times CF_3CO_2H$ (468.04)
Mass spectrum: $(M+H)^+=468/470$ (chlorine isotopes)

EXAMPLE 56

(3SR,4SR)-5-Chloro-thiophene-2-carboxylic acid-[4-methoxy-1-({RS}-6,7-dimethyl-4,5,6,7-tetrahydro-thieno[2,3-c]pyridine-2-carbonyl)-pyrrolidin-3-yl]-amide (as the trifluoroacetate salt)

(a) 6,7-Dimethyl-4,5-dihydro-thieno[2,3-c]pyridinium iodide

A mixture of 4.64 g (31 mmol) 7-methyl-4,5-dihydro-thieno[2,3-c]pyridine (prepared analogously to J.Am.Chem- .Soc., 1951, 1257), 8.0 ml (128 mmol) methyl iodide and 20 ml of ethyl acetate is stirred for 15 min. The precipitate formed is suction filtered, washed with ethyl acetate and dried in vacuo.

$R_t$ value: 0.47 min (Method B)

$C_9H_{12}NS \times I$ (293.169)

Mass spectrum: $(M–I)^+ = 166$ (b) (RS)-6,7-Dimethyl-4,5,6,7-tetrahydro-thieno[2,3-c]pyridine A mixture of 7.2 g (24 mmol) 6,7-dimethyl-4,5-dihydro-thieno[2,3-c]pyridinium iodide and 80 ml of methanol is mixed batchwise 1.87 g (49 mmol) $NaBH_4$ while cooling with an ice bath (vigorous release of gas). The mixture is stirred for another 1.5 h, concentrated, mixed with sat. $NaHCO_3$ solution and extracted 3× with methylene chloride. The organic phases are dried on $NaSO_4$, filtered and concentrated.

$R_t$ value: 0.66 min (Method B)

$C_9H_{13}NS$ (167.272)

Mass spectrum: $(M+H)^+ = 168$ (c) (RS)-2-Bromo-6,7-dimethyl-4,5,6,7-tetrahydro-thieno[2,3-c]pyridine A mixture of 4.0 g (24 mmol) (RS)-6,7-dimethyl-4,5,6,7-tetrahydro-thieno[2,3-c]pyridine and 25 ml of water is mixed batchwise with a total of 2.23 ml bromine/6.7 g KBr in 15 ml of water while cooling with an ice bath. After 30 min the mixture is combined with methylene chloride, the aqueous phase is separated off and the organic phase is concentrated. The crude product is reacted further without any further purification.

$R_t$ value: 0.94 min (Method B)

$C_9H_{13}BrNS \times HBr$ (246.168)

Mass spectrum: $(M+H)^+ = 246/248$ (d) Methyl (RS)-6,7-dimethyl-4,5,6,7-tetrahydro-thieno[2,3-c]pyridine-2-carboxylate A mixture of 2.0 g (6.1 mmol) (RS)-2-bromo-6,7-dimethyl-4,5,6,7-tetrahydro-thieno[2,3-c]pyridine×HBr, 2.0 g (24 mmol) sodium acetate and 100 ml of methanol is combined with 15 mg (0.067 mmol) palladium acetate, 150 mg (0.27 mmol) 1,1'-bis(diphenylphosphino)ferrocene and 2.6 ml (18 mmol) triethylamine and carbonylated for 3.5 h at 80° C. under 5 bar of CO atmosphere. Then the mixture is filtered off, concentrated, combined with sat. $NaHCO_3$ solution and methylene chloride and the resulting emulsion is filtered through Celite. The aqueous phase is separated off and extracted 2× with methylene chloride and the combined organic phases are dried with $Na_2SO_4$ and concentrated. The crude product is reacted further without any further purification.

$R_t$ value: 0.84 min (Method B)

$C_{11}H_{15}NO_2S$ (225.308)

Mass spectrum: $(M+H)^+ = 226$ (e) (3SR,4SR)-5-Chloro-thiophene-2-carboxylic acid-[4-methoxy-1-({RS}-6,7-dimethyl-4,5,6,7-tetrahydro-thieno[2,3-c]pyridine-2-carbonyl)-pyrrolidin-3-yl]-amide (as the trifluoroacetate salt)

Methyl (RS)-6,7-dimethyl-4,5,6,7-tetrahydro-thieno[2,3-c]pyridine-2-carboxylate is saponified with lithium hydroxide analogously to Example 6a and then reacted analogously to Example 1b with (3SR,4SR)-3-[(5-chloro-thiophene-2-carbonyl)-amino]-4-methoxy-pyrrolidine and HATU as coupling reagent to obtain the title compound.

$R_t$ value: 1.01 min (Method B)

$C_{20}H_{24}ClN_3O_3S_2 \times CF_3CO_2H$ (454.00)

Mass spectrum: $(M+H)^+ = 454/456$ (chlorine isotopes)

EXAMPLE 60

(3SR,4SR)-5-Chloro-thiophene-2-carboxylic acid-{1-[(8SR)-6,8-dimethyl-5,6,7,8-tetrahydro-4H-thieno[2,3-d]azepine-2-carbonyl]-4-methoxy-pyrrolidin-3-yl}-amide (as the trifluoroacetate salt)

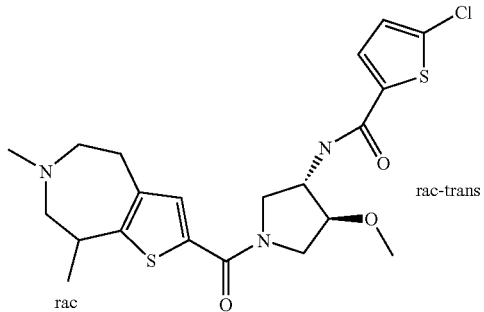

(a) 6,8-Dimethyl-4,5,7,8-tetrahydro-4H-thieno[2,3-d]azepine 300 mg (7.9 mmol) lithium aluminum hydride are placed in 4 ml THF and slowly combined with a solution of 300 mg (0.9 mmol) ethyl 2-bromo-8-methyl-4,5,7,8-tetrahydro-thieno[2,3-d]azepine-6-carboxylate (prepared analogously to US 2006/0003990) in 6 ml THF at RT. The mixture is stirred at RT until the development of gas cases and is then refluxed for 1.5 hours. Then the mixture is cooled in a bath of ice and water and mixed with sat. sodium sulphate solution.

The undissolved material is filtered off, the filtrate is acidified with 1N hydrochloric acid and extracted twice with ethyl acetate. This organic phase is discarded. The aqueous phase is made basic and extracted three times with ethyl acetate. The combined organic phases are dried on sodium sulphate, filtered and evaporated down i. vac.

$R_t$ value: 0.88 min (Method F)

$C_{10}H_{15}NS$ (181.30)

Mass spectrum: $(M+H)^+ = 182$ (b) 2-Bromo-6,8-dimethyl-4,5,6,7-tetrahydro-4H-thieno[2,3-d]azepine 156 mg (0.9 mmol) 6,8-dimethyl-4,5,7,8-tetrahydro-4H-thieno[2,3-d]azepine are placed in a mixture of 1.5 ml glacial acetic acid and 1.5 ml chloroform and combined with 155 mg (0.9 mmol) N-bromosuccinimide. The mixture is stirred for three hours at RT, then 20 mg N-bromosuccinimide are added and the mixture is stirred for a further hour at RT. Then it is mixed with water and extracted twice with ethyl acetate. The extract is discarded. The aqueous phase is made alkaline and extracted three times with ethyl acetate. The combined organic phases are dried on sodium sulphate and evaporated down i. vac.

$R_t$ value: 1.12 min (Method F)

$C_{10}H_{14}BrNS$ (260.19)

Mass spectrum: $(M+H)^+ = 260/262$ (bromine isotopes)

(c) Methyl 6,8-dimethyl-4,5,6,7-tetrahydro-4H-thieno[2,3-d]azepine-2-carboxylate Prepared analogously to Example 26e from 2-bromo-6,8-dimethyl-4,5,6,7-tetrahydro-4H-thieno[2,3-d]azepine.

R$_t$ value: 0.94 min (Method F)

C$_{12}$H$_{17}$NO$_2$S (239.33)

Mass spectrum: (M+H)$^+$=240

(d) 6,8-Dimethyl-4,5,6,7-tetrahydro-4H-thieno[2,3-d]azepine-2-carboxylic acid

Prepared analogously to Example 45b from methyl 6,8-dimethyl-4,5,6,7-tetrahydro-4H-thieno[2,3-d]azepine-2-carboxylate.

R$_t$ value: 0.66 min (Method F)

C$_{11}$H$_{15}$NO$_2$S (225.31)

Mass spectrum: (M+H)$^+$=226

(e) (3SR,4SR)-5-Chloro-thiophene-2-carboxylic acid-{1-[(8SR)-6,8-dimethyl-5,6,7,8-tetrahydro-4H-thieno[2,3-d]azepine-2-carbonyl]-4-methoxy-pyrrolidin-3-yl}-amide (as the trifluoroacetate salt)

Prepared analogously to Example 1b from 6,8-dimethyl-4,5,6,7-tetrahydro-4H-thieno[2,3-d]azepine-2-carboxylic acid and (3SR,4SR)-3-[(5-chloro-thiophene-2-carbonyl)-amino]-4-methoxy-pyrrolidine with HATU as coupling reagent.

R$_t$ value: 1.14 min (Method F)

C$_{21}$H$_{26}$ClN$_3$O$_2$S$_2$×CF$_3$CO$_2$H (468.04)

Mass spectrum: (M+H)$^+$=468/470 (chlorine isotopes)

The following compounds may be prepared analogously:

| N°. | Structural formula / Name | Mass peak(s) | R$_f$ value or R$_t$ |
|---|---|---|---|
| 61 | (2S,4R)-4-[(5-chloro-thiophene-2-carbonyl)-amino]-1-(4,6-dimethyl-5,6,7,8-tetrahydro-4H-thieno[2,3-d]azepine-2-carbonyl)-pyrrolidine-2-carboxylate methyl (as the trifluoroacetate salt) | (M + H)$^+$ = 496/498 (chlorine isotopes) | R$_t$ value = 1.17 min (Method F) |
| 65 | (3R,5S)-5-chloro-thiophene-2-carboxylic acid-[1-(4,6-dimethyl-5,6,7,8-tetrahydro-4H-thieno[2,3-d]azepine-2-carbonyl)-5-hydroxymethyl-pyrrolidin.3.yl]-amide (as the trifluoroacetate salt) | (M + H)$^+$ = 468/470 (chloride isotopes) | R$_t$ value = 1.42 min (Method F) |
| 67 | (3R,5S)-5-chloro-thiophene-2-carboxylic acid-[1-(6,8-dimethyl-5,6,7,8-tetrahydro-4H-thieno[2,3-d]azepine-2-carbonyl)-5-methoxymethyl-pyrrolidin-3-yl]-amide | (M + H)$^+$ = 482/484 (chlorine isotopes) | R$_t$ value = 0.72 min (Method G) |

EXAMPLE 70

(3R,5S)-5-Chloro-thiophene-2-carboxylic acid-{1-[(4SR)-4-methoxy-6-methyl-5,6,7,8-tetrahydro-4H-thieno[2,3-d]azepine-2-carbonyl]-4-methoxy-pyrrolidin-3-yl}-amide (as the trifluoroacetate salt)

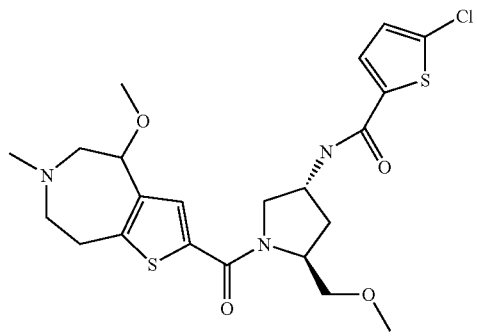

(a) 4-Methoxy-6-methyl-5,6,7,8-tetrahydro-4H-thieno[2,3-d]azepine

Prepared analogously to Example 60a from ethyl 4-methoxy-4,5,7,8-tetrahydro-thieno[2,3-d]azepin-6-carboxylate (US 2006/0003990) by reduction with lithium aluminum hydride.

$R_t$ value: 0.97 min (Method F)
$C_{10}H_{15}NOS$ (197.30)
Mass spectrum: $(M+H)^+=198$ (b) 2-Bromo-4-methoxy-6-methyl-5,6,7,8-tetrahydro-4H-thieno[2,3-d]azepine Prepared analogously to Example 60b from 4-methoxy-6-methyl-5,6,7,8-tetrahydro-4H-thieno[2,3-d]azepine.

$R_t$ value: 1.04 min (Method F)
$C_{10}H_{14}BrNOS$ (276.19)
Mass spectrum: $(M+H)^+=276/278$ (bromine isotopes)

(c) Methyl 4-methoxy-6-methyl-5,6,7,8-tetrahydro-4H-thieno[2,3-d]azepine-2-carboxylate Prepared analogously to Example 26e from 2-bromo-4-methoxy-6-methyl-5,6,7,8-tetrahydro-4H-thieno[2,3-d]azepine.

$R_t$ value: 0.87 min (Method F)
$C_{12}H_{17}NO_3S$ (255.33)
Mass spectrum: $(M+H)^+=256$ (d) 4-Methoxy-6-methyl-5,6,7,8-tetrahydro-4H-thieno[2,3-d]azepine-2-carboxylic acid (as hydrochloride salt)

Prepared analogously to Example 45b from methyl 4-methoxy-6-methyl-5,6,7,8-tetrahydro-4H-thieno[2,3-d]azepine-2-carboxylate.

$R_t$ value: 0.55 min (Method F)
$C_{11}H_{15}NO_3S$ (241.31)
Mass spectrum: $(M+H)^+=242$ (e) 4(3R,5S)-5-Chloro-thiophene-2-carboxylic acid-{1-[(4SR)-4-methoxy-6-methyl-5,6,7,8-tetrahydro-4H-thieno[2,3-d]azepine-2-carbonyl]-4-methoxy-pyrrolidin-3-yl}-amide (as the trifluoroacetate salt)

Prepared analogously to Example 1b from 4-methoxy-6-methyl-5,6,7,8-tetrahydro-4H-thieno[2,3-d]azepine-2-carboxylic acid (as hydrochloride salt).

$R_t$ value: 1.16 min (Method F)
$C_{22}H_{28}ClN_3O_4S_2$ (498.07)
Mass spectrum: $(M+H)^+=498/500$ (chlorine isotopes)

The following compounds may be prepared analogously:

| N°. | Structural formula / Name | Mass peak(s) | $R_f$ value or $R_t$ |
|---|---|---|---|
| 71 | (3R,5S)-5-chloro-thiophene-2-carboxylic acid-{5-methoxymethyl-1-[(4SR)-4-methoxy-6-methyl-4,5,6,7-tetrahydro-thieno[2,3-c]pyridine-2-carbonyl]-pyrrolidin-3-yl}-amide (as the trifluoroacetate salt) | $(M+H)^+ = 484/486$ (chlorine isotopes) | $R_t$ value = 1.14 min (Method F) |
| 72 | (3R,5S)-5-chloro-thiophene-2-carboxylic acid-{5-hydroxymethyl-1-[(4SR)-4-methoxy-6-methyl-4,5,6,7-tetrahydro-thieno[2,3-c]pyridine-2-carbonyl]-pyrrolidin-3-yl}-amide | $(M+H)^+ = 470/472$ (chlorine isotopes) | $R_t$ value = 1.02 min (Method F) |

EXAMPLE 73

(3S,4S)-5-Chloro-thiophene-2-carboxylic acid-[1-(5,6-dimethyl-4,5,6,7-tetrahydro-thieno[2,3-c]-pyridine-2-carbonyl)-4-methoxy-pyrrolidin-3-yl]-amide (as the trifluoroacetate salt)

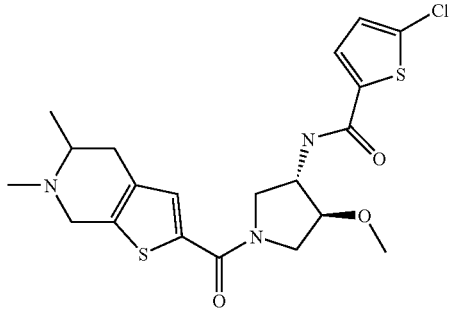

(a) 2-(2-Nitro-propenyl)-thiophene 5.0 g (44.6 mmol) 3-formylthiophene are dissolved together with 8.9 ml (124.8 mmol) nitroethane, 5.3 ml (53.5 mmol) butylamine in 25.1 ml glacial acetic acid (454.7 mmol) and heated to 80° C. After two hours the mixture is cooled and the precipitate formed is suction filtered and washed with copious amounts of water. The crude product thus obtained is dissolved in ethyl acetate, dried on sodium sulphate and evaporated down i. vac.

R value: 1.48 min (Method F)
$C_7H_7NO_2S$ (169.20)
Mass spectrum: $(M+H)^+=170$ (b) 1-Methyl-2-thiophen-2-yl-ethylamine A solution of 3.7 g (21.9 mmol) 2-(2-nitro-propenyl)-thiophene in 50 ml THF is added dropwise to a suspension of 4.1 g (109.3 mmol) lithium aluminium hydride in 150 ml THF. After the addition has ended the mixture is refluxed. After 1.5 hours it is cooled to RT and stirred for another 16 hours. Then the mixture is slowly combined with 10 ml sat. sodium sulphate solution and filtered through Celite. The filtrate thus obtained is evaporated down i. vac.

$R_t$ value: 0.52 min (Method G)
$C_7H_{11}NS$ (141.23)
Mass spectrum: $(M+H)^+=142$ (c) N-(1-Methyl-2-thiophen-2-yl-ethyl)-formamide A solution of 5.9 g (33.4 mmol) 1-methyl-2-thiophen-2-yl-ethylamine in 34.8 ml (417.7 mmol) ethyl formate is refluxed for 16 hours. Then the mixture is cooled and evaporated to dryness i. vac.

$R_t$ value: 1.00 min (Method F)
$C_8H_{11}NOS$ (169.25)
Mass spectrum: $(M+H)^+=170$ (d) 5-Methyl-4,5-dihydro-thieno[2,3-c]-pyridine A solution of 6.6 g (33.1 mmol) N-(1-methyl-2-thiphen-2-yl-ethyl)-formamide in 200 ml acetonitrile is cooled in the ice bath and slowly combined with a solution of 6.1 ml (66.3 mmol) phosphorus oxychloride in 50 ml acetonitrile. The mixture is first of all stirred for a further three hours in the ice bath and then for 16 hours at RT. Then it is poured onto 200 ml of water, made alkaline with 9 g of solid sodium hydroxide and extracted three times with ethyl acetate. The combined organic phases are combined with activated charcoal and sodium sulphate, filtered and evaporated down i. vac.

$R_t$ value: 0.84 min (Method H)
$C_8H_9NS$ (151.23)
Mass spectrum: $(M+H)^+=152$ (e) 5,6-dimethyl-4,5-dihydro-thieno[2,3-c]pyridinium iodide A solution of 4.0 g (26.5 mmol) 5-methyl-4,5-dihydro-thieno[2,3-c]-pyridine in 250 ml acetonitrile is combined at RT with 16.5 ml (264.5 mmol) methyl iodide and stirred for 30 min. The precipitate formed is filtered off and washed with acetonitrile.

$R_t$ value: 0.29 min (Method G)
$C_9H_{12}NSI$ (293.17)
Mass spectrum: $(M)^+=166$ (f) 5,6-dimethyl-4,5,6,7-tetrahydro-thieno[2,3-c]pyridine (as the trifluoroacetate salt)

A mixture of 3.4 g (9.3 mmol) 5,6-dimethyl-4,5-dihydro-thieno[2,3-c]pyridinium iodide in 30 ml of methanol is combined batchwise with 709 mg (18.6 mmol) sodium borohydride at the temperature of an ice bath. The reaction mixture is slowly heated to RT and stirred for 16 hours. Then the mixture is cooled again and combined with 5 ml hydrochloric acid in dioxane (4N). The mixture is evaporated down i. vac. and purified by preparative HPLC (eluant water/acetonitrile/TFA).

$R_t$ value: 0.69 min (Method F)
$C_9H_{13}NS \times CF_3CO_2H$ (167.27)
Mass spectrum: $(M)^+=168$ (g) 2-bromo-5,6-dimethyl-4,5,6,7-tetrahydro-thieno[2,3-c]pyridine 1.0 g (3.6 mmol) 5,6-dimethyl-4,5,6,7-tetrahydro-thieno[2,3-c]pyridine (as the trifluoroacetate salt) are dissolved in 60 ml of water and at the temperature of an ice bath combined with a solution of 1.0 g (8.5 mmol) potassium bromide and 182 µl (3.6 mmol) bromine in 20 ml of water. The mixture is stirred for 2.5 hours in the ice bath and then extracted twice with 100 ml ethyl acetate. The combined organic phases are washed with sat. sodium chloride solution, then dried on sodium sulphate and evaporated down i. vac. The crude product thus obtained is purified by chromatography on silica gel (eluant DCM/methanol 50:1).

$R_t$ value: 0.99 min (Method F)
$C_9H_{12}BrNS$ (246.17)
Mass spectrum: $(M+H)^+=246/248$ (bromine isotopes)

(h) methyl 5,6-dimethyl-4,5,6,7-tetrahydro-thieno[2,3-c]pyridine-2-carboxylate

Prepared analogously to Example 26e from 2-bromo-4-5,6-dimethyl-4,5,6,7-tetrahydro-thieno[2,3-c]-pyridine.

$R_t$ value: 0.63 min (Method G)
$C_{11}H_{15}NO_2S$ (225.31)
Mass spectrum: $(M+H)^+=226$ (i) 5,6-dimethyl-4,5,6,7-tetrahydro-thieno[2,3-c]pyridine-2-carboxylic acid Prepared analogously to Example 45b from methyl 5,6-dimethyl-4,5,6,7-tetrahydro-thieno[2,3-c]pyridine-2-carboxylate.

$R_t$ value: 0.32 min (Method F)
$C_{10}H_{13}NO_2S$ (211.28)
Mass spectrum: $(M+H)^+=212$ (j) (3S,4S)-5-chloro-thiophene-2-carboxylic acid-[1-(5,6-dimethyl-4,5,6,7-tetrahydro-thieno[2,3-c]-pyridine-2-carbonyl)-4-methoxy-pyrrolidin-3-yl]-amide (as the trifluoroacetate salt)

Prepared analogously to Example 1b from 5,6-dimethyl-4,5,6,7-tetrahydro-thieno[2,3-c]pyridine-2-carboxylic acid.

$R_t$ value: 1.17 min (Method F)
$C_{20}H_{24}ClNO_3S_2 \times CF_3CO_2H$ (454.01)
Mass spectrum: $(M+H)^+=454/456$ (chlorine isotopes)

EXAMPLE 76

(3RS,4S)-5-chloro-thiophene-2-carboxylic acid-[4-methoxy-1-(7-methyl-5,6,7,8-tetrahydro-imidazo[1,2-a]pyrazine-2-carbonyl)-pyrrolidin-3-yl]-amide

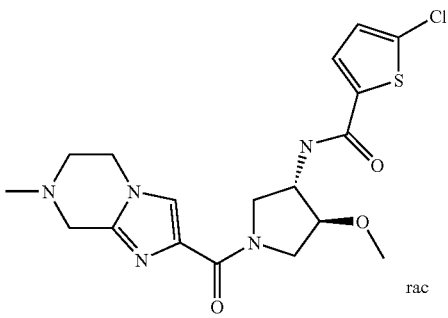

(a) ethyl 7-methyl-5,6,7,8-tetrahydro-imidazo[1,2-a]pyrazine-2-carboxylate (as hydroformate salt)

500.0 mg (2.2 mmol) ethyl 5,6,7,8-tetrahydro-imidazo[1,2-a]pyrazine-2-carboxylate (prepared by liberating the base from the hydrochloride salt) are dissolved in 0.8 ml (21.6 mmol) formic acid and combined with 0.6 ml (8.6 mmol) formalin solution (37% in water) and stirred for 5 hours at a bath temperature of 70° C. After cooling the mixture is evaporated to dryness i. vac.

$R_t$ value: 1.48 min (Method F)
$C_{10}H_{15}N_3O_2 \times HCO_2H$ (209.25)
Mass spectrum: $(M+H)^+=210$ (b) (3RS,4S)-5-chloro-thiophene-2-carboxylic acid-[4-methoxy-1-(7-methyl-5,6,7,8-tetrahydro-imidazo[1,2-a]pyrazine-2-carbonyl)-pyrrolidin-3-yl]-amide Prepared analogously to Example 1 b from 7-methyl5,6,7,8-tetrahydro-imidazo[1,2-a]pyrazine-2-carboxylic acid (prepared from ethyl 7-methyl-5,6,7,8-tetrahydro-imidazo[1,2-a]pyrazine-2-carboxylate (as hydroformate salt) analogously to Example 45b).

$R_t$ value: 1.02 min (Method F)
$C_{18}H_{22}ClN_5O_3S$ (423.92)
Mass spectrum: $(M+H)^+=424/426$ (chlorine isotopes)

EXAMPLE 77

(3R,5S)-5-chloro-thiophene-2-carboxylic acid-[5-methoxymethyl-1-(5-methyl-4,5,6,7-tetrahydro-pyrazolo[1,5-a]pyrarine-2-carbonyl)-pyrrolidin-3-yl]-amide

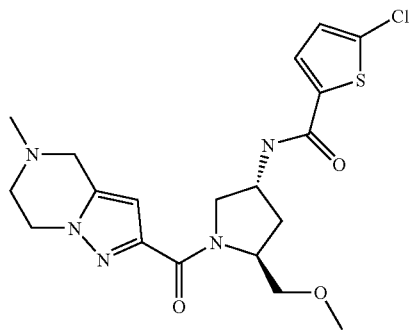

(a) 5-benzyl-2-ethyl 6,7-dihydro-4H-pyrazolo[1,5-a]pyrazine-2,5-dicarboxylate

Prepared analogously to A. M. Venkatesan et al., J. Med. Chem. 2006, 49, 4623 starting from 1-benzyl piperazine-1,3-dicarboxylate.

$R_t$ value: 1.41 min (Method F)
$C_{17}H_{19}N_3O_4$ (329.35)
Mass spectrum: $(M+H)^+=330$ (b) 2-ethyl 4,5,6,7-tetrahydro-pyrazolo[1,5-a]pyrazine-2-carboxylate 200.0 mg (0.7 mmol) 5-benzyl-2-ethyl 6,7-dihydro-4H-pyrazolo[1,5-a]pyrazine-2,5-dicarboxylate are dissolved in 20 ml of methanol, combined with 100 mg palladium/charcoal 10% and hydrogenated at 3 bar hydrogen pressure and RT for 1.5 hours. Then the catalyst is filtered off and the mixture is evaporated down i. vac.

$R_t$ value: 0.49 min (Method F)
$C_9H_{13}N_3O_2$ (195.22)
Mass spectrum: $(M+H)^+=196$ (c) 2-ethyl 5-methyl-4,5,6,7-tetrahydro-pyrazolo[1,5-a]pyrazine-2-carboxylate (as the trifluoroacetate salt)

Prepared analogously to Example 76 a starting from 2-ethyl 4,5,6,7-tetrahydro-pyrazolo[1,5-a]pyrazine-2-carboxylate with subsequent purification of the crude product by preparative HPLC (eluant water/acetonitrile/TFA).

$R_t$ value: 0.56 min (Method F)
$C_{10}H_{15}N_3O_2 \times CF_3CO_2H$ (209.25)
Mass spectrum: $(M+H)^+=210$ (d) 5-methyl-4,5,6,7-tetrahydro-pyrazolo[1,5-a]pyrazine-2-carboxylic acid (as hydrochloride salt)

Prepared analogously to Example 45b starting from 2-ethyl 4,5,6,7-tetrahydro-pyrazolo[1,5-a]pyrazine-2-carboxylate (as the trifluoroacetate salt).

$R_t$ value: 0.24 min (Method F)
$C_8H_{11}N_3O_2 \times HCl$ (181.19)
Mass spectrum: $(M+H)^+=182$ (e) (3R,5S)-5-chloro-thiophene-2-carboxylic acid-[5-methoxymethyl-1-(5-methyl-4,5,6,7-tetrahydro-pyrazolo[1,5-a]pyrarine-2-carbonyl)-pyrrolidin-3-yl]-amide Prepared analogously to Example 1b starting from 5-methyl-4,5,6,7-tetrahydro-pyrazolo[1,5-a]pyrazine-2-carboxylic acid (as hydrochloride salt).

$R_t$ value: 1.08 min (Method F)
$C_{19}H_{24}ClN_5O_3S$ (437.94)
Mass spectrum: $(M+H)^+=438/440$ (chlorine isotopes)

The following compound may be prepared analogously:

| N°. | Structural formula / Name | Mass peak(s) | $R_f$ value or $R_t$ |
|---|---|---|---|
| 98 | ![structure] (3R,5S)-5-chloro-thiophene-2-carboxylic acid-[5-methoxymethyl-1-(6-methyl-5,6,7,8-tetrahydro-4H-1,6,8a-triaza-azulene-2-carbonyl)-pyrrolidin-3-yl]-amide | $(M + H)^+ = 452/454$ (chlorine isotopes) | $R_t$ value = 0.59 min (Method G) |

EXAMPLE 81

(3R,5S)-5-chloro-thiophene-2-carboxylic acid-[5-methoxymethyl-1-(7-methyl-6,7,8,9-tetrahydro-5H-imidazo[1,2-a][1,4]diazepine-2-carbonyl)-pyrrolidin-3-yl]-amide

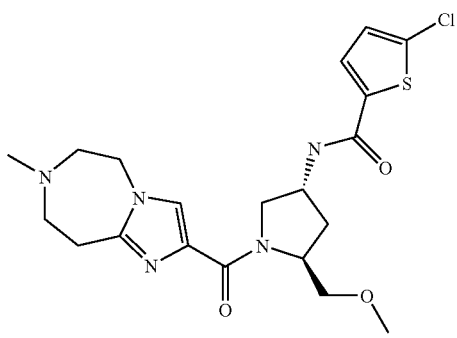

(a) benzyl 5-oxo-[1,4]diazepine-1-carboxylate 4.8 g (42.0 mmol) [1,4]diazepin-5-one are dissolved in 60 ml DCM and at ice bath temperature successively combined with 11.0 ml (83.9 mmol) triethylamine and 6.8 ml (46.2 mmol) benzyl chloroformate. The mixture is heated to RT and kept for three hours at this temperature. Then the mixture is concentrated and combined with water. The aqueous phase is extracted three times with ethyl acetate. The combined organic phases are dried on sodium sulphate, filtered and evaporated down i. vac. The crude product is [purified] by column chromatography on silica gel (eluant DCM/MeOH 95:5→90:10).

$R_t$ value: 1.06 min (Method F)
$C_{13}H_{16}N_2O_3$ (248.28)
Mass spectrum: $(M+H)^+=249$ (b) benzyl 5-imino-[1,4]diazepine-1-carboxylate 1.0 g (4.0 mmol) benzyl 5-oxo-[1,4]diazepine-1-carboxylate are suspended in 1.0 ml (10.6 mmol) dimethylsulphate, stirred for two hours at 90° C. and after cooling dissolved in 10 ml (20 mmol) ammonia solution (2N in methanol). The mixture is stirred for 3.5 hours at RT and then evaporated to dryness.

$R_t$ value: 1.02 min (Method F)
$C_{13}H_{17}N_3O_2$ (247.29)
Mass spectrum: $(M+H)^+=248$ (c) benzyl 2-formyl-5,6,8,9-tetrahydro-imidazo[1,2-a][1,4]diazepine-7-carboxylate 1.0 g (4.0 mmol) benzyl 5-imino-[1,4]diazepine-1-carboxylate are dissolved in 3 ml of ethanol and combined with 2.8 ml (8.1 mmol) sodium methoxide solution (30% in methanol). A solution of 843 mg (4.4 mmol) 2-bromo-3-isopropoxy-propenal in 3 ml of ethanol is added and once the addition has ended the mixture is refluxed for 1.5 hours. Then the mixture is concentrated, the residue is dissolved in 6 ml chloroform and 560 µl (4.0 mmol) triethylamine are added. The reaction mixture is refluxed for 16 hours, then cooled, evaporated down and purified by flash chromatography on silica gel (eluant DCM/methanol 20:1). A product fraction that is still impure is obtained, which is purified by preparative HPLC (eluant water/acetonitrile/conc. ammonia).

$R_t$ value: 0.63 min (Method G)
$C_{16}H_{17}N_3O_3$ (299.32)
Mass spectrum: $(M+H)^+=300$ (d) Benzyl ammonium-5,6,8,9-tetrahydro-imidazo[1,2-a][1,4]diazepine-7-carboxylate-2-carboxylate 107.0 mg (0.36 mmol) benzyl 2-formyl-5,6,8,9-tetrahydro-imidazo[1,2-a][1,4]diazepine-7-carboxylate are dissolved in 1 ml DMSO and combined with a solution of 85 mg (0.55 mmol) sodium dihydrogen sulphate-dihydrate in 0.5 ml of water and cooled in the ice bath. 160 mg (1.4 mmol) sodium chlorate are dissolved in 0.5 ml of water and slowly added dropwise to the educt solution. The mixture is stirred for 30 min and filtered to remove undissolved material. The filtrate is purified by preparative HPLC (water/acetonitrile/conc. ammonia).

$R_t$ value: 0.41 min (Method G)
$C_{16}H_{17}N_3O_4 \times NH_3$ (315.33)
Mass spectrum: $(M+H)^+=316$ (e) 7-benzyl-2-methyl 5,6,8,9-tetrahydro-imidazo[1,2-a][1,4]diazepine-2,7-dicarboxylate 68.0 mg (0.21 mmol) benzyl ammonium-5,6,8,9-tetrahydro-imidazo[1,2-a][1,4]diazepine-7-carboxylate -2-carboxylate are dissolved in 1.5 ml of methanol and combined with 40 µl (0.6 mmol) thionyl chloride in the ice bath. The ice bath is taken away and after 30 minutes the mixture is refluxed for one day. A further 100 µl thionyl chloride are added twice more and the mixture is heated for one more day. Then the reaction mixture is concentrated i. vac. and further reacted as the crude product.

$R_t$ value: 1.15 min (Method F)
$C_{17}H_{19}N_3O_4$ (329.35)
Mass spectrum: $(M+H)^+=330$ (f) methyl 6,7,8,9-tetrahydro-5H-imidazo[1,2-a][1,4]diazepine-2-carboxylate Prepared analogously to Example 77b starting from 7-benzyl-2-methyl 5,6,8,9-tetrahydro-imidazo[1,2-a][1,4]diazepine-2,7-dicarboxylate.

$R_t$ value: 0.36 min (Method G)
$C_9H_{13}N_3O_2$ (195.22)
Mass spectrum: $(M+H)^+=196$ (g) methyl 7-methyl-6,7,8,9-tetrahydro-5H-imidazo[1,2-a][1,4]diazepine-2-carboxylate (as the trifluoroacetate salt)

Prepared analogously to Example 76 a starting from methyl 5,6,8,9-tetrahydro-imidazo[1,2-a][1,4]diazepine-2-carboxylate with subsequent purification by preparative HPLC (eluant water/acetonitrile/TFA).

$R_t$ value: 0.20 min (Method F)
$C_{10}H_{15}N_3O_2 \times CF_3CO_2H$ (209.25)
Mass spectrum: $(M+H)^+=210$ (h) 7-methyl-6,7,8,9-tetrahydro-5H-imidazo[1,2-a][1,4]diazepine-2-carboxylic acid (as hydrochloride salt)

Prepared analogously to Example 45b starting from 2-ethyl 4,5,6,7-tetrahydro-pyrazolo[1,5-a]pyrazine-2-carboxylate (as the trifluoroacetate salt).

$R_t$ value: 0.20 min (Method F)
$C_9H_{13}N_3O_2$ (195.22)
Mass spectrum: $(M+H)^+=196$ (i) (3R,5S)-5-chloro-thiophene-2-carboxylic acid-[5-methoxymethyl-1-(7-methyl-6,7,8,9-tetrahydro-5H-imidazo[1,2-a][1,4]diazepine-2-carbonyl)-pyrrolidin-3-yl]-amide Prepared analogously to Example 1b starting from 7-methyl-6,7,8,9-tetrahydro-5H-imidazo[1,2-a][1,4]diazepine-2-carboxylic acid (as hydrochloride salt).

$R_t$ value: 1.00 min (Method F)
$C_{20}H_{26}ClN_5O_3S$ (451.97)
Mass spectrum: $(M+H)^+=452/454$ (chlorine isotopes)

EXAMPLE 82

(3RS,4SR)-5-chloro-thiophene-2-carboxylic acid-{4-methoxy-1-[(7RS)-7-methoxymethyl-6-methyl-4,5,6,7-tetrahydro-thieno[2,3-c]pyridine-2-carbonyl]-pyrrolidin-3-yl}-amide (as the trifluoroacetate salt)

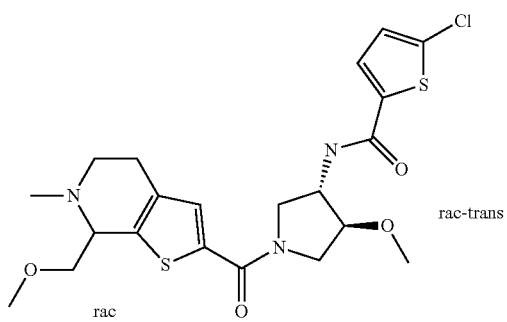

(a) 2-methoxy-N-(2-thiophen-3-yl-ethyl)-acetamide 10.0 g (78.6 mmol) 2-thiophen-3-yl-ethylamine are dissolved in 120 ml THF and at −10° C. combined successively with 7.9 ml (86.5 mmol) methoxyacetic acid chloride and a solution of 21.9 ml (157.2 mmol) triethylamine in 30 ml THF. The mixture is heated to RT and stirred for one hour. Then it is acidified with 2N hydrochloric acid and the mixture is extracted three times with ethyl acetate. The combined organic phases are dried on sodium sulphate, filtered and evaporated down i. vac.

$R_t$ value: 1.01 min (Method F)
$C_9H_{13}NO_2S$ (199.27)
Mass spectrum: $(M+H)^+=200$ (b) 7-methoxymethyl-4,5-dihydro-thieno[2,3-c]pyridine 15.6 g (78.3 mmol) 2-methoxy-N-(2-thiophen-3-yl-ethyl)-acetamide are dissolved in 350 ml chloroform and combined with 35.8 ml (391.4 mmol) phosphorus oxychloride while cooling with an ice bath. The ice bath is removed and the mixture is refluxed for 5 hours. Then it is carefully added to 600 ml of warm sodium hydroxide solution (4N) and the aqueous phase is extracted three times with ethyl acetate. The combined organic phases are dried on sodium sulphate, filtered and evaporated down i. vac. The crude product is purified by flash chromatography on silica gel (eluant DCM/methanol 98:2→95:5).

$R_t$ value: 0.59 min (Method F)
$C_9H_{11}NOS$ (181.26)
Mass spectrum: $(M+H)^+=182$ (c) 7-methoxymethyl-4,5,6,7-tetrahydro-thieno[2,3-c]pyridine 1.0 g (5.5 mmol) 7-methoxymethyl-4,5-dihydro-thieno[2,3-c]pyridine are dissolved in 10 ml of methanol and combined batchwise with 0.4 g (11.0 mmol) sodium borohydride while cooling with an ice bath. The ice bath is removed and the reaction mixture is stirred at RT for two hours. Then it is evaporated down and reacted further as the crude product.

$R_t$ value: 0.75 min (Method F)
$C_9H_{13}NOS$ (183.27)
Mass spectrum: $(M+H)^+=184$ (d) 7-methoxymethyl-6-methyl-4,5,6,7-tetrahydro-thieno[2,3-c]pyridine Prepared analogously to Example 76a starting from 7-methoxymethyl-4,5,6,7-tetrahydro-thieno[2,3-c]pyridine.

$R_t$ value: 0.78 min (Method F)
$C_{10}H_{15}NOS$ (197.30)
Mass spectrum: $(M+H)^+=198$ (e) 2-bromo-7-methoxymethyl-6-methyl-4,5,6,7-tetrahydro-thieno[2,3-c]pyridine Prepared analogously to Example 73g starting from 7-methoxymethyl-6-methyl-4,5,6,7-tetrahydro-thieno[2,3-c]pyridine.

$R_t$ value: 1.04 min (Method F)
$C_{10}H_{14}BrNOS$ (276.19)
Mass spectrum: $(M+H)^+=276/278$ (bromine isotopes)

(f) methyl 7-methoxymethyl-6-methyl-4,5,6,7-tetrahydro-thieno[2,3-c]pyridine-2-carboxylate Prepared analogously to Example 26e starting from 2-bromo-7-methoxymethyl-6-methyl-4,5,6,7-tetrahydro-thieno[2,3-c]pyridine.

$R_t$ value: 0.87 min (Method F)
$C_{12}H_{17}NO_3S$ (255.33)
Mass spectrum: $(M+H)^+=256$ (g) 7-methoxymethyl-6-methyl-4,5,6,7-tetrahydro-thieno[2,3-c]pyridine-2-carboxylic acid (as hydrochloride salt)

Prepared analogously to Example 45b starting from methyl 7-methoxymethyl-6-methyl-4,5,6,7-tetrahydro-thieno[2,3-c]pyridine-2-carboxylate.

$R_t$ value: 0.58 min (Method F)
$C_{11}H_{15}NO_3S \times HCl$ (241.31)
Mass spectrum: $(M+H)^+=242$ (h) (3RS,4SR)-5-chloro-thiophene-2-carboxylic acid-{4-methoxy-1-[(7RS)-7-methoxymethyl-6-methyl-4,5,6,7-tetrahydro-thieno[2,3-c]pyridine-2-carbonyl]-pyrrolidin-3-yl}-amide (as the trifluoroacetate salt)

Prepared analogously to Example 1b starting from 7-methoxymethyl-6-methyl-4,5,6,7-tetrahydro-thieno[2,3-c]pyridine-2-carboxylic acid (as hydrochloride salt).

$R_t$ value: 1.16 min (Method F)
$C_{21}H_{26}ClN_3O_4S_2 \times CF_3CO_2H$ (241.31)
Mass spectrum: $(M+H)^+=484/486$ (chlorine isotopes)

EXAMPLE 84

4-[(5-chloro-thiophene-2-carbonyl)-amino]-1-(6-methyl-5,6,7,8-tetrahydro-4H-thieno[2,3-d]azepine-2-carbonyl)-pyrrolidin-2-yl-methyl (2S,4R)-ethyl-carbamate (as the trifluoroacetate salt)

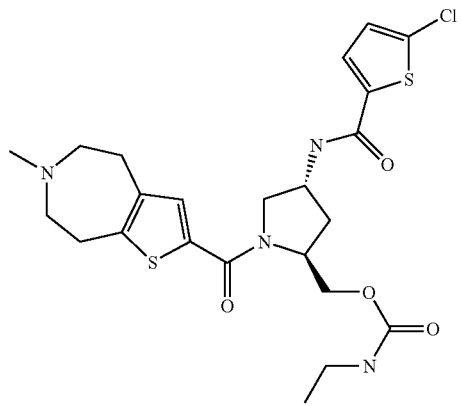

(a) tert. Butyl (2S,4R)-4-[(5-chloro-thiophene-2-carbonyl)-amino]-2-ethylcarbamoyloxymethyl-pyrrolidine-1-carboxylate 120.0 mg (0.3 mmol) tert. Butyl (2S,4R)-4-[(5-chloro-thiophene-2-carbonyl)-amino]-2-hydroxymethyl-pyrrolidine-1-carboxylate are refluxed in 5 ml of toluene with 30 μl (0.38 mmol) ethylisocyanate for three hours. Then 100 μl ethyl isocyanate are added three times at three hour intervals and the mixture is refluxed for a further 16 hours. Then the mixture is cooled, evaporated to dryness and purified by flash chromatography on silica gel (eluant DCM/methanol 100:3).

$R_t$ value: 1.52 min (Method F)
$C_{18}H_{26}ClN_3O_5S$ (431.93)
Mass spectrum: $(M+H)^+$=432/434 (chlorine isotopes)

(b) 4-[(5-chloro-thiophene-2-carbonyl)-amino]-pyrrolidin-2-yl-methyl (2S,4R)-ethyl-carbamate (as the trifluoroacetate salt)

77.0 mg (0.3 mmol) tert. Butyl (2S,4R)-4-[(5-chloro-thiophene-2-carbonyl)-amino]-2-ethylcarbamoyloxymethyl-pyrrolidine-1-carboxylate are dissolved in 1.0 ml of a mixture of TFA and DCM (v/v 1:1) and stirred for three hours at RT. Then the reaction mixture is evaporated to dryness.

$R_t$ value: 1.04 min (Method F)
$C_{13}H_{18}ClN_3O_3S \times CF_3CO_2H$ (331.82)
Mass spectrum: $(M+H)^+$=332/334 (chlorine isotopes)

(c) 4-[(5-chloro-thiophene-2-carbonyl)-amino]-1-(6-methyl-5,6,7,8-tetrahydro-4H-thieno[2,3-d]azepine-2-carbonyl)-pyrrolidin-2-yl-methyl (2S,4R)-ethyl-carbamate (as the trifluoroacetate salt)

Prepared analogously to Example 1b from 4-[(5-chloro-thiophene-2-carbonyl)-amino]-pyrrolidin-2-yl-methyl (2S,4R)-ethyl-carbamate (as the trifluoroacetate salt)

$R_t$ value: 1.17 min (Method F)
$C_{23}H_{29}ClN_4O_4S_2 \times CF_3CO_2H$ (331.82)
Mass spectrum: $(M+H)^+$=525/527 (chlorine isotopes)

The following compounds may be prepared analogously:

| N°. | Structural formula / Name | Mass peak(s) | $R_f$ value or $R_t$ |
|---|---|---|---|
| 85 | 4-[(5-chloro-thiophene-2-carbonyl)-amino]-1-(6-methyl-5,6,7,8-tetrahydro-4H-thieno[2,3-d]azepine-2-carbonyl)-pyrrolidin-2-yl-methyl (2S,4R)-methyl-carbamate (as the trifluoroacetate salt) | $(M + H)^+$ = 511/513 (chlorine isotopes) | $R_t$ value = 1.14 min (Method F) |
| 86 | 4-[(5-chloro-thiophene-2-carbonyl)-amino]-1-(6-methyl-5,6,7,8-tetrahydro-4H-thieno[2,3-d]azepine-2-carbonyl)-pyrrolidin-2-yl-methyl (2S,4R)-dimethyl-carbamate (as the trifluoroacetate salt) | $(M + H)^+$ = 525/527 (chlorine isotopes) | $R_t$ value = 1.16 min (Method F) |

EXAMPLE 90

(3R,5S)-5-chloro-thiophene-2-carboxylic acid-[5-(acetylamino-methyl)-1-(6-methyl-5,6,7,8-tetrahydro-4H-thieno[2,3-d]azepine-2-carbonyl)-pyrrolidin-3-yl]-amide

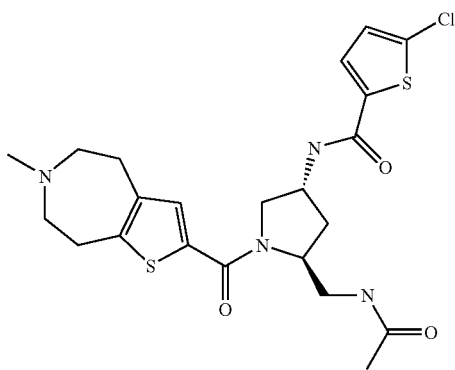

(a) tert. Butyl (2S,4R)-4-[(5-chloro-thiophene-2-carbonyl)-amino]-2-methanesulphonyloxymethyl-pyrrolidine-1-carboxylate 278.0 mg (0.8 mmol) tert. Butyl (2S,4R)-4-[(5-chloro-thiophene-2-carbonyl)-amino]-2-hydroxymethyl-pyrrolidine-1-carboxylate are dissolved in 6 ml DCM and combined with 216 µl (1.5 mmol) triethylamine. 89 µl (1.2 mmol) methanesulphonic acid chloride are added while cooling with the ice bath. The reaction mixture is heated to RT and stirred for two hours. Then it is mixed with water and extracted three times with ethyl acetate. The combined organic phases are dried on sodium sulphate, filtered and evaporated down i. vac.

$R_t$ value: 1.50 min (Method F)
$C_{16}H_{23}ClN_2O_6S_2$ (438.95)
Mass spectrum: $(M+H)^+$=439/441 (chlorine isotopes)

(b) tert. Butyl (2S,4R)-2-azidomethyl-4-[(5-chloro-thiophene-2-carbonyl)-amino]-pyrrolidine-1-carboxylate 330.0 mg (0.75 mmol) tert. Butyl (2S,4R)-4-[(5-chloro-thiophene-2-carbonyl)-amino]-2-methanesulphonyloxymethyl-pyrrolidine-1-carboxylate are dissolved in 20 ml DMF and combined with 146.6 mg (2.3 mmol) sodium azide. The mixture is stirred at 50° C. for 16 hours. Then a further 73 mg (1.12 mmol) sodium azide are added and the mixture is stirred for a further two hours at 50° C. Then it is concentrated i. vac. The residue is combined with water/sat. Saline solution and extracted three times with ethyl acetate. The combined organic phases are dried on sodium sulphate, filtered and evaporated down i. vac.

$R_t$ value: 1.64 min (Method F)
$C_{15}H_{20}ClN_5O_3S$ (385.87)
Mass spectrum: (M+H—BOC)$^+$=285/287 (chlorine isotopes)

(c) tert. Butyl (2S,4R)-2-aminomethyl-4-[(5-chloro-thiophene-2-carbonyl)-amino]-pyrrolidine-1-carboxylate 290.0 mg (0.75 mmol) tert. Butyl (2S,4R)-2-azidomethyl-4-[(5-chloro-thiophene-2-carbonyl)-amino]-pyrrolidine-1-carboxylate are dissolved in a mixture of 4 ml THF and 0.4 ml of water and combined with 0.3 g (1.1 mmol) triphenylphosphine. The reaction mixture is stirred at RT for 16 hours. Then the mixture is concentrated i. vac., combined with water and dil. Sodium hydroxide solution and extracted three times with DCM. The combined organic phases are dried on sodium sulphate, filtered and evaporated down i. vac. The crude product is purified by flash chromatography on silica gel (eluant DCM/methanol 9:1→1:1).

$R_t$ value: 1.25 min (Method F)
$C_{15}H_{22}ClN_3O_3S$ (359.87)
Mass spectrum: $(M+H)^+$=360/362 (chlorine isotopes)

(d) tert. Butyl (2S,4R)-2-acetylaminomethyl-4-[(5-chloro-thiophene-2-carbonyl)-amino]-pyrrolidine-1-carboxylate 70.0 mg (0.2 mmol) tert. Butyl (2S,4R)-2-aminomethyl-4-[(5-chloro-thiophene-2-carbonyl)-amino]-pyrrolidine-1-carboxylate are dissolved in 5 ml DCM and combined successively at −10° C. with 15.4 µl (0.2 mmol) acetyl chloride and 67 µl (0.4 mmol) DIPEA. The mixture is stirred for two hours at 0° C. Then it is made weakly acidic by the careful addition of dil. hydrochloric acid and extracted three times with ethyl acetate. The combined organic phases are dried on sodium sulphate, filtered and evaporated down i. vac.

$R_t$ value: 1.36 min (Method F)
$C_{17}H_{24}ClN_3O_4S$ (401.91)
Mass spectrum: $(M+H)^+$=402/404 (chlorine isotopes)

(e) (3R,5S)-5-chloro-thiophene-2-carboxylic acid-[5-(acetylamino-methyl)-1-(6-methyl-5,6,7,8-tetrahydro-4H-thieno[2,3-d]azepine-2-carbonyl)-pyrrolidin-3-yl]-amide Prepared analogously to Example 1b from tert. Butyl (2S,4R)-2-acetylaminomethyl-4-[(5-chloro-thiophene-2-carbonyl)-amino]-pyrrolidine-1-carboxylate.

$R_t$ value: 0.60 min (Method G)
$C_{22}H_{27}ClN_4O_3S_2$ (495.06)
Mass spectrum: $(M+H)^+$=495/497(chlorine isotopes)

The following compounds may be prepared analogously:

| N°. | Structural formula / Name | Mass peak(s) | $R_f$ value or $R_t$ |
|---|---|---|---|
| 93 | (3R,5S)-5-chloro-thiophene-2-carboxylic acid-[5-[(2-methoxy-acetylamino)-methyl]-1-(6-methyl-5,6,7,8-tetrahydro-4H-thieno{[2,3-d]azepine-2-carbonyl}-pyrrolidin-3-yl]-amide (as the trifluoroacetate salt) | $(M + H)^+ = 525/527$ (chlorine isotopes) | $R_t$ value = 1.08 min (Method F) |
| 94 | methyl (2S,4R)-4-[(5-chloro-thiophene-2-carbonyl)-amino]-1-(6-methyl-5,6,7,8-tetrahydro-4H-thieno[2,3-d]azepine-2-carbonyl)-pyrrolidin-2-ylmethyl]-carbamate (as the trifluoroacetate salt) | $(M + H)^+ = 524/526$ (chlorine isotopes) | $R_t$ value = 1.08 min (Method F) |
| 95 | (3R,5S)-5-chloro-thiophene-2-carboxylic acid-[5-[(3-ethyl-ureido)-methyl]-1-(6-methyl-5,6,7,8-tetrahydro-4H-thieno[2,3-d]azepine-2-carbonyl)-pyrrolidin-3-yl]-amide (as the trifluoroacetate salt) | $(M + H)^+ = 511/513$ (chlorine isotopes) | $R_t$ value = 1.12 min (Method F) |
| 96 | (3R,5S)-5-chloro-thiophene-2-carboxylic acid-[5-(methanesulphonylamino-methyl)-1-(6-methyl-5,6,7,8-tetrahydro-4H-thieno[2,3-d]azepine-2-carbonyl)-pyrrolidin-3-yl]-amide (as the trifluoroacetate salt) | $(M + H)^+ = 531/533$ (chlorine isotopes) | $R_t$ value = 1.38 min (Method F) |

EXAMPLE 89

(3R,5S)-5-chloro-thiophene-2-carboxylic acid-[5-dimethylaminomethyl-1-(6-methyl-5,6,7,8-tetrahydro-4H-thieno[2,3-d]azepine-2-carbonyl)-pyrrolidin-3-yl]-amide

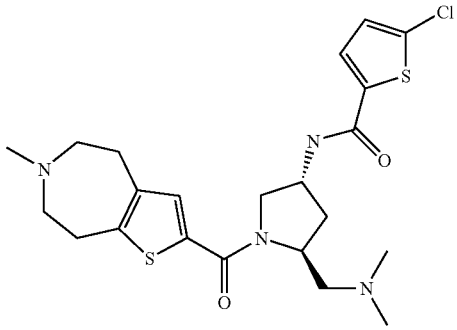

(a) tert. Butyl (2S,4R)-4-[(5-chloro-thiophene-2-carbonyl)-amino]-2-dimethylaminomethyl-pyrrolidine-1-carboxylate 70.0 mg (0.2 mmol) tert. Butyl (2S,4R)-2-aminomethyl-4-[(5-chloro-thiophene-2-carbonyl)-amino]-pyrrolidine-1-carboxylate are suspended in 4 ml of methanol and adjusted to pH 6 with glacial acetic acid. Then 34 µl (0.45 mmol) formaldehyde solution (37% in water) are added and the mixture is stirred for 30 min at RT. Then 95 mg (0.45 mmol) sodium triacetoxyborohydride is added batchwise and the mixture is stirred for 16 hours at RT. Then the reaction mixture is poured onto sat. sodium hydrogen carbonate solution and extracted three times with ethyl acetate. The combined organic phases are dried on sodium sulphate, filtered and evaporated down i. vac.

$R_t$ value: 1.35 min (Method F)
$C_{17}H_{26}ClN_3O_3S$ (387.93)
Mass spectrum: $(M+H)^+=388/390$ (chlorine isotopes)

(b) (3R,5S)-5-chloro-thiophene-2-carboxylic acid-[5-dimethylaminomethyl-1-(6-methyl-5,6,7,8-tetrahydro-4H-thieno[2,3-d]azepine-2-carbonyl)-pyrrolidin-3-yl]-amide Prepared analogously to Example 1b from tert. Butyl (2S,4R)-4-[(5-chloro-thiophene-2-carbonyl)-amino]-2-dimethylaminomethyl-pyrrolidine-1-carboxylate.

$R_t$ value: 0.64 min (Method G)
$C_{22}H_{29}ClN_4O_2S_2$ (481.08)
Mass spectrum: $(M+H)^+=481/483$ (chlorine isotopes)

EXAMPLE 91

(3R,5S)-5-chloro-thiophene-2-carboxylic acid-[5-methoxymethyl-1-[(4S)-6-methyl-5,6,7,8-tetrahydro-4H-4-methoxy-thieno[2,3-d]azepine-2-carbonyl]-pyrrolidin-3-yl]-amide

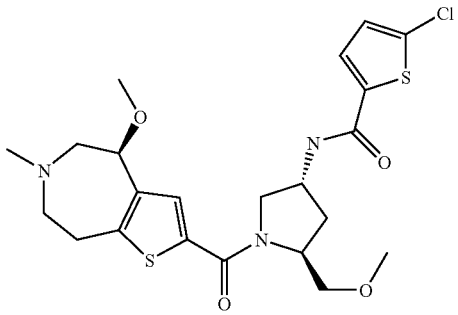

(a) ethyl (S)-4-hydroxy-4,5,7,8-tetrahydro-thieno[2,3-d]azepin-6-carboxylate 3.86 g (16.1 mmol) ethyl 4-oxo-4,5,7,8-tetrahydro-thieno[2,3-d]azepine-6-carboxylate (prepared analogously to WO2007/84622) in 50 ml methylene chloride are combined, under argon, at −25° C., first with 1.92 ml of a 1.0 M toluene solution of (S)-3,3-diphenyl-1-methyl-tetrahydro-1H,3H-pyrrolo[1,2-c][1,3,2]oxazaborolidine and then with 20.2 ml of a 2 M borane-dimethylsulphide complex-toluene solution in 70 ml methylene chloride, and chilled to −18° C. for 3 days. Then sat. NH$_3$Cl solution is added and the mixture is extracted 3× with methylene chloride. The combined organic phases are dried with NaSO$_4$, concentrated and the crude product is purified by flash chromatography on silica gel (eluant DCM/methanol 95:5).

$R_t$ value: 1.15 min (Method F)
$C_{11}H_{15}NO_3S$ (241.31)
Mass spectrum: $(M+H)^+=242$ (b) ethyl (S)-4-methoxy-4,5,7,8-tetrahydro-thieno[2,3-d]azepine-6-carboxylate 3.39 g (14.0 mmol) ethyl (S)-4-hydroxy-4,5,7,8-tetrahydro-thieno[2,3-d]azepine-6-carboxylate in 40 ml THF are mixed batchwise with 0.86 g of 60% NaH mineral oil dispersion while cooling with an ice bath, the mixture is stirred for 15 min and then 1.07 ml methyl iodide are slowly added dropwise. The mixture is stirred for 1 h, poured onto ice water and extracted 3× with ethyl acetate. The combined organic phases are dried with NaSO$_4$ and concentrated.

$R_t$ value: 1.38 min (Method F)
$C_{12}H_{17}NO_3S$ (241.31)
Mass spectrum: $(M+H)^+=256$ (c) (3R,5S)-5-chloro-thiophene-2-carboxylic acid-[5-methoxymethyl-1-[(4S)-6-methyl-5,6,7,8-tetrahydro-4H-4-methoxy-thieno[2,3-d]azepine-2-carbonyl]-pyrrolidin-3-yl]-amide Prepared from ethyl (S)-4-methoxy-4,5,7,8-tetrahydro-thieno[2,3-d]azepin-6-carboxylate analogously to the following synthesis sequence: 60a, 60b, 26e, 45b, 53.

$R_t$ value: 0.67 min (Method G)
$C_{22}H_{28}ClN_3O_3S_2$ (498.06)
Mass spectrum: $(M+H)^+=498/500$ (chlorine isotopes)

The following compounds may be prepared analogously:

| N°. | Structural formula / Name | Mass peak(s) | $R_f$ value or $R_t$ |
|---|---|---|---|
| 92 | (2S,4R)-4-[(5-chloro-thiophene-2-carbonyl)-amino]-1-((S)-4-methoxy-6-methyl-5,6,7,8-tetrahydro-4H-thieno[2,3-d]azepine-2-carbonyl)-pyrrolidine-2-carboxylic acid methylamide | $(M + H)^+ = 511/513$ (chlorine isotopes) | $R_t$ value = 0.60 min (Method G) |
| 97 | 5-chloro-thiophene-2-carboxylic acid[(3R,5S)-5-methoxymethyl-1-((R)-4-methoxy-6-methyl-5,6,7,8-tetrahydro-4H-thieno[2,3-d]azepine-2-carbonyl)-pyrrolidin-3-yl]-amide | $(M + H)^+ = 498/500$ (chlorine isotopes) | $R_t$ value = 0.67 min (Method F) |

The Examples that follow describe the preparation of some pharmaceutical formulations which contain as active substance any desired compound of general formula I:

EXAMPLE A

Dry Ampoule Containing 75 mg of Active Substance per 10 ml
Composition:

| | |
|---|---|
| Active substance | 75.0 mg |
| Mannitol | 50.0 mg |
| water for injections | ad 10.0 ml |

Preparation:

Active substance and mannitol are dissolved in water. After packaging the solution is freeze-dried. To produce the solution ready for use for injections, the product is dissolved in water.

EXAMPLE B

Dry Ampoule Containing 35 mg of Active Substance per 2 ml
Composition:

| | |
|---|---|
| Active substance | 35.0 mg |
| Mannitol | 100.0 mg |
| water for injections | ad 2.0 ml |

Preparation:

Active substance and mannitol are dissolved in water. After packaging, the solution is freeze-dried.

To produce the solution ready for use, the product is dissolved in water for injections.

Example C

Tablet Containing 50 mg of Active Substance
Composition:

| | |
|---|---|
| (1) Active substance | 50.0 mg |
| (2) Lactose | 98.0 mg |
| (3) Maize starch | 50.0 mg |
| (4) Polyvinylpyrrolidone | 15.0 mg |
| (5) Magnesium stearate | 2.0 mg |
| | 215.0 mg |

Preparation:

(1), (2) and (3) are mixed together and granulated with an aqueous solution of (4). (5) is added to the dried granulated material. From this mixture tablets are pressed, biplanar, faceted on both sides and with a dividing notch on one side. Diameter of the tablets: 9 mm.

EXAMPLE D

Tablet Containing 350 mg of Active Substance

Composition:

| | | |
|---|---|---|
| (1) Active substance | 350.0 | mg |
| (2) Lactose | 136.0 | mg |
| (3) Maize starch | 80.0 | mg |
| (4) Polyvinylpyrrolidone | 30.0 | mg |
| (5) Magnesium stearate | 4.0 | mg |
| | 600.0 | mg |

Preparation:

(1), (2) and (3) are mixed together and granulated with an aqueous solution of (4). (5) is added to the dried granulated material. From this mixture tablets are pressed, biplanar, faceted on both sides and with a dividing notch on one side. Diameter of the tablets: 12 mm.

EXAMPLE E

Capsules Containing 50 mg of Active Substance

Composition:

| | | |
|---|---|---|
| (1) Active substance | 50.0 | mg |
| (2) Dried maize starch | 58.0 | mg |
| (3) Powdered lactose | 50.0 | mg |
| (4) Magnesium stearate | 2.0 | mg |
| | 160.0 | mg |

Preparation:

(1) is triturated with (3). This trituration is added to the mixture of (2) and (4) with vigorous mixing.

This powder mixture is packed into size 3 hard gelatine capsules in a capsule filling machine.

EXAMPLE F

Capsules Containing 350 mg of Active Substance

Composition:

| | | |
|---|---|---|
| (1) Active substance | 350.0 | mg |
| (2) Dried maize starch | 46.0 | mg |
| (3) Powdered lactose | 30.0 | mg |
| (4) Magnesium stearate | 4.0 | mg |
| | 430.0 | mg |

Preparation:

(1) is triturated with (3). This trituration is added to the mixture of (2) and (4) with vigorous mixing.

This powder mixture is packed into size 0 hard gelatine capsules in a capsule filling machine.

EXAMPLE G

Suppositories Containing 100 mg of Active Substance 1 suppository contains:

| | | |
|---|---|---|
| Active substance | 100.0 | mg |
| Polyethyleneglycol (M.W. 1500) | 600.0 | mg |
| Polyethyleneglycol (M.W. 6000) | 460.0 | mg |
| Polyethylenesorbitan monostearate | 840.0 | mg |
| | 2,000.0 | mg |

Preparation:

The polyethyleneglycol is melted together with polyethylenesorbitan monostearate. At 40° C. the ground active substance is homogeneously dispersed in the melt. It is cooled to 38° C. and poured into slightly chilled suppository moulds.

What is claimed is:

1. A compound of formula (I)

$$\begin{array}{c} H \\ | \\ N-L^2-M, \\ \text{E} \diagdown R^5 \\ L \diagup \diagdown G \\ D-L^1-N \diagdown J \diagup R^4 \end{array} \quad (I)$$

wherein

D denotes a substituted bicyclic ring system of formula (IIa), (IIb) or (IIc)

(IIa)

$$\begin{array}{c} K^2-K^1 \diagup A^1 \\ X \diagup \diagdown \diagup \diagdown \\ K^3-K^4 \diagdown A^3 = A^2 \end{array} \text{ or }$$

(IIb)

$$\begin{array}{c} K^2-K^1 \diagup A^4 \\ X \diagup \diagdown \diagup \diagdown \\ K^3-K^4 \diagdown A^5 \end{array} \text{ or }$$

(IIc)

$$\begin{array}{c} K^2-K^1 \diagup A^1 \\ X \diagup \diagdown \diagup \diagdown \\ K^3-K^4 \diagdown N \diagdown A^2 \end{array}$$

wherein $K^1$ and $K^4$
each independently denote a bond, a —$CH_2$, —$CHR^{7a}$, —$CR^{7b}R^{7c}$ or a —C(O) group, and wherein
$R^{7a}/R^{7b}/R^{7c}$
each independently denote a fluorine atom, a hydroxy, $C_{1-5}$-alkyloxy, amino, $C_{1-5}$-alkylamino, di-($C_{1-5}$-alkyl)-amino, $C_{3-5}$-cycloalkyleneimino, $C_{1-5}$-alkyl-carbonylamino group,
a $C_{1-5}$-alkyl group which may be substituted by 1-3 fluorine atoms, a hydroxy-$C_{1-5}$-alkyl, $C_{1-5}$-alkyloxy-$C_{1-5}$-alkyl, amino-$C_{1-5}$-alkyl, $C_{1-5}$-alkylamino-$C_{1-5}$-alkyl, di-($C_{1-5}$-alkyl)-amino-$C_{1-5}$-alkyl, $C_{4-7}$-cycloalkyleneimino-$C_{1-5}$-alkyl, carboxy-$C_{0-5}$-alkyl, $C_{1-5}$-alkyloxycarbonyl-$C_{0-5}$-alkyl, aminocarbonyl-$C_{0-5}$-alkyl, $C_{1-5}$-alkylaminocarbonyl-$C_{0-5}$-alkyl, di-($C_{1-5}$-alkyl)-aminocarbonyl-$C_{0-5}$-alkyl or a $C_{4-7}$-cycloalkyleneiminocarbonyl-$C_{0-5}$-alkyl group, wherein the two groups $R^{7b}/R^{7c}$ may not simultaneously be bound to the cyclic carbon atom via a heteroatom, except that —C($R^{7b}R^{7c}$)—corresponds to a —CF$_2$ group, or $R^{7a}$ denotes a phenyl or monocyclic heteroaryl group substituted by fluorine, chlorine, bromine, methyl, methoxy, amino or nitro, or two groups $R^{7b}/R^{7c}$ together with the cyclic carbon atom may form a 3-, 4-, 5-, 6- or 7-membered saturated carbocyclic group or a cyclopentene, cyclohexene, oxetan, azetidine, thietan, tetrahydrofuran, pyrrolidine, tetrahydrothiophene, tetrahydropyran, piperidine, pentamethylene sulphide, hexamethyleneimine, 1,3-dioxolan, 1,4-dioxane, hexahydropyridazine, piperazine, thiomorpholine, morpholine, 2-imidazolidinone, 2-oxazolidinone, tetrahydro-2(1H)-pyrimidinone or [1,3]oxazinan-2-one ring, wherein the methylene groups thereof may be substituted by 1-2 $C_{1-3}$-alkyl or CF$_3$— groups, and/or the methylene groups thereof, if they are not bound to a heteroatom, may be substituted by 1-2 fluorine atoms, and/or wherein a —CH$_2$ group, besides being replaced by an N atom, may be replaced by a —CO group, and/or the imino groups thereof may each be substituted by a $C_{1-3}$-alkyl or $C_{1-3}$-alkylcarbonyl group, and/or wherein the sulphur atom may be oxidised to form a sulphoxide or sulphone group, $K^2$ and $K^3$ each independently denote a —CH$_2$, —CHR$^{8a}$, —CR$^{8b}$R$^{8c}$ or a —C(O) group, wherein $R^{8a}/R^{8b}/R^{8c}$ each independently denote a $C_{1-5}$-alkyl group which may be substituted by 1-3 fluorine atoms, a hydroxy-$C_{1-5}$-alkyl, $C_{1-5}$-alkyloxy-$C_{1-5}$-alkyl, amino-$C_{1-5}$-alkyl, $C_{1-5}$-alkylamino-$C_{1-5}$-alkyl, di-($C_{1-5}$-alkyl)-amino-$C_{1-5}$-alkyl, $C_{4-7}$-cycloalkyleneimino-$C_{1-5}$-alkyl, carboxy-$C_{0-5}$-alkyl, $C_{1-5}$-alkyloxycarbonyl-$C_{0-5}$-alkyl, aminocarbonyl-$C_{0-5}$-alkyl, $C_{1-5}$-alkylaminocarbonyl-$C_{0-5}$-alkyl, di-($C_{1-5}$-alkyl)-aminocarbonyl-$C_{0-5}$-alkyl or a $C_{4-7}$-cycloalkyleneiminocarbonyl-$C_{0-5}$-alkyl group, or two groups $R^{8b}/R^{8c}$ together with the cyclic carbon atom may form a 3-, 4-, 5-, 6- or 7-membered saturated carbocyclic group or a cyclopentene, cyclohexene, oxetan, azetidine, thietan, tetrahydrofuran, pyrrolidine, tetrahydrothiophene, tetrahydropyran, piperidine, pentamethylene sulphide, hexamethyleneimine, hexahydropyridazine, tetrahydro-2(1H)-pyrimidinone, [1,3]oxazinan-2-one ring, wherein the methylene groups thereof may be substituted by 1-2 $C_{1-3}$-alkyl or CF$_3$—groups, and/or the methylene groups thereof, if they are not bound to a heteroatom, may be substituted by 1-2 fluorine atoms, and/or wherein a —CH$_2$ group besides being replaced by a nitrogen atom may be replaced by a —CO group, and/or the imino groups thereof may each be substituted by a $C_{1-3}$-alkyl or $C_{1-3}$-alkylcarbonyl group, and/or wherein the sulphur atom may be oxidised to form a sulphoxide or sulphone group, with the proviso that a heteroatom introduced by $R^{8b}$ or $R^{8c}$ must not be only one carbon atom away from X in formula (I), and in all, in formula (IIa) or (IIb) or (IIc) a maximum of four groups selected from among $R^{7a}$, $R^{7b}$, $R^{7c}$, $R^{8a}$, $R^{8b}$ and $R^{8c}$ may be present, and X denotes an oxygen or sulphur atom, a CF$_2$, sulphene, sulphone or a NR$^1$ group, wherein $R^1$ denotes a hydrogen atom or a hydroxy, $C_{1-3}$-alkyloxy, amino, $C_{1-3}$-alkylamino, di-($C_{1-3}$-alkyl)-amino, a $C_{1-5}$-alkyl, $C_{2-5}$-alkenyl-CH$_2$, $C_{2-5}$-alkynyl-CH$_2$, $C_{3-6}$-cycloalkyl, $C_{4-6}$-cycloalkenyl, oxetan-3-yl, tetrahydrofuran-3-yl, benzyl, $C_{1-5}$-alkyl-carbonyl, trifluoromethylcarbonyl, $C_{3-6}$-cycloalkyl-carbonyl, $C_{1-5}$-alkyl-sulphonyl, $C_{3-6}$-cycloalkyl-sulphonyl, aminocarbonyl, $C_{1-5}$-alkylaminocarbonyl, di-($C_{1-5}$-alkyl)-aminocarbonyl, $C_{1-5}$-alkyloxycarbonyl, $C_{4-7}$-cycloalkyleneiminocarbonyl group, wherein the methylene and methyl groups present in the groups mentioned previously may additionally be substituted by a $C_{1-3}$alkyl, carboxy, $C_{1-5}$-alkoxycarbonyl group, or by a hydroxy, $C_{1-5}$-alkyloxy, amino, $C_{1-5}$-alkylamino, $C_{1-5}$-dialkylamino or $C_{4-7}$-cycloalkylenennino group, provided that the methylene or methyl groups are not directly bound to a heteroatom selected from among O, N and S, and/or one to three hydrogen atoms may be replaced by fluorine atoms, provided that the methylene or methyl groups are not directly bound to a heteroatom selected from among O, N and S, and wherein $A^1$ denotes either N or CR$^{10}$, $A^2$ denotes either N or CR$^{11}$, $A^3$ denotes either N or CR$^{12}$, $A^4$ denotes either N or CR$^{12}$, $A^5$ denotes NH, sulphur or oxygen, while $R^{10}$, $R^{11}$ and $R^{12}$ each independently denote a hydrogen, fluorine, chlorine, bromine or iodine atom, or a $C_{1-5}$-alkyl, CF$_3$, $C_{2-5}$-alkenyl, $C_{2-5}$-alkynyl, a phenyl, a cyano, carboxy, $C_{1-5}$-alkyloxycarbonyl, hydroxy, $C_{1-3}$-alkyloxy, CF$_3$O, CHF$_2$O, CH$_2$FO, amino, $C_{1-5}$-alkylamino, di-($C_{1-5}$-alkyl)-amino or $C_{4-7}$-cycloalkyleneimino group, and -L-E-G-J- denotes a —C—C—C—C group which may be substituted by $R^4$ and $R^5$, and $L^1$ denotes a —C(O) group, and $R^4$ denotes a hydrogen atom or a straight-chain or branched $C_{1-6}$-alkyl, $C_{2-6}$-alkenyl or $C_{2-6}$-alkynyl group, wherein the hydrogen atoms of the methylene and/or methyl fragments of the straight-chain or branched $C_{1-6}$-alkyl, $C_{2-6}$-alkenyl or $C_{2-6}$-alkynyl group may optionally be wholly or partly replaced by fluorine atoms, and/or wherein the hydrogen atoms of the methylene and/or methyl fragments of the straight-chain or branched $C_{1-6}$-alkyl, $C_{2-6}$-alkenyl or $C_{2-6}$-alkynyl group may optionally each be substituted independently by one to two substituents selected from a $C_{3-5}$-cycloalkyl group, a nitrile, hydroxy or $C_{1-5}$-alkyloxy group, wherein the hydrogen atoms of the $C_{1-5}$-alkyloxy group may optionally be wholly or partly replaced by fluorine atoms, an allyloxy, propargyloxy, benzyloxy, $C_{1-5}$-alkylcarbonyloxy, $C_{1-5}$-alkylaminocarbonyloxy, di-($C_{1-5}$-alkyl)-aminocarbonyloxy, $C_{1-5}$-alkyloxycarbonyloxy, carboxy-$C_{1-5}$-alkyloxy, $C_{1-5}$-alkyloxycarbonyl-$C_{1-5}$-alkyloxy, mercapto, $C_{1-5}$-alkylsulphanyl, $C_{1-5}$-alkylsulphinyl, $C_{1-5}$-alkylsulphonyl, carboxy, $C_{1-5}$-alkyloxycarbonyl, aminocarbonyl, $C_{1-5}$-alkylaminocarbonyl, di-($C_{1-5}$-alkyl)-aminocarbonyl, $C_{4-7}$-cycloalkyleneiminocarbonyl, aminosulphonyl, $C_{1-5}$-alkylaminosulphonyl, di-($C_{1-5}$-alkyl)-aminosulphonyl, $C_{4-7}$-cycloalkyleneiminosulphonyl, amino, $C_{1-5}$-alkylamino, di-($C_{1-5}$-alkyl)-amino, $C_{1-5}$-alkylcarbonylamino, $C_{1-3}$-alkyloxy-$C_{1-2}$-alkylcarbonylamino, $C_{1-3}$-alkyloxycarbonylamino, $C_{1-3}$-alkylaminocarbonylamino, $C_{1-5}$-alkyl-sulphonylamino, N—($C_{1-5}$-alkylsulphonyl)-$C_{1-5}$-alkylamino, $C_{3-6}$-cycloalkylcarbonylamino group, or morpholinyl, thiomorpholinyl, pyrrolidinyl, piperidinyl, piperazinyl, tetrahydrofuranyl, tetrahydropyranyl group, while the above-mentioned carbocyclic and heterocyclic groups in the ring may each be substituted by 1-4 $C_{1-3}$-alkyl or $C_{1-3}$-alkylcarbonyl groups or in each case by 1-2 oxo groups, and/or
  wherein the hydrogen atoms of the sp²-hybridised carbon atoms of the straight-chain or branched $C_{2-6}$-alkenyl group may optionally be wholly or partly replaced by fluorine atoms, or
a nitrile, carboxy, aminocarbonyl, $C_{1-5}$-alkylaminocarbonyl, $C_{3-6}$-cycloalkylamino-carbonyl, di-($C_{1-5}$-alkyl)-aminocarbonyl, $C_{1-5}$-alkyloxycarbonyl or a $C_{4-7}$-cycloalkyleneiminocarbonyl group wherein a methylene group may optionally be replaced by an oxygen, sulphur or $C_{0-3}$-alkyl-substituted nitrogen atom, or
a phenyl, mono- or bicyclic heteroaryl, phenyl-$C_{1-5}$-alkyl or mono- or bicyclic heteroaryl-$C_{1-5}$-alkyl group,
  which may optionally be mono- to trisubstituted in the phenyl or heteroaryl moiety by identical or different substituents selected from among fluorine, chlorine, bromine and iodine atoms, and $C_{1-5}$-alkyl, trifluoromethyl, amino, $C_{1-5}$-alkyl-amino, di-($C_{1-5}$-alkyl)-amino, hydroxy, $C_{1-5}$-alkyloxy, mono-, di- or trifluoromethoxy, carboxy- and $C_{1-5}$-alkyloxycarbonyl group,
or if $R^4$ is linked to G it may also denote a fluorine atom or a hydroxy, $C_{1-5}$-alkyl-oxy, $C_{2-5}$-alkenyl-oxy, $C_{2-5}$-alkynyl-oxy, $C_{3-6}$-cycloalkyl-oxy, $C_{1-5}$-alkylaminocarbonyloxy, di($C_{1-5}$-alkyeaminocarbonyloxy or $C_{4-7}$-cycloalkyleneiminocarbonyloxy, phenyl-$C_{0-3}$-alkyloxy, heteroaryl-$C_{0-3}$-alkyl-oxy, amino, $C_{1-5}$-alkylamino, di-($C_{1-5}$-alkyl)-amino, $C_{4-7}$-cycloalkyleneimino, $C_{1-3}$-acylamino, ($C_{1-3}$-acyl)$C_{1-3}$-alkylamino, $C_{1-5}$-alkyloxycarbonylamino, $C_{1-5}$-alkylaminocarbonyl amino, di($C_{1-5}$-alkyl)aminocarbonylamino or a $C_{4-7}$-cycloalkyleneiminocarbonylamino-group,
  wherein the methyl or methylene groups present in the above-mentioned alkyl or cycloalkyl groups may each independently be substituted by a substituent selected from among morpholinyl, thiomorpholinyl, pyrrolidinyl, piperidinyl, piperazinyl, tetrahydrofuranyl, tetrahydropyranyl, dimethylaminocarbonyl, $C_{1-5}$-alkyloxycarbonyl, carboxy, methyl, hydroxy, methoxy or amino, and
the above-mentioned phenyl or heteroaryl groups may optionally be mono- to trisubstituted by identical or different substituents selected from among fluorine, chlorine, bromine and iodine atoms, and $C_{1-5}$-alkyl, trifluoromethyl, amino, $C_{1-5}$-alkyl-amino, di-($C_{1-5}$-alkyl)-amino, hydroxy, $C_{1-5}$-alkyloxy, mono-, di- or trifluoromethoxy, carboxy- and $C_{1-5}$-alkyloxycarbonyl group,
with the proviso that two heteroatoms selected from among oxygen and nitrogen are separated from one another by precisely one optionally substituted —$CH_2$ group, and/or
that two atoms form an —O—O or —S—O bond,
is excluded, and
$R^5$ denotes a hydrogen atom, a $C_{1-5}$alkyl, $C_{2-5}$alkenyl or $C_{2-5}$alkynyl or a phenyl-$C_{0-5}$alkyl group, wherein the alkyl group may be substituted by a hydroxy, methoxy, hydroxycarbonyl or $C_{1-5}$alkoxycarbonyl group,
or if $R^5$ is linked to G it may also denote a hydroxy or methoxy group, or
$R^4$ and $R^5$ provided that they are bound to the same carbon atom, may form, together with the carbon atom, a —C=O group or a —$CF_2$ group, or
$R^4$ and $R^5$ provided that they are bound to the same carbon atom or to two adjacent carbon atoms, may form, together with the carbon atom or atoms a 3-7-membered carbocyclic group or a monounsaturated 5-7 membered carbocyclic group
  wherein one of the carbon chain members of this cyclic group may be replaced by an oxygen or sulphur atom or an —NH, —N($C_{1-5}$-alkyl), —N($C_{1-4}$-alkylcarbonyl) or a carbonyl, sulphinyl or sulphonyl group, and/or
  wherein two directly adjacent carbon chain members of these $C_{4-7}$-carbocyclic groups may together be replaced by a —C(O)NH, —C(O)N($C_{1-5}$-alkyl), —S(O)$_2$NH or —S(O)$_2$N($C_{1-5}$-alkyl) group, and/or
  wherein four directly adjacent carbon chain members of these $C_{5-7}$-carbocyclic groups may together be replaced by a —O—$CH_2$—$CH_2$—O group, and/or
  wherein 1 to 3 carbon atoms of these 3-7-membered cyclic groups may optionally each be substituted independently of one another by one or two fluorine atoms or one or two $C_{1-5}$-alkyl groups or a hydroxy, $C_{1-5}$-alkyloxy, $C_{1-5}$-alkylcarbonyloxy, amino, $C_{1-5}$-alkylamino, di-($C_{1-5}$-alkyl)-amino, $C_{4-7}$-cycloalkyleneimino, $C_{1-5}$-alkylcarbonylamino, $C_{3-6}$-cycloalkylcarbonylamino, nitrile, carboxy-$C_{1-5}$-alkyl, $C_{1-5}$-alkyloxycarbonyl-$C_{1-5}$-alkyl, carboxy, $C_{1-5}$-alkyloxycarbonyl, aminocarbonyl, $C_{1-5}$-alkylaminocarbonyl, di-($C_{1-5}$-alkyl)-aminocarbonyl or $C_{4-7}$-cycloalkyleneiminocarbonyl group,
with the proviso that a cyclic group formed from $R^4$ and $R^5$ together,
wherein two nitrogen atoms or one nitrogen and one oxygen atom in the cyclic group are separated from one another by precisely one optionally substituted —$CH_2$ group, and/or
wherein two atoms in the ring form an —O—O or —S—O— bond,
is excluded, and
$L^2$ denotes a —C(O) group, and
M denotes a phenyl, pyridyl, thienyl or furyl ring optionally substituted by $R^2$ and $R^3$, wherein
$R^2$ denotes a fluorine, chlorine, bromine or iodine atom or a methyl, ethyl, vinyl, methoxy, ethynyl, cyano or —C(O)$NH_2$ group, and
$R^3$ denotes a hydrogen, fluorine, chlorine, bromine or iodine atom or a hydroxy, methoxy, trifluoromethoxy group, or a $C_{1-3}$-alkyl group optionally substituted by fluorine atoms, or a cyano, amino or $NH_2$C(O) group, while, unless stated otherwise, by the term "heteroaryl group" mentioned in the definitions hereinbefore is meant a monocyclic 5- or 6-membered heteroaryl group, wherein the 6-membered heteroaryl group contains one, two or three nitrogen atoms, and the 5-membered heteroaryl group contains an imino group optionally substituted by a $C_{1-3}$-alkyl group or an oxygen or sulphur atom, or an imino group optionally substituted by a $C_{1-3}$-alkyl group or an oxygen or sulphur atom and additionally one or two nitrogen atoms, or an imino group optionally substituted by a $C_{1-3}$-alkyl group and three nitrogen atoms, and moreover a phenyl ring optionally substituted by a fluorine, chlorine or bromine atom or by a $C_{1-3}$-alkyl, hydroxy, $C_{1-3}$-alkyloxy group, amino, $C_{1-3}$-alkylamino, di-($C_{1-3}$-alkyl)-amino or $C_{3-6}$-cycloalkyleneimino group may be fused to the above-mentioned monocyclic heteroaryl groups via two adjacent carbon atoms, and the bond is effected via a nitrogen atom or a carbon atom of the heterocyclic moiety or a fused-on phenyl ring, and wherein, unless stated otherwise, by the term "halogen atom" mentioned in the definitions hereinbefore is meant an atom selected from among fluorine, chlorine, bromine and iodine, and wherein, unless stated otherwise, the alkyl, alkenyl, alkynyl and alkyloxy groups contained in the definitions mentioned previously which have more than two carbon atoms may be straight-chain or branched and the alkyl groups in the previously mentioned dialkylated groups, for example the dialkylamino groups, may be identical or different, and the hydrogen atoms of the methyl or ethyl groups contained in the foregoing definitions, unless otherwise stated, may be wholly or partly replaced by fluorine atoms, a tautomers, enantiomers, diastereomers, mixtures and salts thereof.

2. A compound of formula (I) according to claim 1, wherein $R^4$ denotes a hydrogen atom or a straight-chain or branched $C_{1-6}$-alkyl group, wherein the hydrogen atoms of the methylene and/or methyl fragments of the straight-chain or branched $C_{1-6}$-alkyl group may optionally be wholly or partly replaced by fluorine atoms, and/or wherein the hydrogen atoms of the methylene and/or methyl fragments of the straight-chain or branched $C_{1-6}$-alkyl group may optionally each independently be substituted by a substituent selected from a hydroxy, $C_{1-5}$-alkyloxy, $C_{1-5}$-alkylaminocarbonyloxy, di-($C_{1-5}$-alkyl)-aminocarbonyloxy, carboxy, $C_{1-5}$-alkyloxycarbonyl, aminocarbonyl, $C_{1-5}$-alkylaminocarbonyl, di-($C_{1-5}$-alkyl)-aminocarbonyl, $C_{4-7}$-cycloalkyleneiminocarbonyl, amino, $C_{1-5}$-alkylamino, di-($C_{1-5}$-alkyl)-amino, $C_{1-5}$-alkylcarbonylamino, $C_{1-3}$-alkyloxy-$C_{1-2}$-alkylcarbonylamino, $C_{1-3}$-alkyloxycarbonylamino, $C_{1-3}$-alkylaminocarbonylamino, $C_{1-5}$-alkylsulphonylamino, N-($C_{1-5}$-alkylsulphonyl)-$C_{1-5}$-alkylamino, $C_{3-6}$-cycloalkylcarbonylamino group, or a nitrile, carboxy, aminocarbonyl, $C_{1-5}$-alkylaminocarbonyl, $C_{3-6}$-cycloalkylamino-carbonyl, di-($C_{1-5}$-alkyl)-aminocarbonyl, $C_{1-5}$-alkyloxycarbonyl or a $C_{4-7}$-cycloalkylenenninocarbonyl group wherein a methylene group may optionally be replaced by an oxygen, sulphur or $C_{0-3}$-alkyl-substituted nitrogen atom, and or if $R^4$ is linked to G it may also denote a fluorine atom or a hydroxy, $C_{1-5}$-alkyl-oxy, $C_{2-5}$-alkenyl-oxy, $C_{2-5}$-alkynyl-oxy, $C_{3-6}$-cycloalkyl-oxy, $C_{1-5}$-alkylaminocarbonyloxy, di($C_{1-5}$-alkyl)aminocarbonyloxy or $C_{4-7}$-cycloalkyleneiminocarbonyloxy, phenyl-$C_{0-2}$-alkyloxy group, amino, $C_{1-5}$-alkylamino, di-($C_{1-5}$-alkyl)-amino, $C_{4-7}$-cycloalkyleneimino, $C_{1-3}$-acylamino, ($C_{1-3}$-acyl)$C_{1-3}$-alkylamino, $C_{1-5}$-alkyloxycarbonylamino, $C_{1-5}$-alkylaminocarbonylamino, di($C_{1-5}$-alkyl) aminocarbonylamino or a $C_{4-7}$-cycloalkyleneiminocarbonylamino group, wherein the methyl or methylene groups present in the above-mentioned alkyl or cycloalkyl groups may each independently be substituted by a substituent selected from among dimethylaminocarbonyl, $C_{1-5}$-alkyloxycarbonyl, carboxy, methyl, hydroxy, methoxy or amino, with the proviso that two heteroatoms selected from among oxygen and nitrogen are separated from one another by precisely one optionally substituted —$CH_2$ group, and/or that two atoms form an —O—O or —S—O— bond, is excluded, and $R^5$ denotes a hydrogen atom or a $C_{1-5}$ alkyl, allyl, propargyl or benzyl group, or if $R^5$ is linked to G, it may also denote a hydroxy or methoxy group, or $R^4$ and $R^5$ if they are bound to the same carbon atom, may form, together with the carbon atom, a —C=O group or a —$CF_2$— group, or $R^4$ and $R^5$ if they are bound to the same carbon atom or to two adjacent carbon atoms, may form, together with the carbon atom or atoms, a 3-7-membered carbocyclic group, wherein one of the carbon chain members of this cyclic group may be replaced by an oxygen or sulphur atom or a —NH, —N($C_{1-5}$-alkyl), —N($C_{1-4}$-alkylcarbonyl) or a carbonyl, sulphinyl or sulphonyl group, and/or wherein two directly adjacent carbon chain members of these $C_{4-7}$-carbocyclic groups may together be replaced by a —C(O)NH, —C(O)N($C_{1-5}$-alkyl), —S(O)$_2$NH, or —S(O)$_2$N($C_{1-5}$-alkyl) group, and/or wherein four directly adjacent carbon chain members of these $C_{5-7}$-carbocyclic groups may together be replaced by a —O—$CH_2$—$CH_2$O group, with the proviso that a cyclic group formed from $R^4$ and $R^5$ together, wherein two nitrogen atoms or one nitrogen and one oxygen atom in the cyclic group are separated from one another by precisely one optionally substituted —$CH_2$ group, and/or wherein two atoms in the ring form an —O—O or —S—O bond, is excluded, a tautomers, enantiomers, diastereomers, mixtures and salts thereof.

3. A compound of formula (I) according to claim 1, wherein

D denotes a substituted bicyclic ring system of formula (IIa) or (IIb)

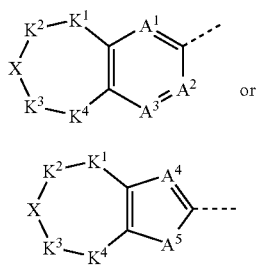

wherein
K¹ and K⁴
each independently denote a bond, a —CH₂, —CHR⁷ᵃ, —R⁷ᵇR⁷ᶜ or a —C(O) group, and wherein
R⁷ᵃ/R⁷ᵇ/R⁷ᶜ
each independently denote a fluorine atom, a hydroxy, $C_{1-5}$-alkyloxy or a $C_{1-5}$-alkyl group,
wherein the two groups R⁷ᵇ/R⁷ᶜ may not simultaneously be bound to the cyclic carbon atom via a heteroatom, except where —C(R⁷ᵇR⁷ᶜ)— corresponds to a —CF₂ group, or
two groups R⁷ᵇ/R⁷ᶜ together with the cyclic carbon atom may form a 3-membered carbocyclic group, with the proviso that K¹ and K⁴ simultaneously denote a bond, is excluded, and K² and K³
each independently denote a —CH₂, —CHR⁸ᵃ, —CR⁸ᵇR⁸ᶜ or a —C(O)— group, wherein
R⁸ᵃ/R⁸ᵇ/R⁸ᶜ
each independently denote a $C_{1-5}$-alkyl group, and/or
two groups R⁸ᵇ/R⁸ᶜ together with the cyclic carbon atom may form a 3-membered saturated carbocyclic group
and
in all in formulae (IIa) or (IIb) not more than four groups selected from among R⁷ᵃ, R⁷ᵇ, R⁷ᶜ, R⁸ᵃ, R⁸ᵇ and R⁸ᶜ may be present, and X denotes an oxygen or sulphur atom, a —CF₂— or a NR¹ group, wherein
R¹ denotes a hydrogen atom or a hydroxy, $C_{1-3}$-alkyloxy, amino, $C_{1-3}$-alkylamino, di-($C_{1-3}$-alkyl)-amino, a $C_{1-5}$-alkyl, $C_{2-5}$-alkenyl-CH₂, $C_{2-5}$-alkynyl-CH₂ or a $C_{3-6}$-cycloalkyl group,
and wherein
A¹ denotes either N or CR¹⁰,
A² denotes either N or CR¹¹,
A³ denotes either N or CR¹²,
A⁴ denotes either N or CR¹²,
A⁵ denotes NH, sulphur or oxygen,
wherein R¹⁰, R¹¹ and R¹² each independently denote
a hydrogen, fluorine, chlorine, bromine or iodine atom, or a $C_{1-5}$-alkyl, CF₃, a cyano, carboxy, $C_{1-5}$-alkyloxycarbonyl, hydroxy, $C_{1-3}$-alkyloxy, CF₃O, CHF₂O, CH₂FO, amino, $C_{1-5}$-alkylamino, di-($C_{1-5}$-alkyl)-amino or $C_{4-7}$-cycloalkyleneimino group,
a tautomer, enantiomer, diastereomer, or salt thereof.

4. A compound of formula (I) according to claim 1, wherein
X denotes a NR¹ group, wherein
R¹ denotes a hydrogen atom or a $C_{1-5}$-alkyl, allyl or cyclopropyl group, and
A¹ denotes CR¹⁰,
A² denotes CR¹¹,
A³ denotes CR¹²,
A⁴ denotes either N or CR¹²,
A⁵ denotes sulphur,
while R¹⁰, R¹¹ and R¹² each independently denote
a hydrogen, fluorine or chlorine atom, or a methyl, CF₃, hydroxy, methoxy, CF₃O, CHF₂O, CH₂FO group,
a tautomers, enantiomers, diastereomers, mixtures and salts thereof.

5. A compound of formula (I) according to claim 1, wherein
D denotes a substituted bicyclic ring system of formula

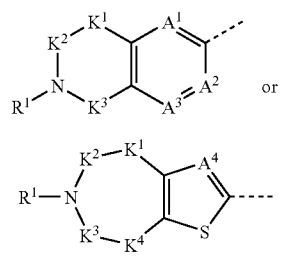

wherein
K¹ denotes a —CH₂, —CHR⁷ᵃ, or a —CR⁷ᵇR⁷ᶜ— group, and
K² and K³
each independently denote a —CH₂, —CHR⁸ᵃ, or a —CR⁸ᵇR⁸ᶜ— group, wherein
R⁸ᵃ/R⁸ᵇ/R⁸ᶜ each independently denote a $C_{1-5}$-alkyl group, and
K⁴ denotes a bond, a —CH₂, —CHR⁷ᵃ or a —CR⁷ᵇR⁷ᶜ group,
wherein
R⁷ᵃ denotes a $C_{1-5}$-alkyl group and
R⁷ᵇ/R⁷ᶜ each independently denote a hydroxy, $C_{1-5}$-alkyloxy or a $C_{1-5}$-alkyl group,
wherein the two groups R⁷ᵇ/R⁷ᶜ may not simultaneously be bound to the cyclic carbon atom via an oxygen atom, and
in all, in formulae (IIe) or (IIf) not more than four groups selected from among R⁷ᵃ, R⁷ᵇ, R⁷ᶜ, R⁸ᵃ, R⁸ᵇ and R⁸ᶜ may be present, and
R¹ denotes a hydrogen atom or a $C_{1-3}$-alkyl, allyl or cyclopropyl group, and wherein
A¹ denotes CR¹⁰,
A² denotes CR¹¹,
A³ denotes CR¹²,
A⁴ denotes either N or CR¹²,
while R¹⁰, R¹¹ and R¹² each independently denote
a hydrogen, fluorine or chlorine atom, or a methyl, CF₃, hydroxy, methoxy, CF₃O, CHF₂O, CH₂FO group, and -L-E-G-J- denotes a —C—C—C—C group which may be substituted by $R^4$ and $R^5$, and $R^4$ denotes a hydrogen atom or
- a straight-chain or branched $C_{1-3}$-alkyl group,
  - wherein the hydrogen atoms of the methylene and/or methyl fragments of the straight-chain or branched $C_{1-6}$-alkyl group may optionally be substituted independently of one another by a substituent selected from a hydroxy, $C_{1-5}$-alkyloxy, $C_{1-5}$-alkylaminocarbonyloxy, di-($C_{1-5}$-alkyl)-aminocarbonyloxy, carboxy, $C_{1-5}$-alkyloxycarbonyl, $C_{1-3}$-alkyloxy-$C_{1-2}$alkylcarbonylamino, $C_{1-3}$-alkyloxycarbonylamino, $C_{1-3}$-alkylaminocarbonylamino, $C_{1-5}$-alkylcarbonylamino, $C_{1-5}$-alkylsulphonylamino group, or
- if $R^4$ is linked to G, it may also denote a fluorine atom or a hydroxy, methoxy, $C_{3-5}$-alkenyl-oxy, $C_{2-5}$-alkyloxy, $C_{3-6}$-cycloalkyl-oxy, benzyloxy, $C_{1-5}$-alkylaminocarbonyloxy, di($C_{1-5}$-alkyl)aminocarbonyloxy or a $C_{4-7}$-cycloalkyleneiminocarbonyloxy group,
- with the proviso that
  - two heteroatoms selected from among oxygen and nitrogen are separated from one another by precisely one optionally substituted —$CH_2$ group, is excluded, and $R^5$ denotes a hydrogen atom or a $C_{1-5}$ alkyl, allyl, benzyl or phenyl group, or if $R^5$ is linked to G, it may also denote a hydroxy or methoxy group, or $R^4$ and $R^5$ if they are bound to the same carbon atom, may form together with the carbon atom a —C=O group, or a —$CF_2$— group, or $R^4$ and $R^5$ if they are bound to the same carbon atom or to two adjacent carbon atoms, may form together with the carbon atom or atoms a 3-6-membered carbocyclic group,
- wherein four directly adjacent carbon chain members of these $C_{5-6}$-carbocyclic groups may together be replaced by a —O—$CH_2$—$CH_2$O group, a tautomer, enantiomer, diastereomer, or salt thereof.

6. A compound of formula (I) according to claim 1, wherein
D denotes a substituted bicyclic ring system of formula

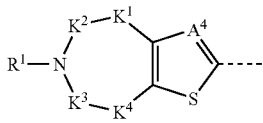

(IIf)

wherein
$K^1$ denotes a —$CH_2$, —$CHR^{7a}$, or a —$CR^{7b}R^{7c}$— group,
$K^2$ and $K^3$
each independently denote a —$CH_2$, —$CHR^{8a}$, or a —$CR^{8b}R^{8c}$— group, wherein $R^{8a}/R^{8b}/R^{8c}$ each independently denote a $C_{1-5}$-alkyl group, and $K^4$ denotes a bond, a —$CH_2$, —$CHR^{7a}$, or a —$CR^{7b}R^{7c}$— group,
wherein
$R^{7a}$ denotes a $C_{1-5}$-alkyl group, and
$R^{7b}/R^{7c}$ each independently denote a hydroxy, $C_{1-5}$-alkyloxy or a $C_{1-5}$-alkyl group,
wherein the two groups $R^{7b}/R^{7c}$ may not simultaneously be bound to the cyclic carbon atom via an oxygen atom,
and
in all, in formula (IIf) not more than four groups selected from among $R^{7a}$, $R^{7b}$, $R^{7c}$, $R^{8a}$, $R^{8b}$ and $R^{8c}$ may be present, and $R^1$ denotes a hydrogen atom or a $C_{1-3}$-alkyl or cyclopropyl group, and wherein
$A^1$ denotes $CR^{10}$,
$A^2$ denotes $CR^{11}$,
$A^3$ denotes $CR^{12}$,
$A^4$ denotes either N or $CR^{12}$,
wherein $R^{10}$, $R^{11}$ and $R^{12}$ each independently denote
a hydrogen, fluorine or chlorine atom, or a methyl, $CF_3$, hydroxy, methoxy, $CF_3O$, $CHF_2O$, $CH_2FO$ group, a tautomer, enantiomer, diastereomer, or salt thereof.

7. A compound of formula (I) according to claim 1, wherein
M denotes a thiophen-2-yl ring of formula

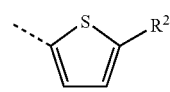

wherein
$R^2$ denotes a chlorine or bromine atom or an ethynyl group, a tautomer, enantiomer, diastereomer, or salt thereof.

8. A physiologically acceptable salt of the compound according to claim 1.

9. A medicament comprising a compound according to claim 1 or a physiologically acceptable salt thereof, optionally in addition to one or more inert carriers and/or diluents.

10. A method of inhibiting factor Xa and/or urokinase, factor VIIa, factor IX, factor XI and factor XII in a patient comprising administering to said patient a compound according to claim 1 or a physiologically acceptable salt thereof.

* * * * *